United States Patent
Cohen et al.

(10) Patent No.: US 11,559,373 B2
(45) Date of Patent: *Jan. 24, 2023

(54) STABLE WINGED AFFIXATION SYSTEM FOR GUIDED DENTAL IMPLANTATION

(71) Applicant: Image Navigation Ltd., Jerusalem (IL)

(72) Inventors: Yuval Cohen, Moshav Kisalon (IL); Vered Cohen Sharvit, Modiin (IL); Uri Sonenfeld, Jerusalem (IL); Jefferey Port, Neve Daniel (IL); Leonid Gootkin, Jerusalem (IL)

(73) Assignee: IMAGE NAVIGATION LTD., Jerusalem (IL)

(*) Notice: Subject to any disclaimer, the term of this patent is extended or adjusted under 35 U.S.C. 154(b) by 0 days.

This patent is subject to a terminal disclaimer.

(21) Appl. No.: 17/223,035

(22) Filed: Apr. 6, 2021

(65) Prior Publication Data

US 2021/0290340 A1    Sep. 23, 2021

Related U.S. Application Data

(63) Continuation-in-part of application No. 16/740,501, filed on Jan. 13, 2020, now Pat. No. 10,966,799.

(Continued)

(51) Int. Cl.
*A61C 1/08* (2006.01)
*A61B 34/20* (2016.01)
*A61C 8/00* (2006.01)

(52) U.S. Cl.
CPC ............. *A61C 1/084* (2013.01); *A61B 34/20* (2016.02); *A61C 8/0001* (2013.01); *A61C 8/0089* (2013.01)

(58) Field of Classification Search
CPC ....... A61C 1/084; A61C 8/0089; A61B 6/032; A61B 6/145; A61B 2090/3912;

(Continued)

(56) References Cited

U.S. PATENT DOCUMENTS 4,375,965 A * 3/1983 Weissman ............ A61C 9/0006
                                                                  433/37
7,457,443 B2   11/2008 Persky
(Continued)

FOREIGN PATENT DOCUMENTS

CN    108553186 A    9/2018

OTHER PUBLICATIONS

Block, Michael S. DMD et al. Static or Dynamic Navigation for Implant Placement—Choosing the Method of Guidance. American Association of Oral and Maxillofacial Surgeons. 2015. J Oral Maxillofac Surg: 1-9, 2015.

*Primary Examiner* — Matthew M Nelson
(74) *Attorney, Agent, or Firm* — Mark M. Friedman

(57) ABSTRACT

A stable affixation system for dental implantation includes a fixation tray having, for rapid placement, a housing defining a chamber whose inner surface is configured to house a flowable or malleable material and be placed over one or more teeth during guided dental implantation surgery. A central portion not configured to flex is situated between housing side walls. Each such side wall has an upper side portion and a lower side portion. Without the lock a squeezing force on the upper side portions flexes the lower side portions outward. The lock urges the upper side portions outward so as to flex the lower side portions inward. The lock reduces or eliminates freedom of movement of the tray. The system allows rapid removal and is sturdy enough to withstand forces including from various angles and leverage. The central portion may hold registration elements.

30 Claims, 56 Drawing Sheets

Related U.S. Application Data

(60) Provisional application No. 63/091,979, filed on Oct. 15, 2020.

(58) Field of Classification Search
CPC .... A61B 2090/3991; A61B 2090/3983; A61B 2090/3916; A61B 2090/3966
USPC .......................................................... 433/72
See application file for complete search history.

(56) References Cited

U.S. PATENT DOCUMENTS

| | | | | |
|---|---|---|---|---|
| 8,172,573 | B2 * | 5/2012 | Sonenfeld | A61C 8/0089 433/173 |
| 9,402,691 | B2 | 8/2016 | Merritt et al. | |
| 9,622,837 | B2 * | 4/2017 | Jansheski | A61C 9/0006 |
| 2002/0064753 | A1 * | 5/2002 | Philp, Jr. | A61C 9/0026 433/32 |
| 2010/0261133 | A1 * | 10/2010 | Lax | A61F 5/566 433/71 |
| 2011/0129796 | A1 * | 6/2011 | Riggio | A61C 19/04 433/171 |
| 2013/0224680 | A1 * | 8/2013 | McDonald | A61C 9/0006 433/38 |
| 2014/0272773 | A1 | 9/2014 | Merritt et al. | |
| 2014/0343405 | A1 * | 11/2014 | Daon | A61B 5/064 600/424 |
| 2015/0150658 | A1 * | 6/2015 | McDonald | A61C 9/0006 433/38 |
| 2017/0290554 | A1 | 10/2017 | Merritt | |
| 2018/0110596 | A1 * | 4/2018 | Ackel | A61F 9/0006 |
| 2018/0206957 | A1 * | 7/2018 | Ruth | A61C 9/0013 |
| 2019/0254776 | A1 | 8/2019 | Habeb et al. | |

* cited by examiner

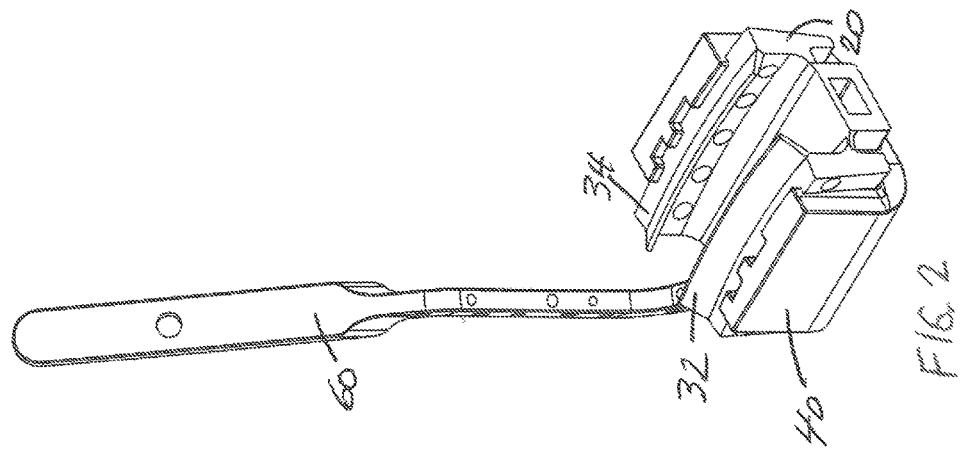
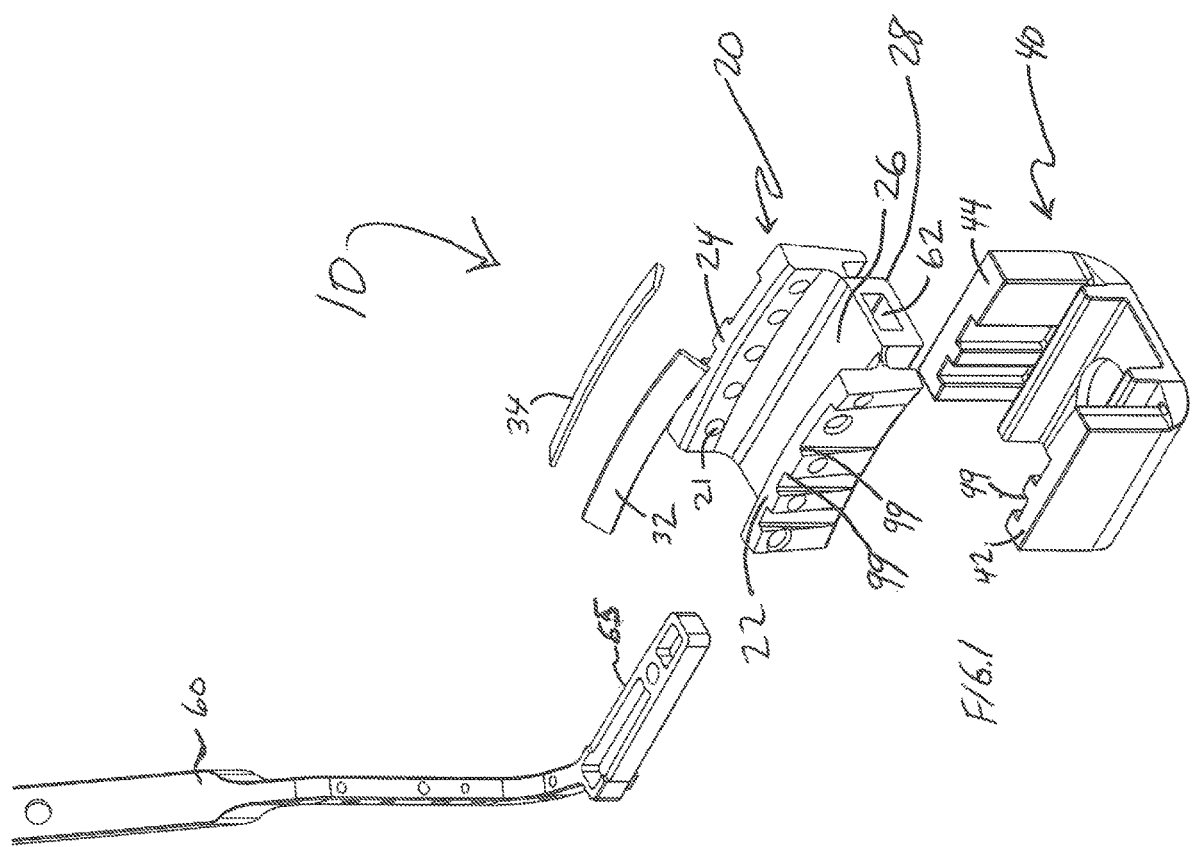

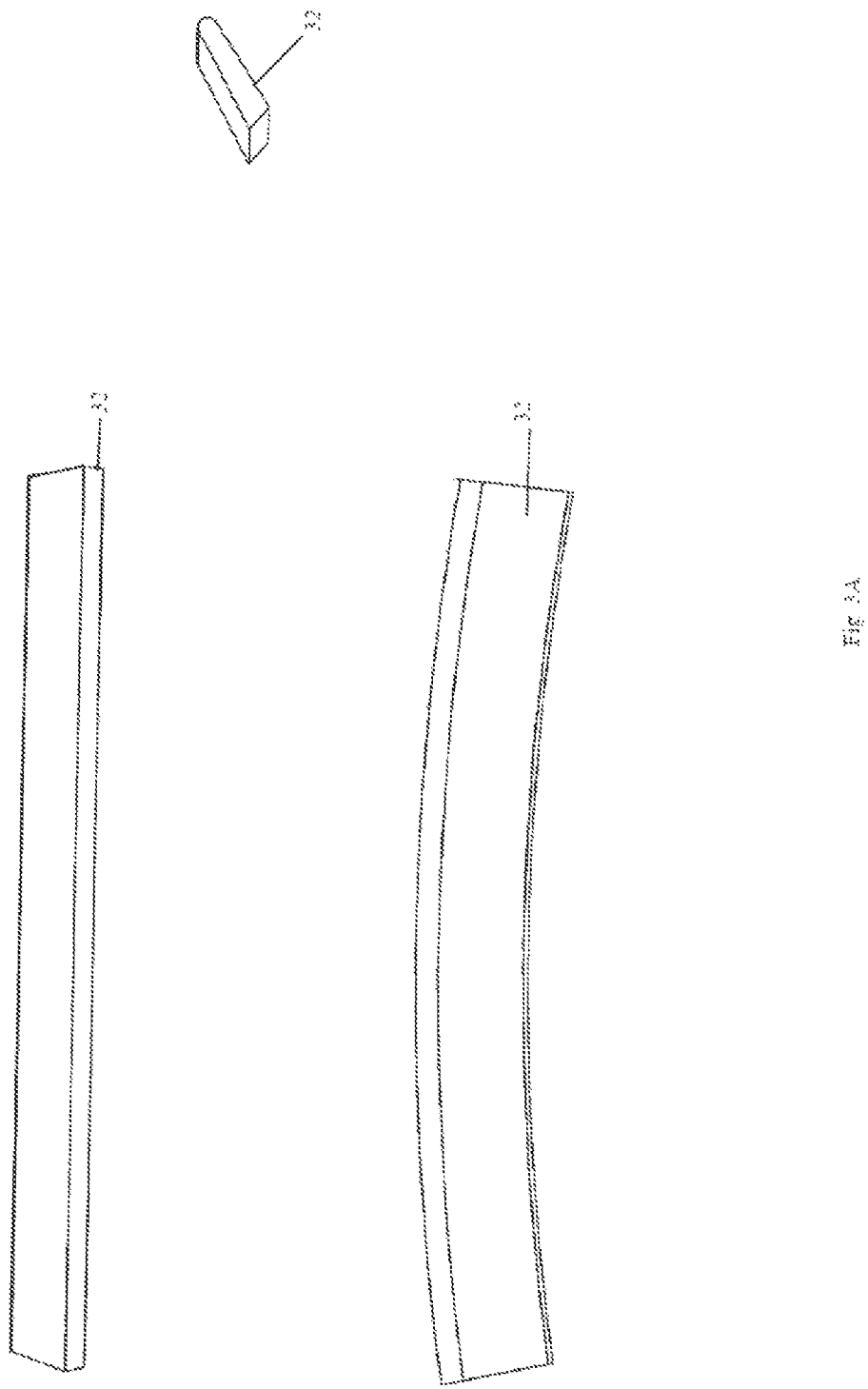

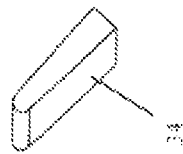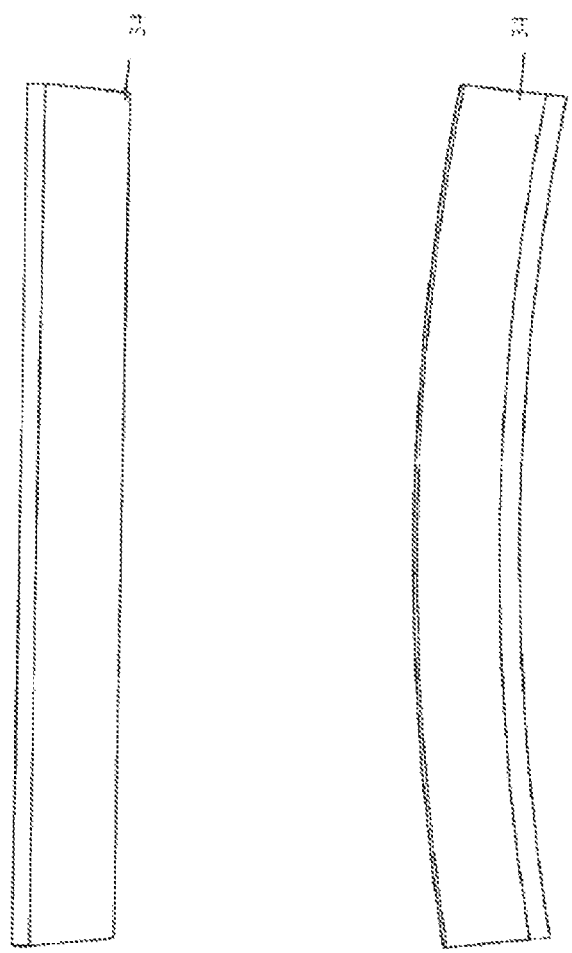
FIG. 4B

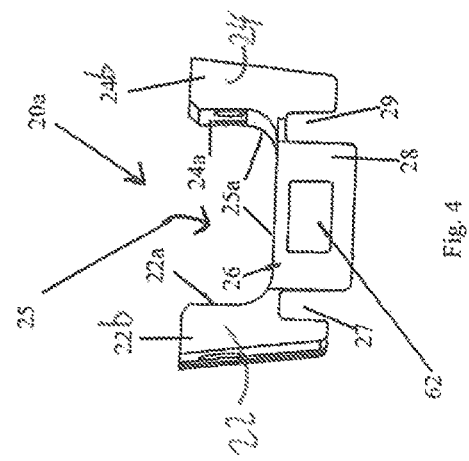
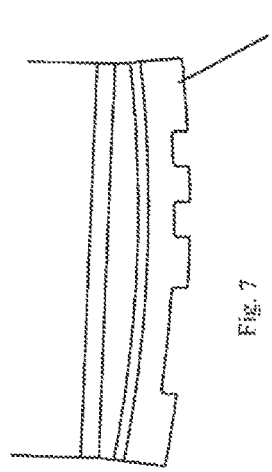
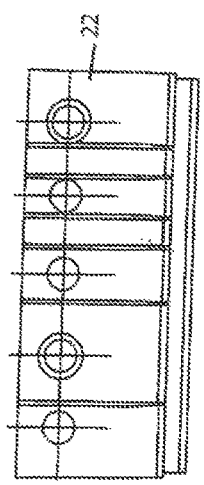
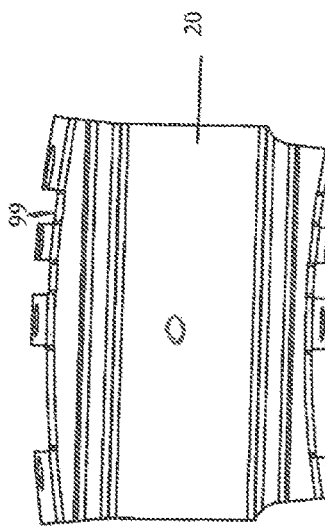

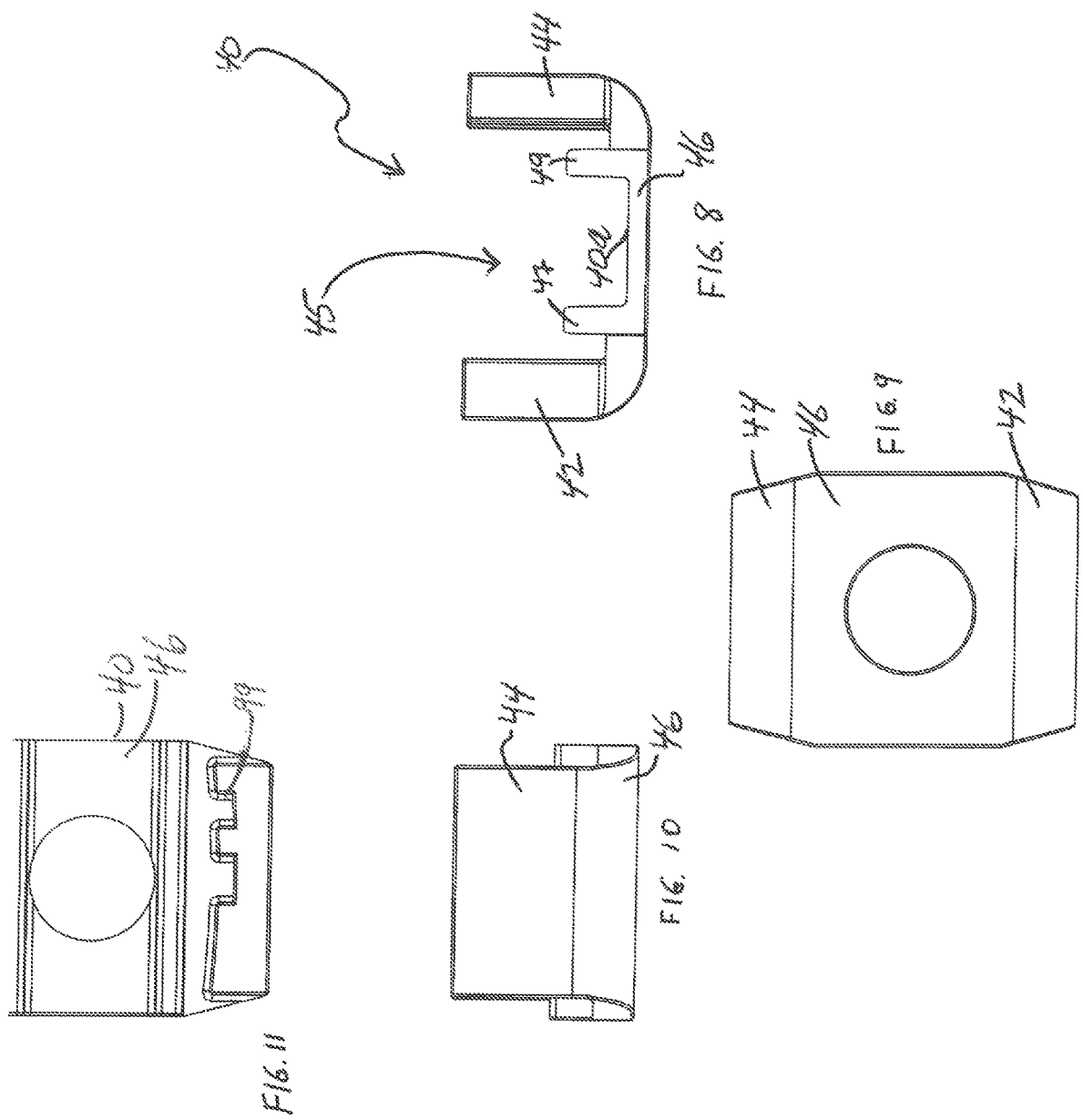

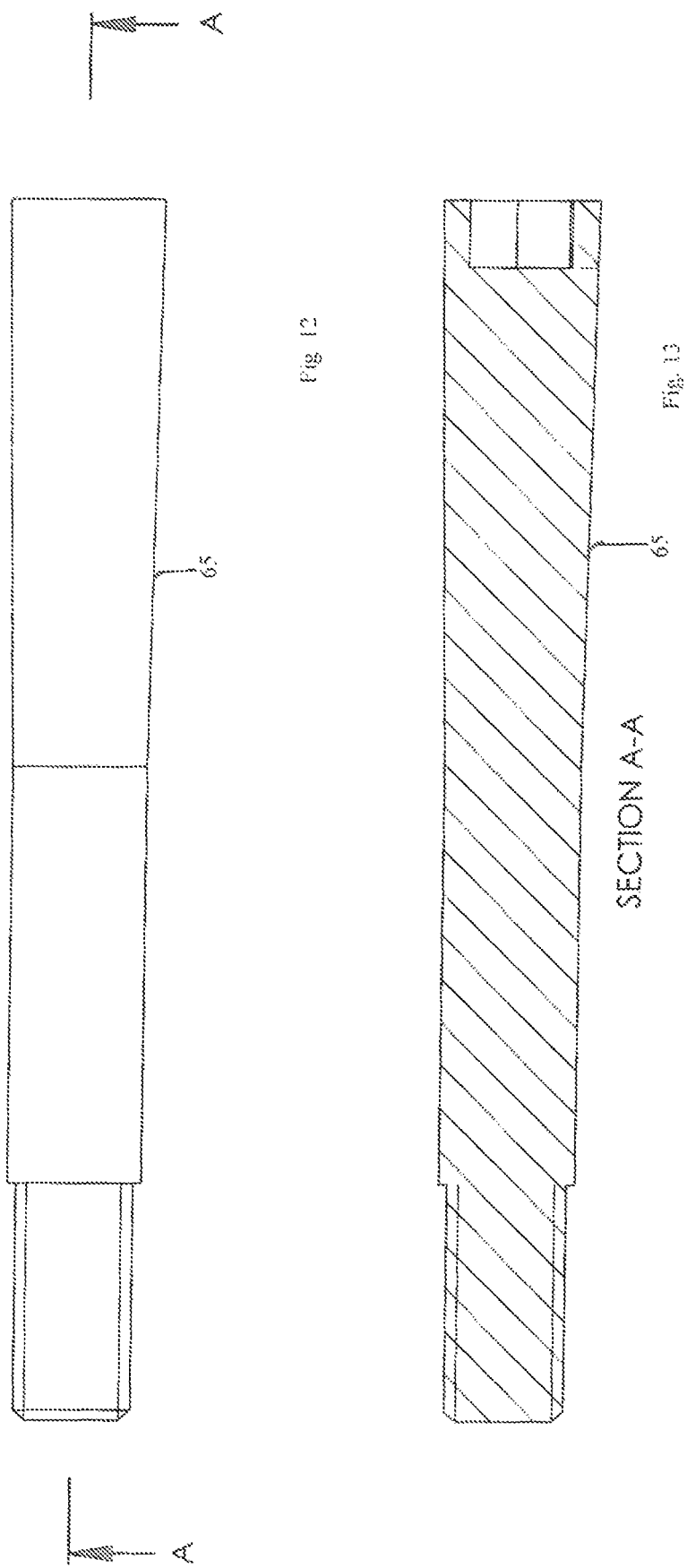

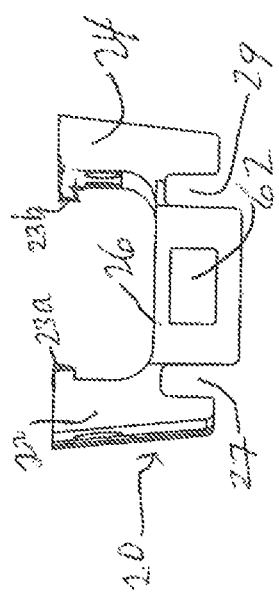

METHOD - 100

Deploying a fixation tray holding a flowable or malleable material over one or more teeth, the fixation tray having a housing defining a chamber and having a mechanism to urge the material against the one or more teeth ~ 110

Locking the fixation tray to reduce or eliminate its freedom of movement ~ 120

Allowing the flowable or malleable material to harden into a rigid but crisp state ~ 130

Removing or unlocking the lock and then removing the fixation tray ~ 140

METHOD - 200

Deploying a fixation tray holding a flowable or malleable material over one or more teeth, the fixation tray having side walls at least a portion of which are configured to flex under pressure, the side walls having extra flexible arm extensions inwardly facing to urge the flowable material

210

Locking the fixation tray to reduce its freedom of movement

220

Allowing the flowable or malleable material to harden into a rigid state

230

Removing or unlocking the lock and then removing the fixation tray by using a mechanism to exert a force on the fixation tray, thereby pressuring the at least a portion of the side walls to flex

METHOD - 400

Deploying a fixation tray holding a flowable or malleable material over one or more teeth, the fixation tray having a housing defining a chamber and having a mechanism to urge the material against the one or more teeth

410

Locking the fixation tray to reduce or eliminate its freedom of movement

420

Allowing the material to harden and performing the guided surgery while the tray and lock remain in place in a sturdy and stable position

430

Removing or unlocking the lock and then removing the fixation tray

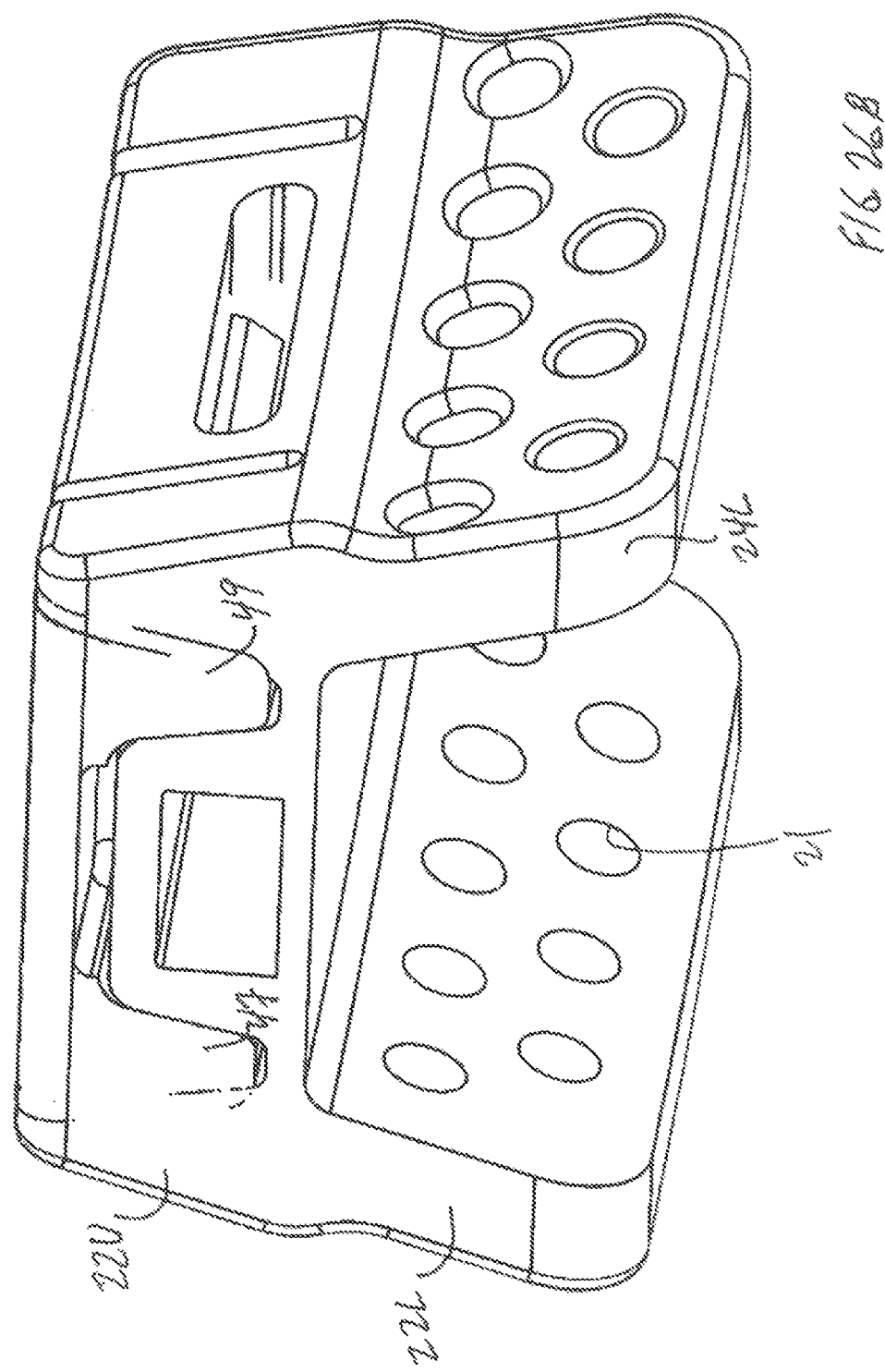

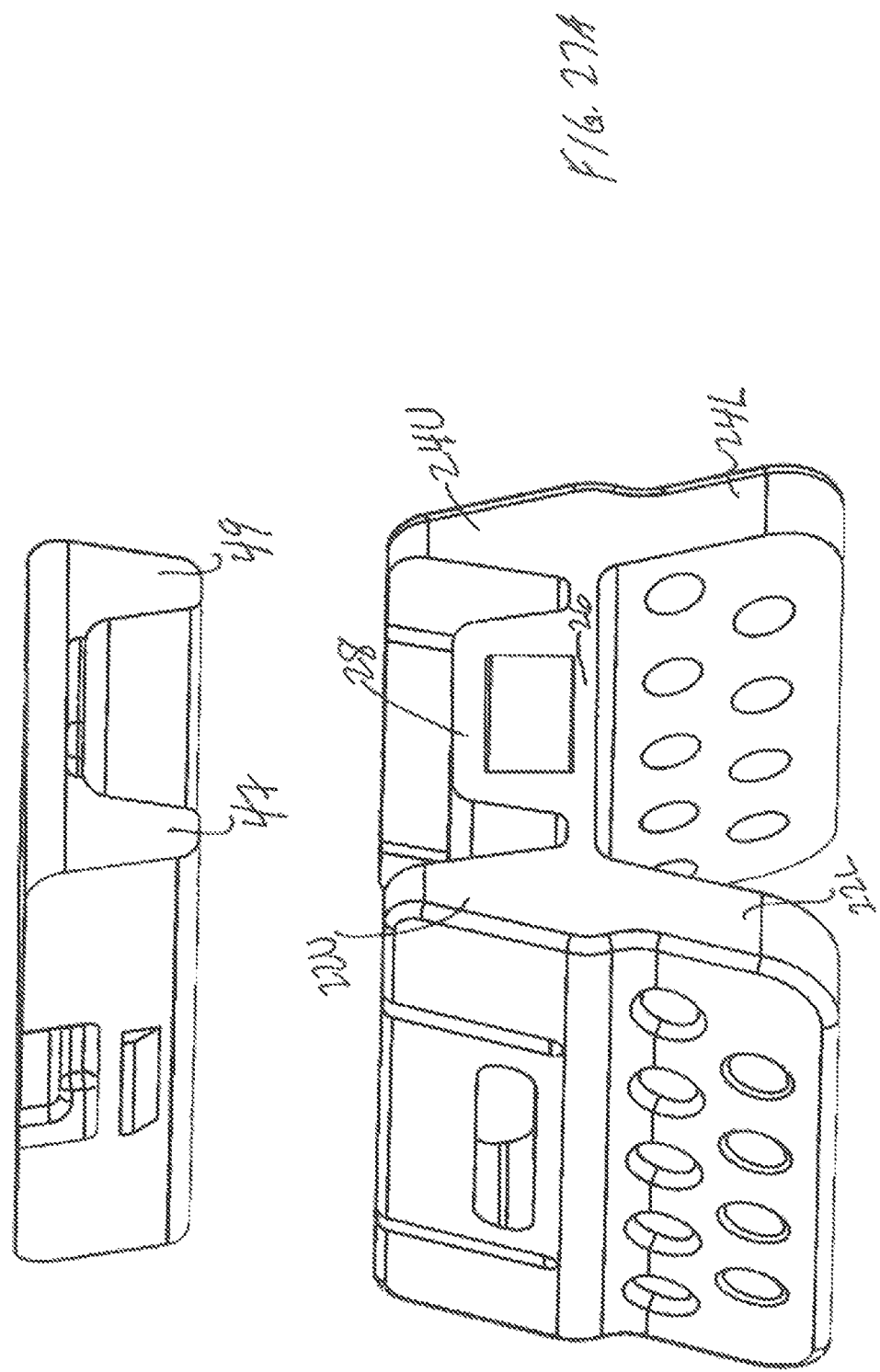

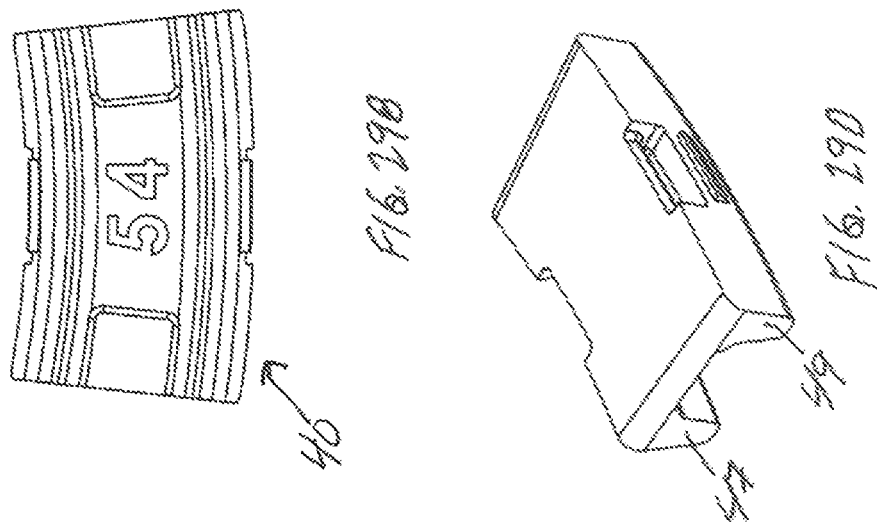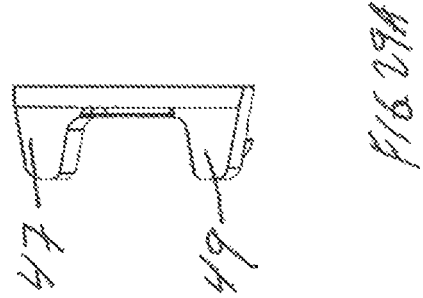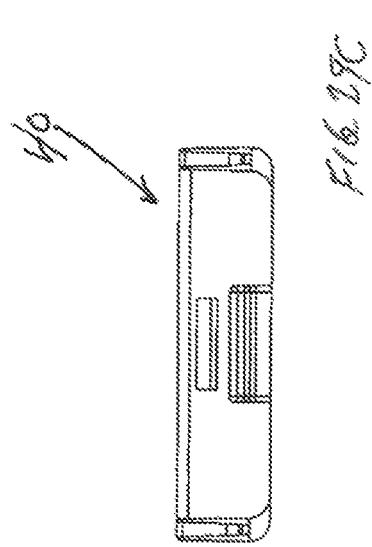

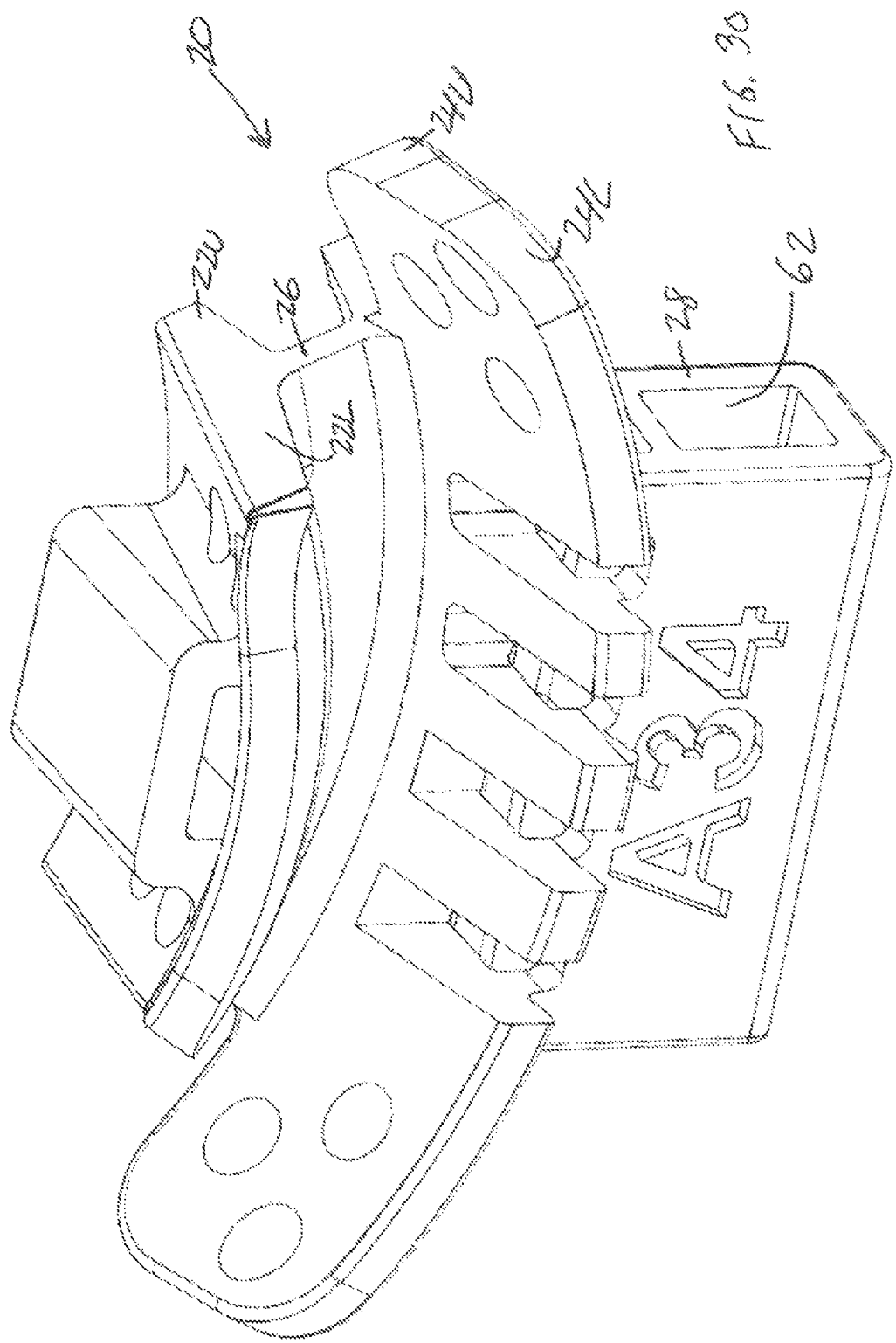

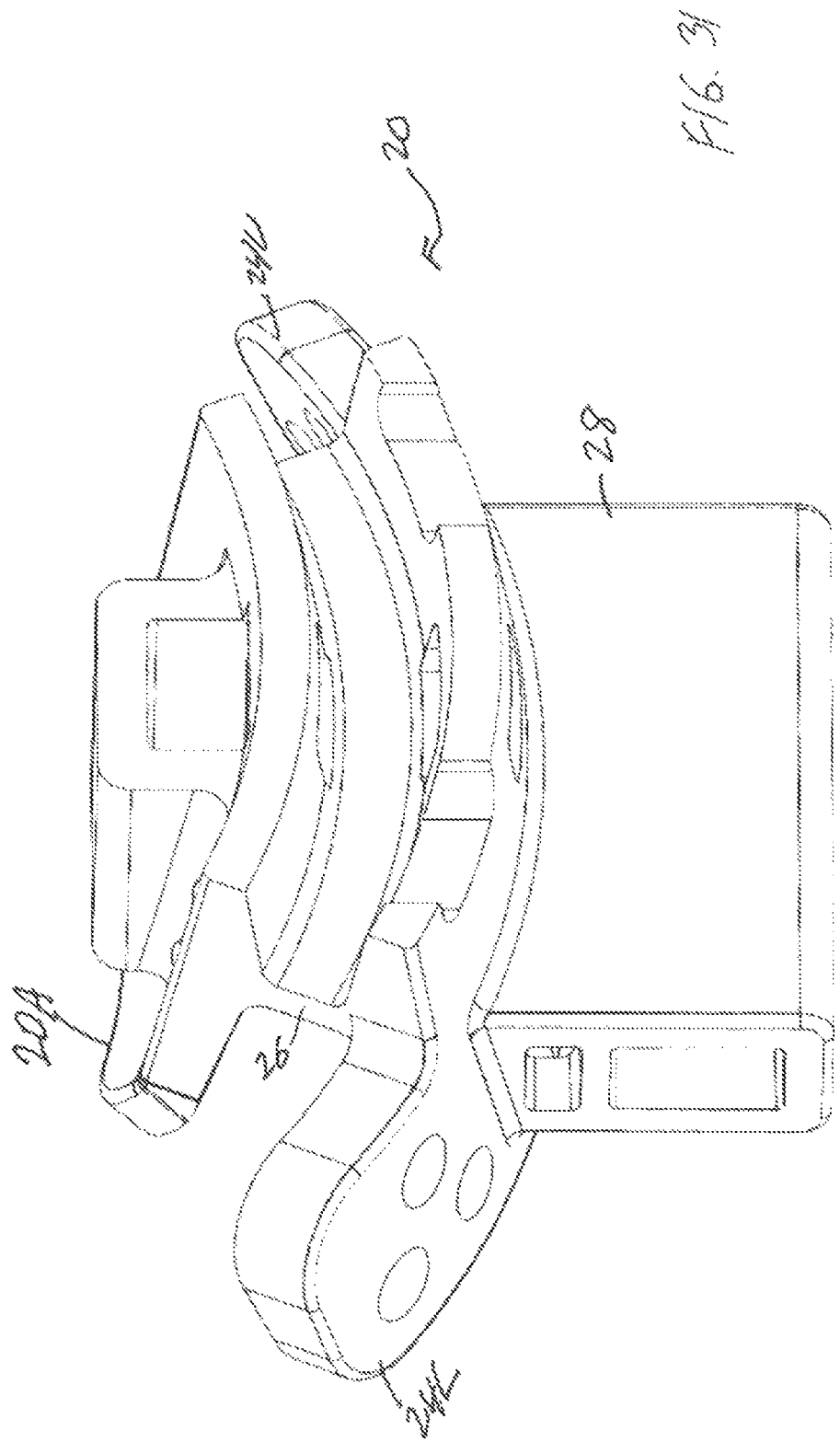

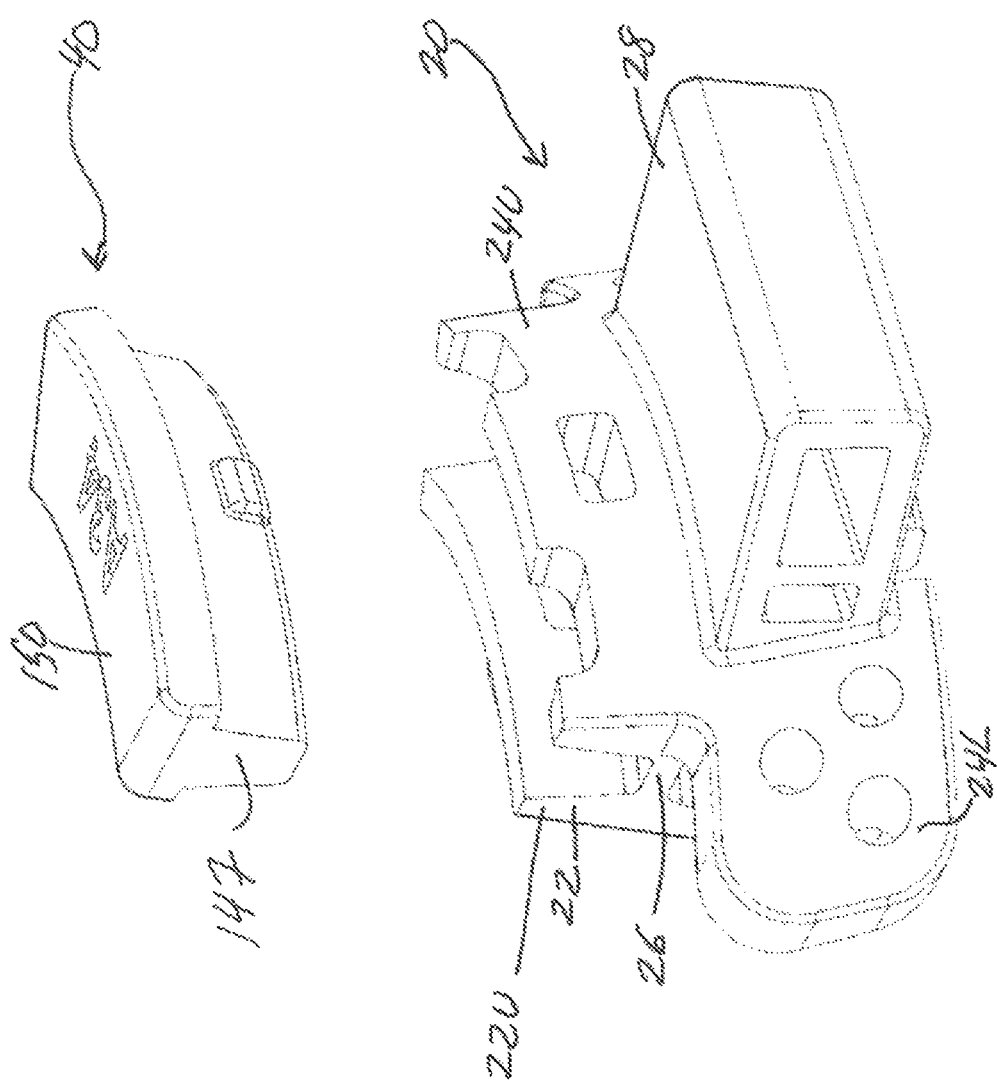

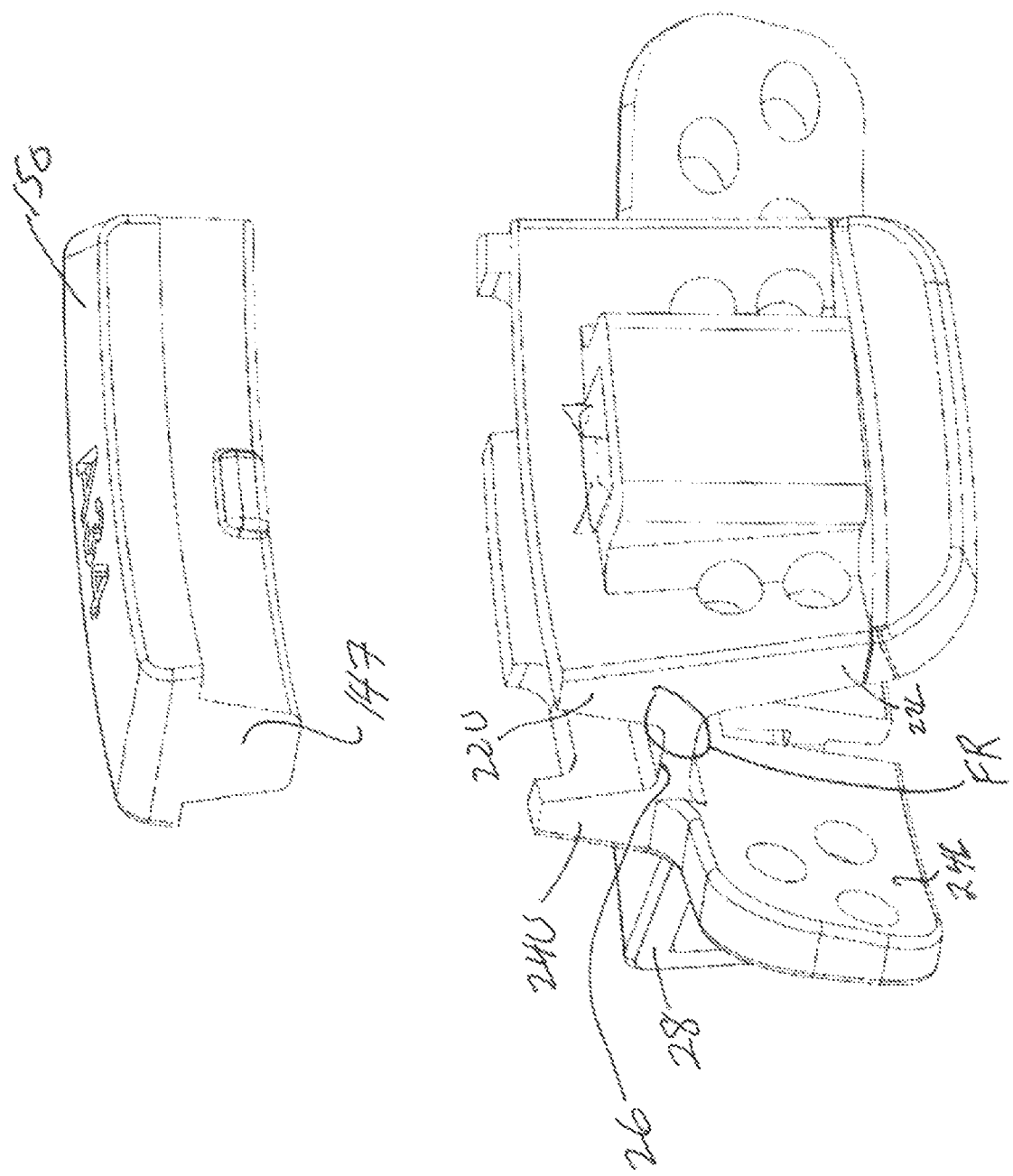

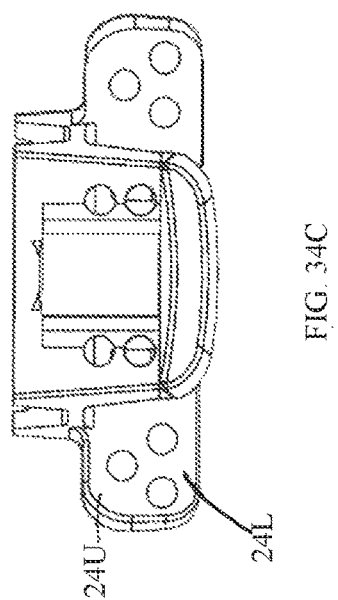
FIG. 34C
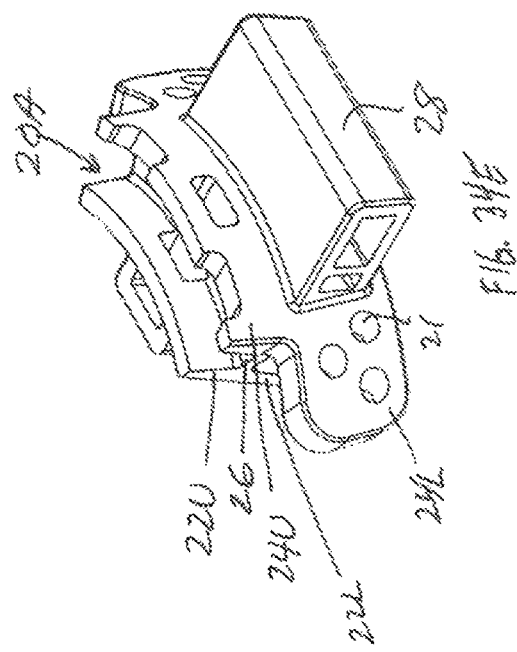
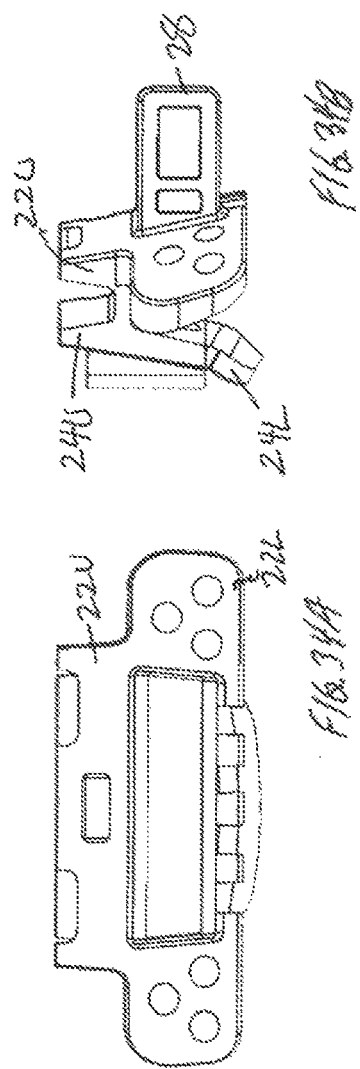
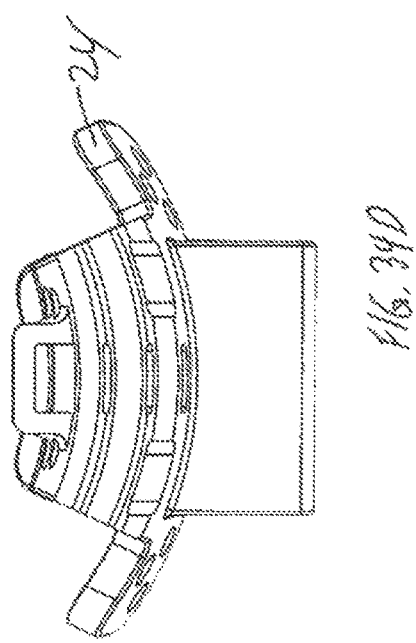

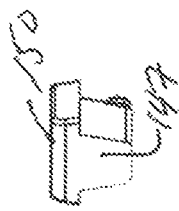

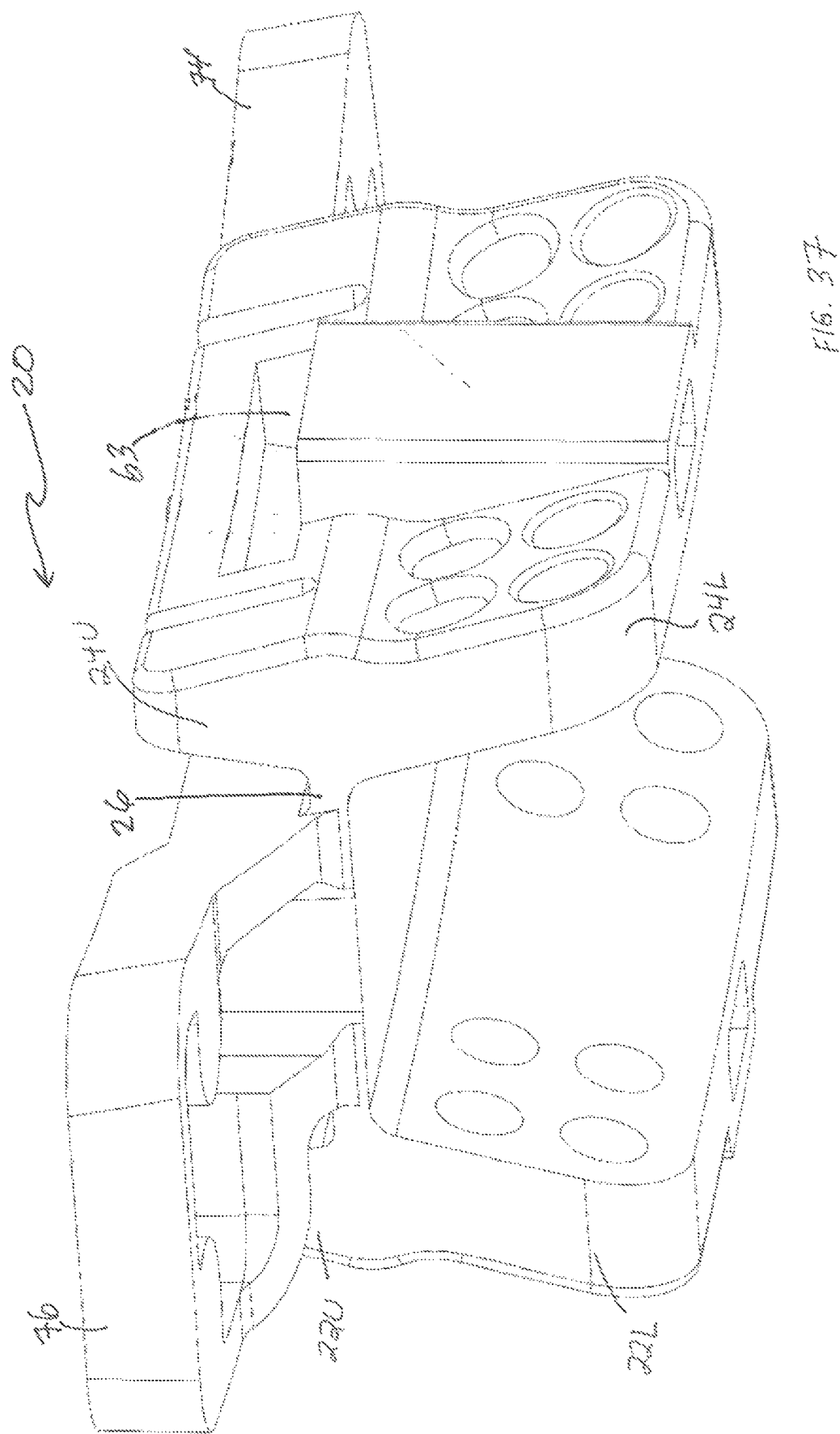

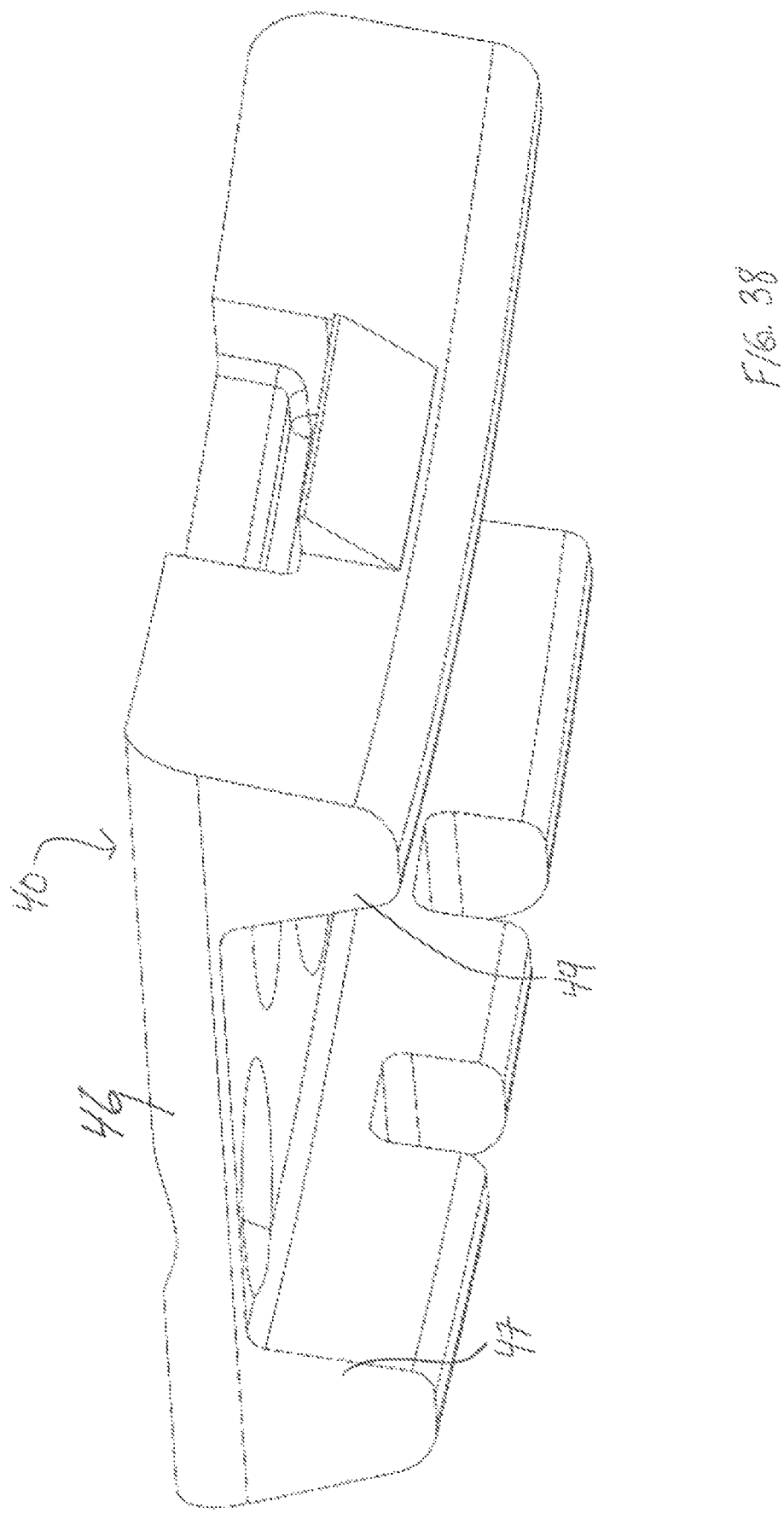

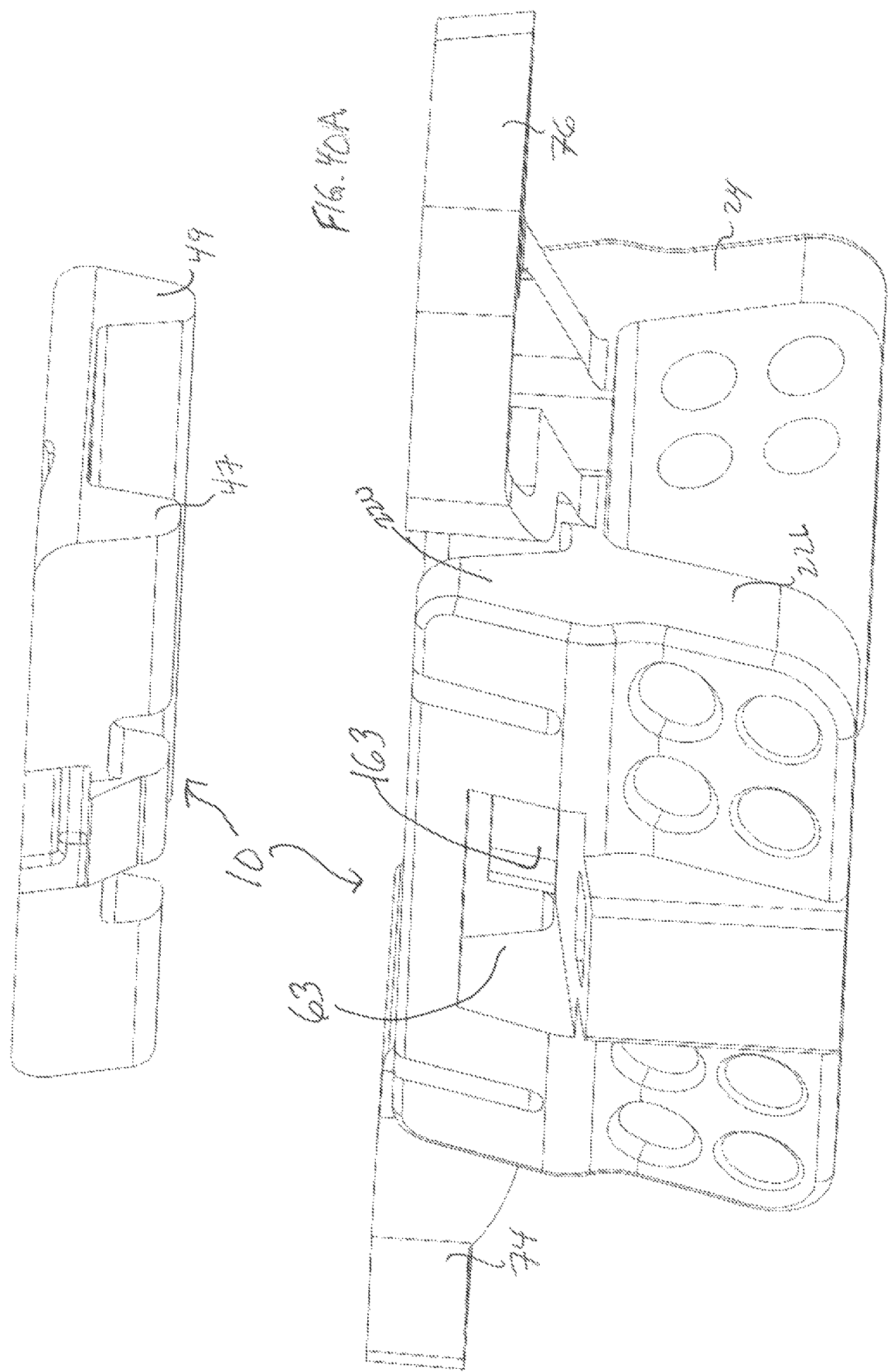

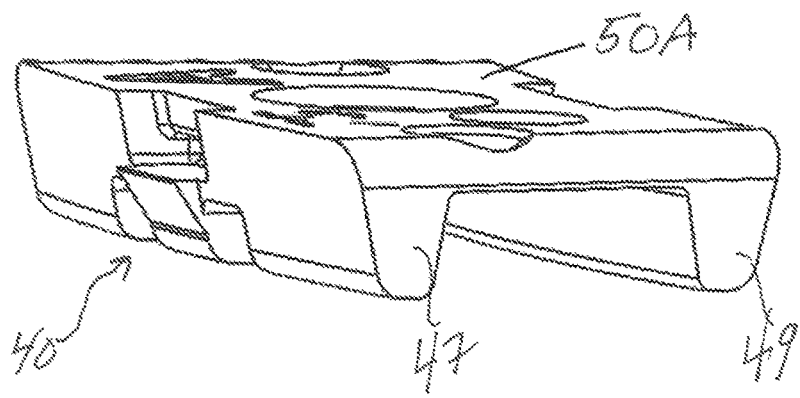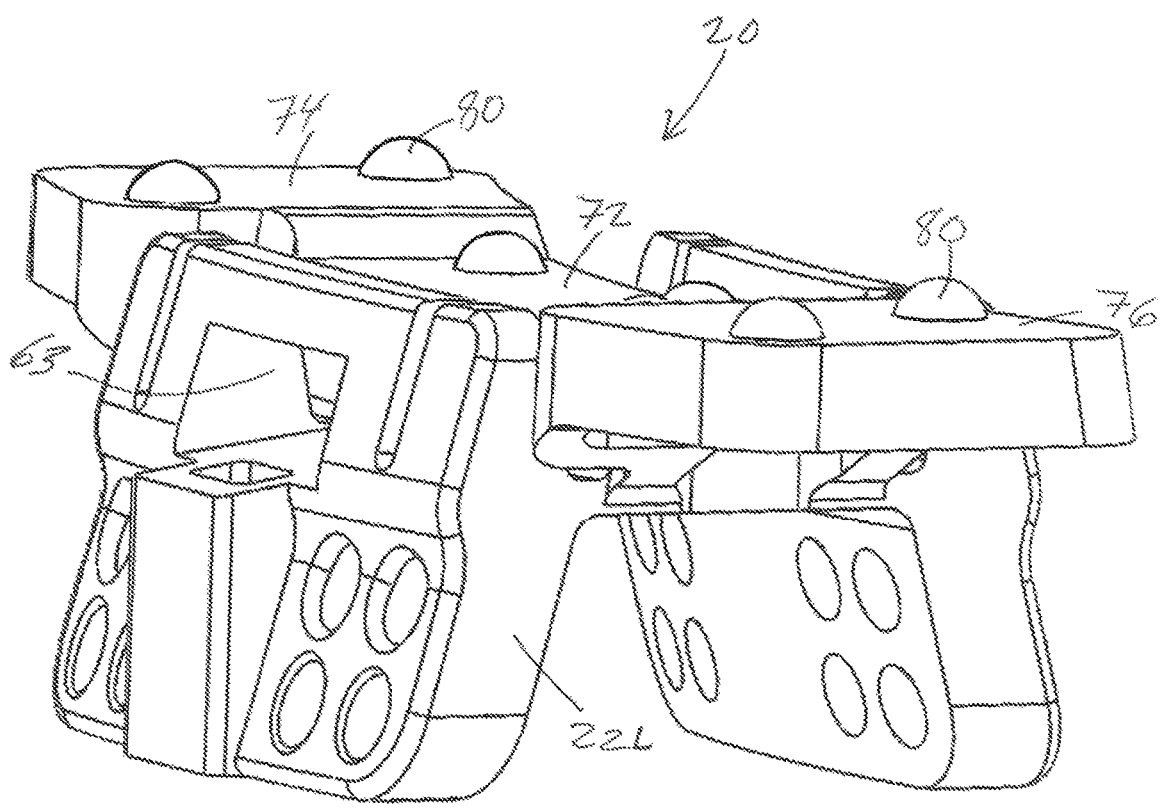
FIG. 40B

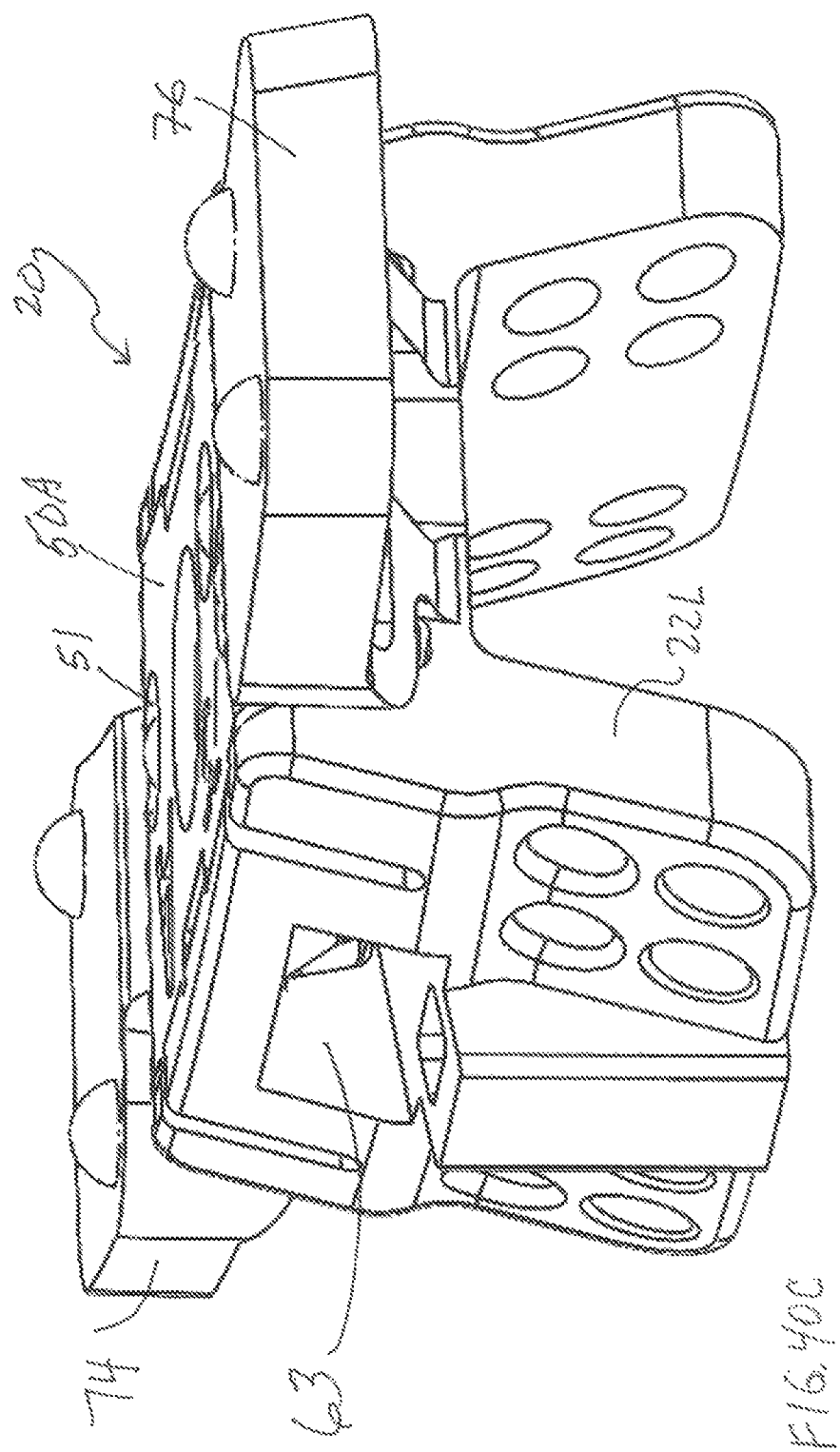

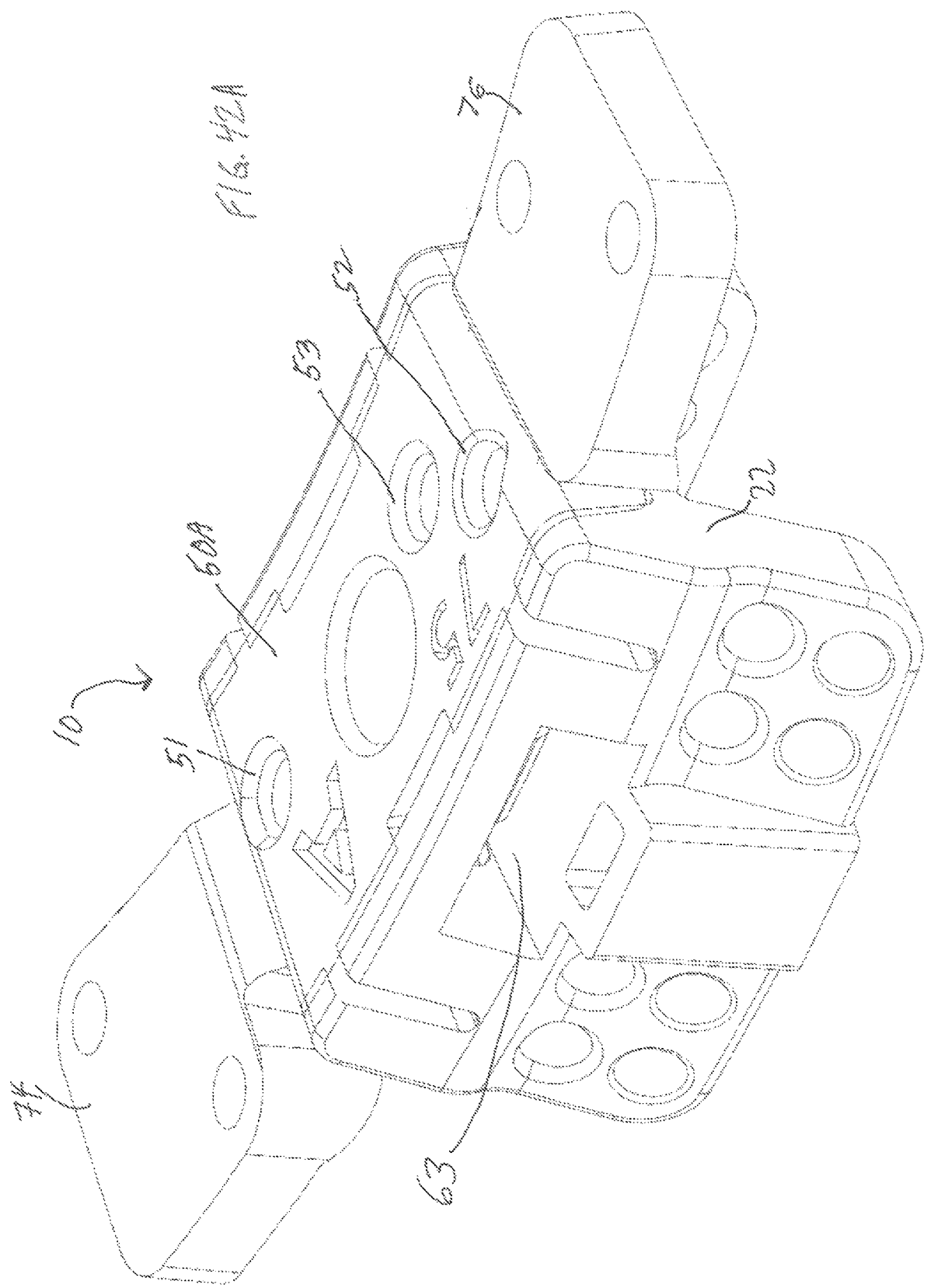

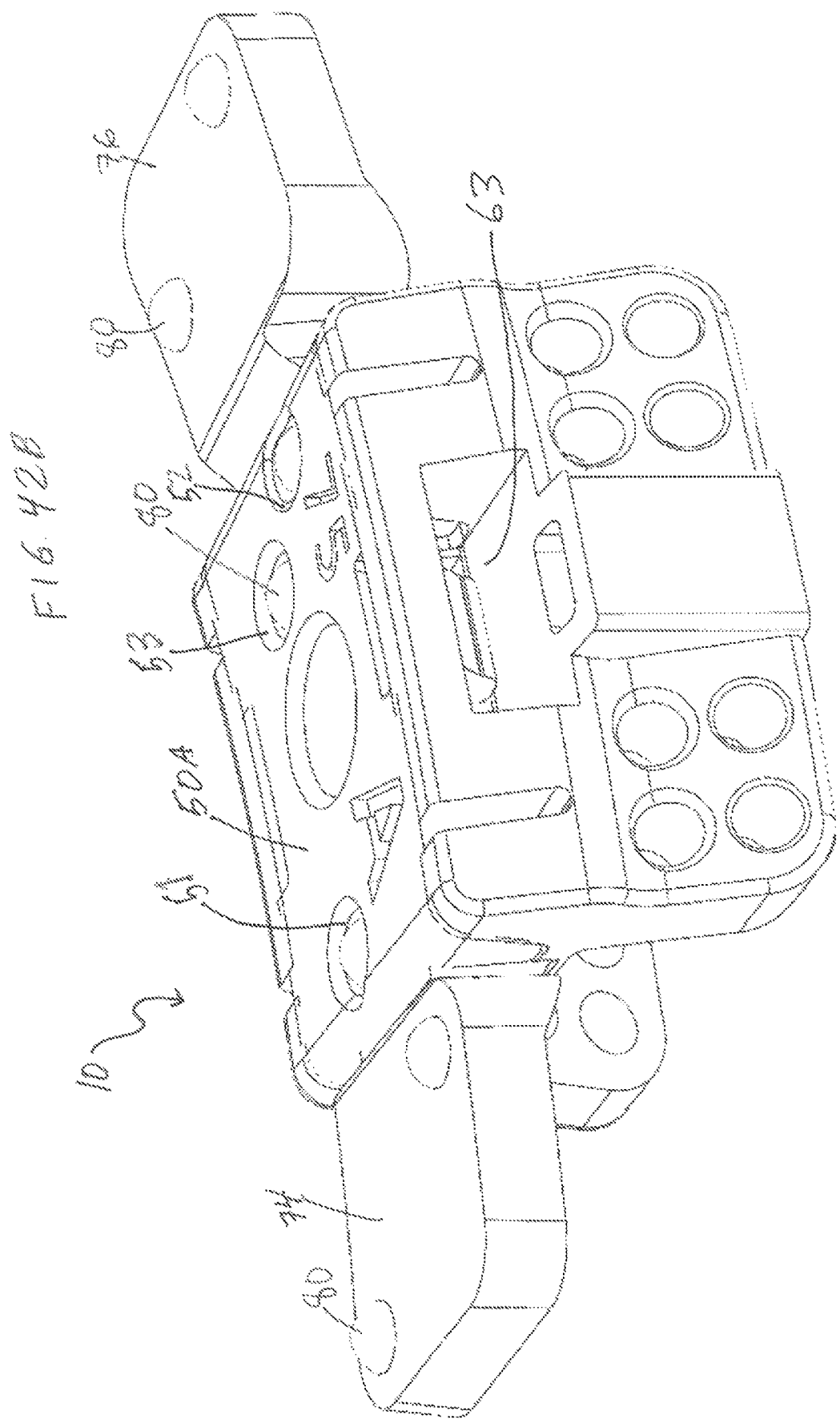

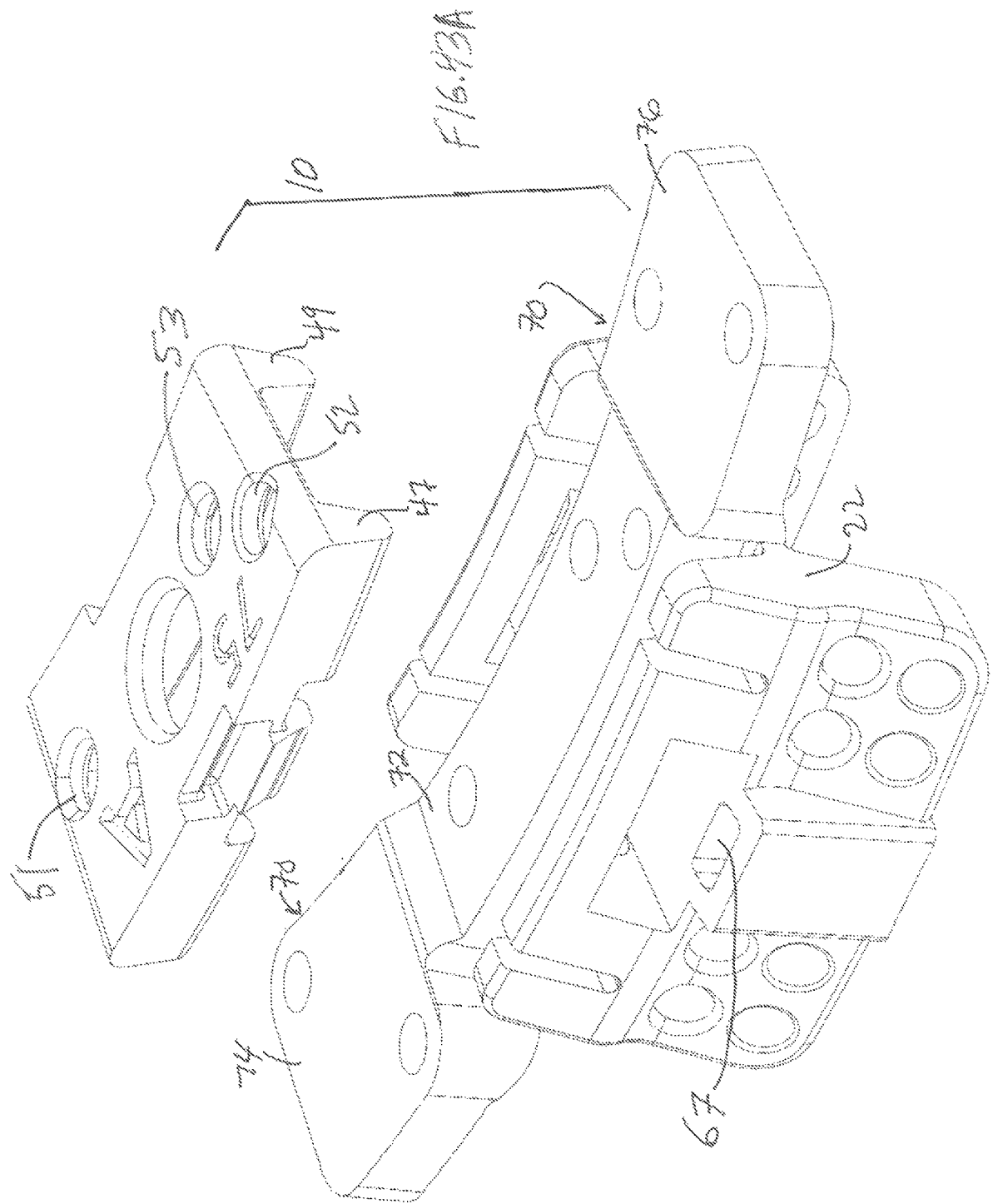

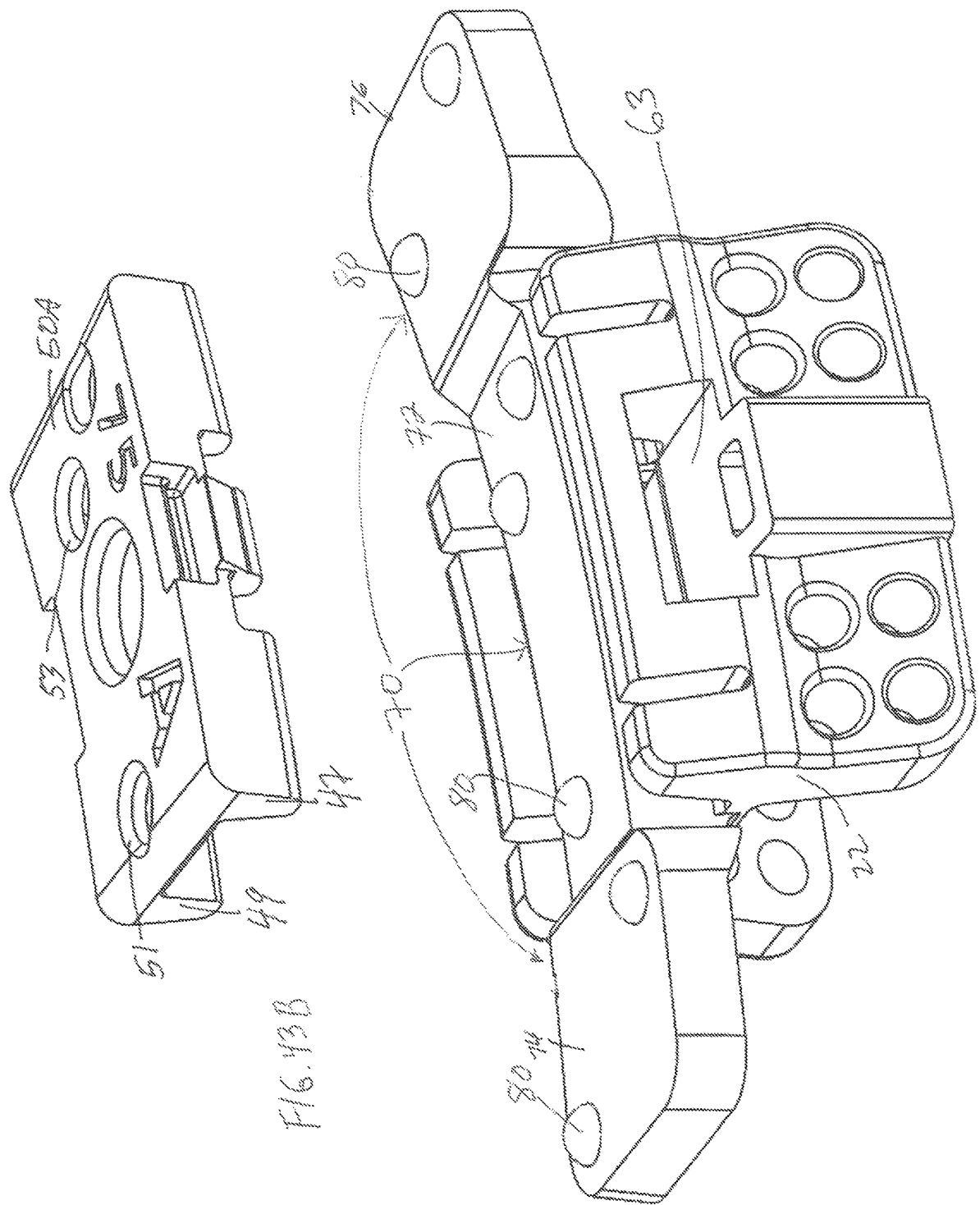

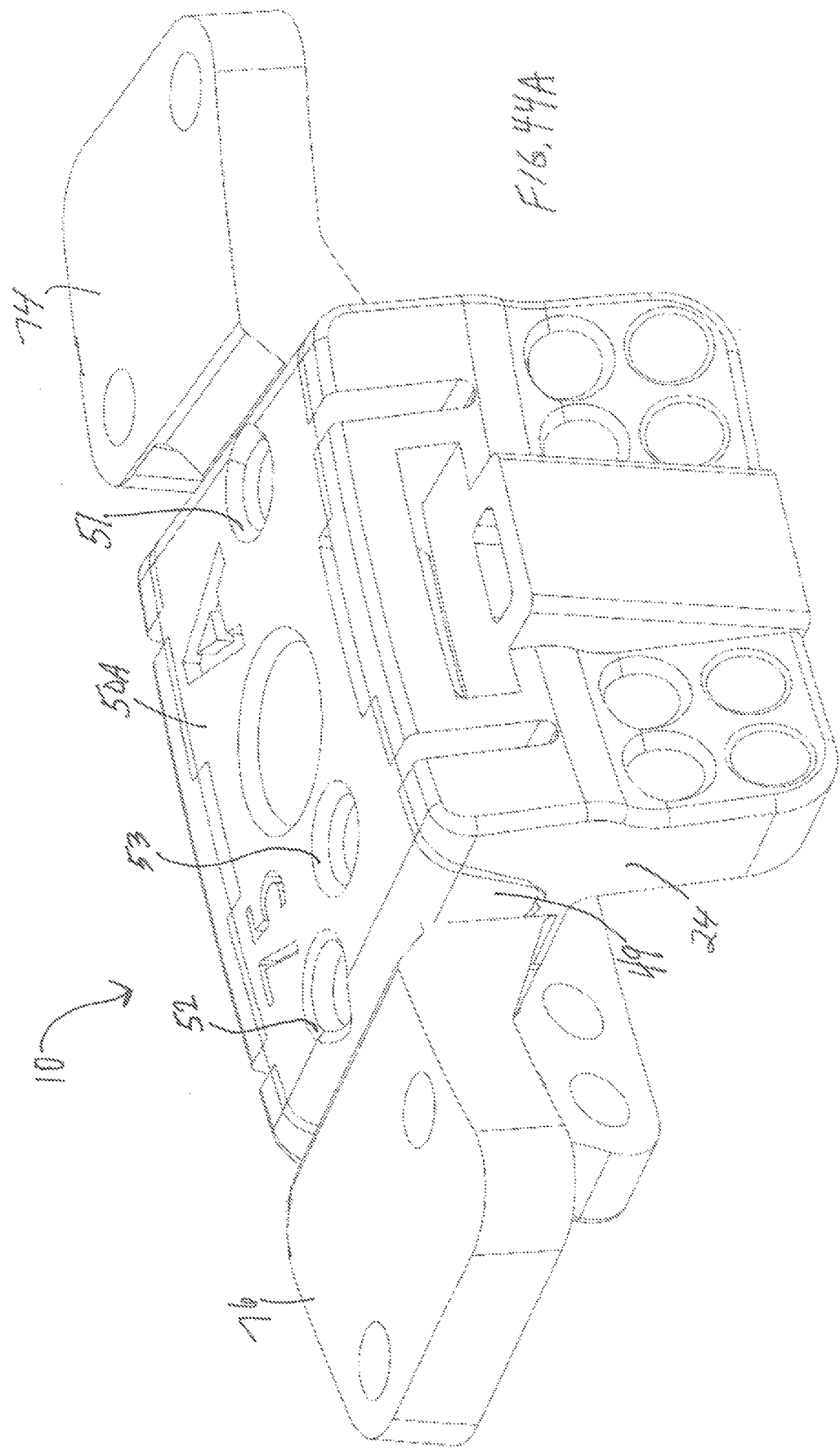

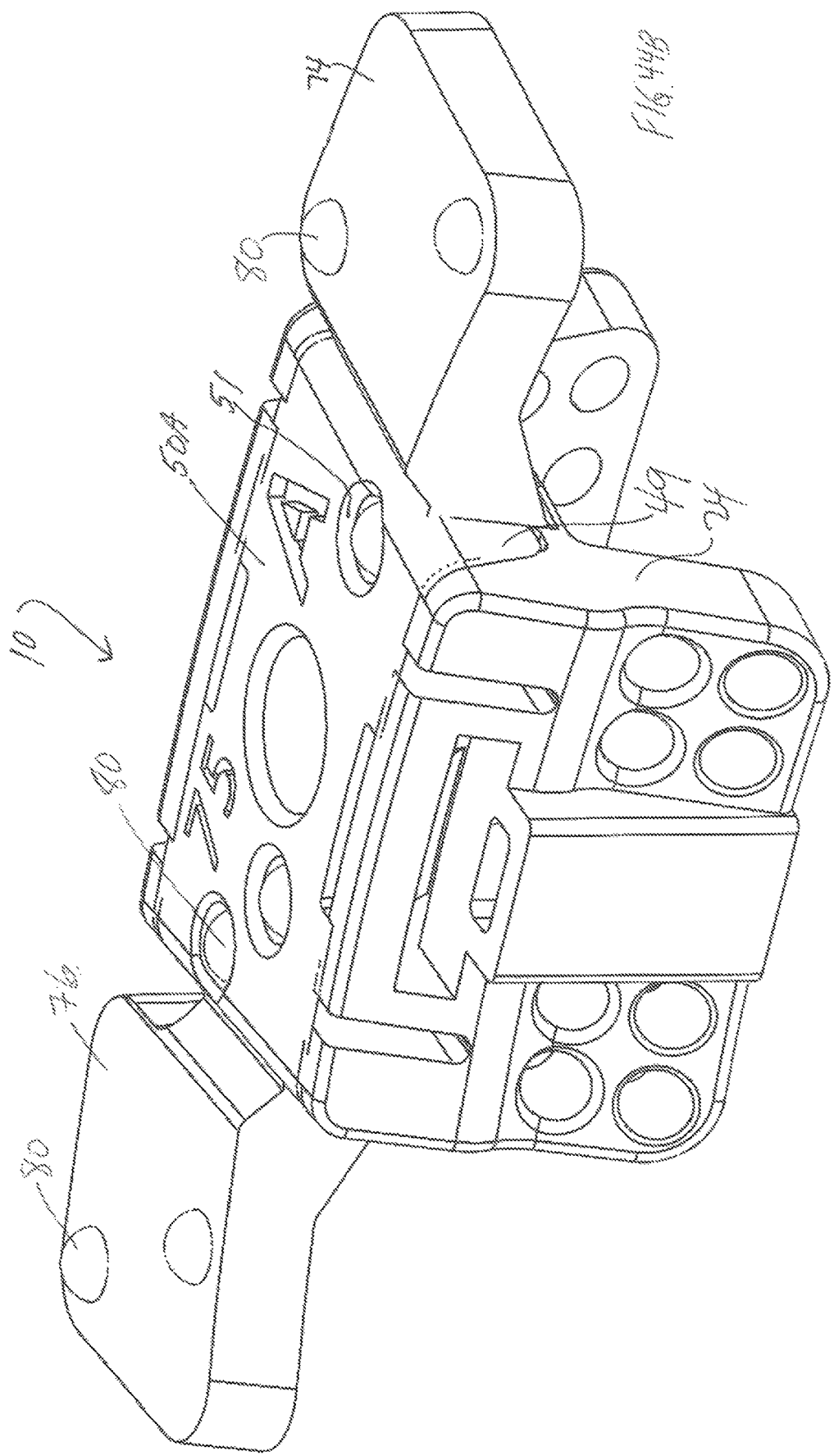

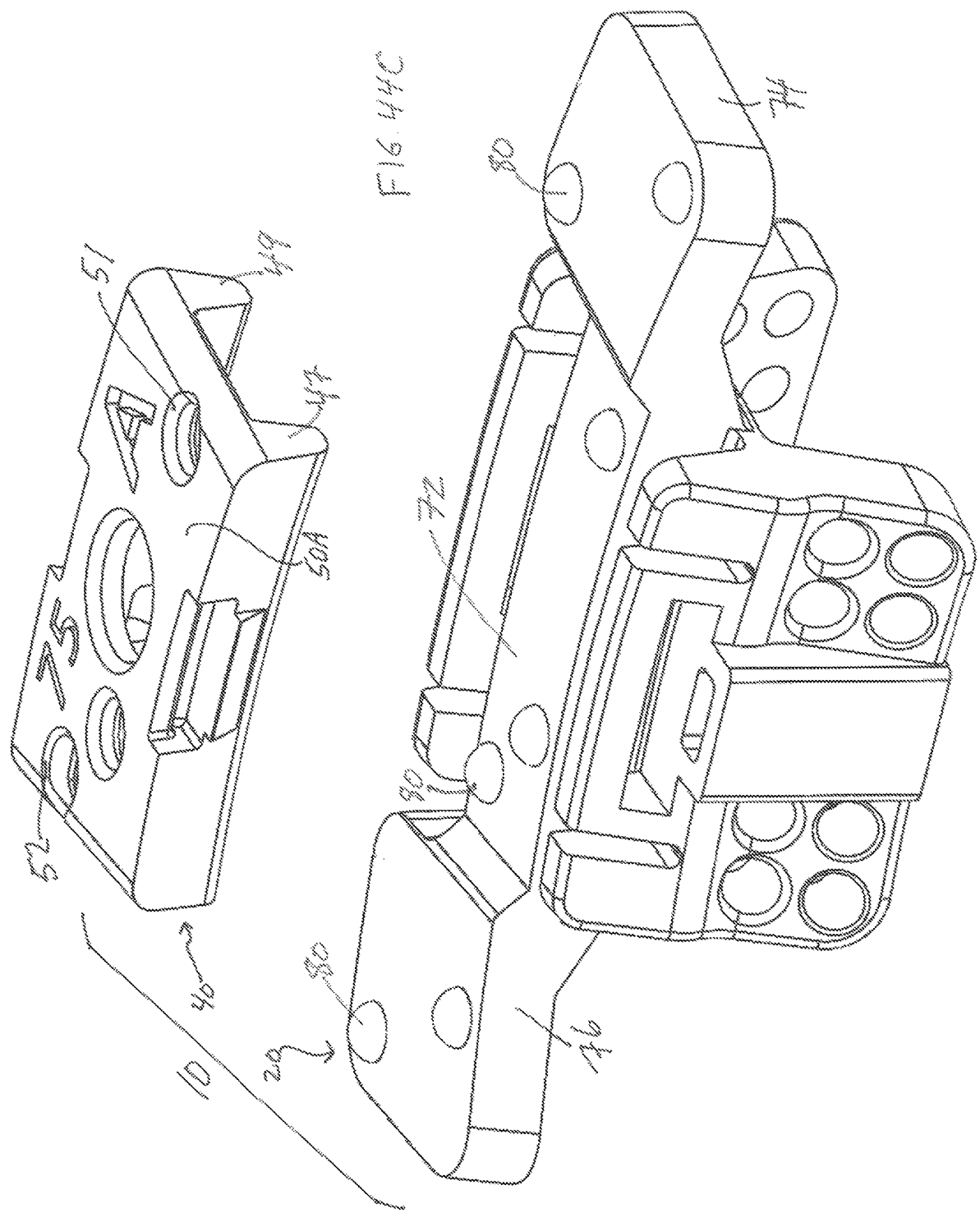

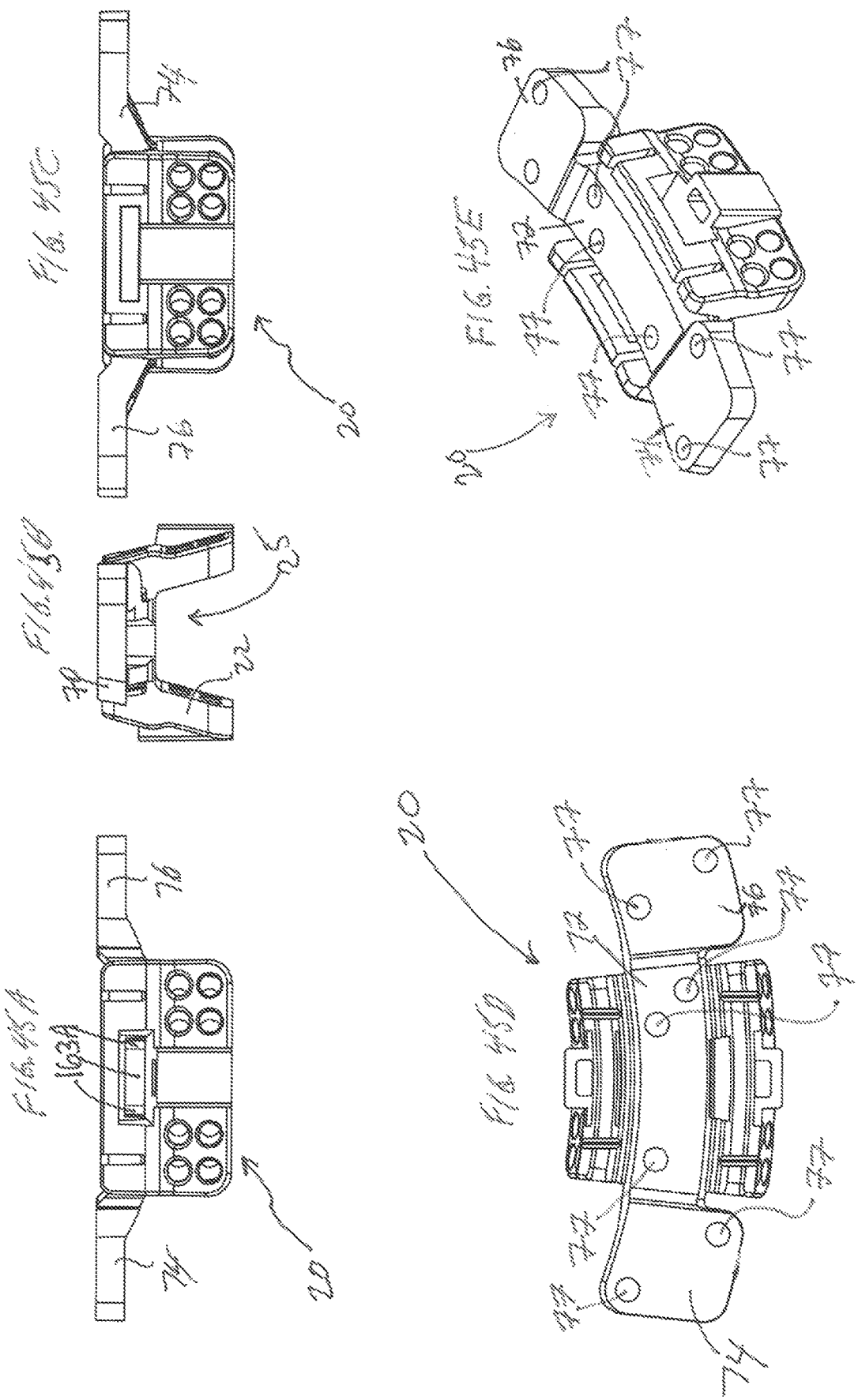

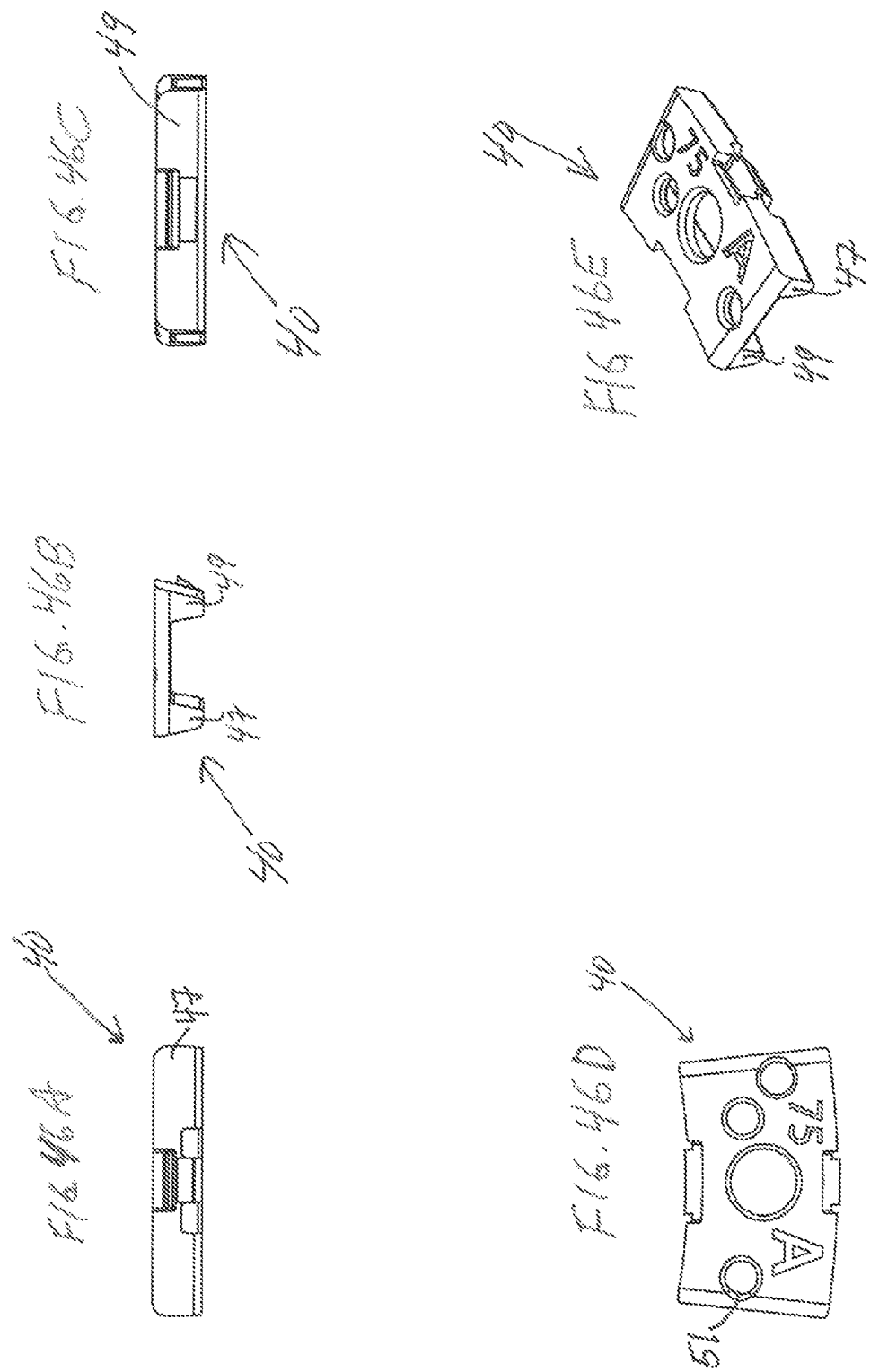

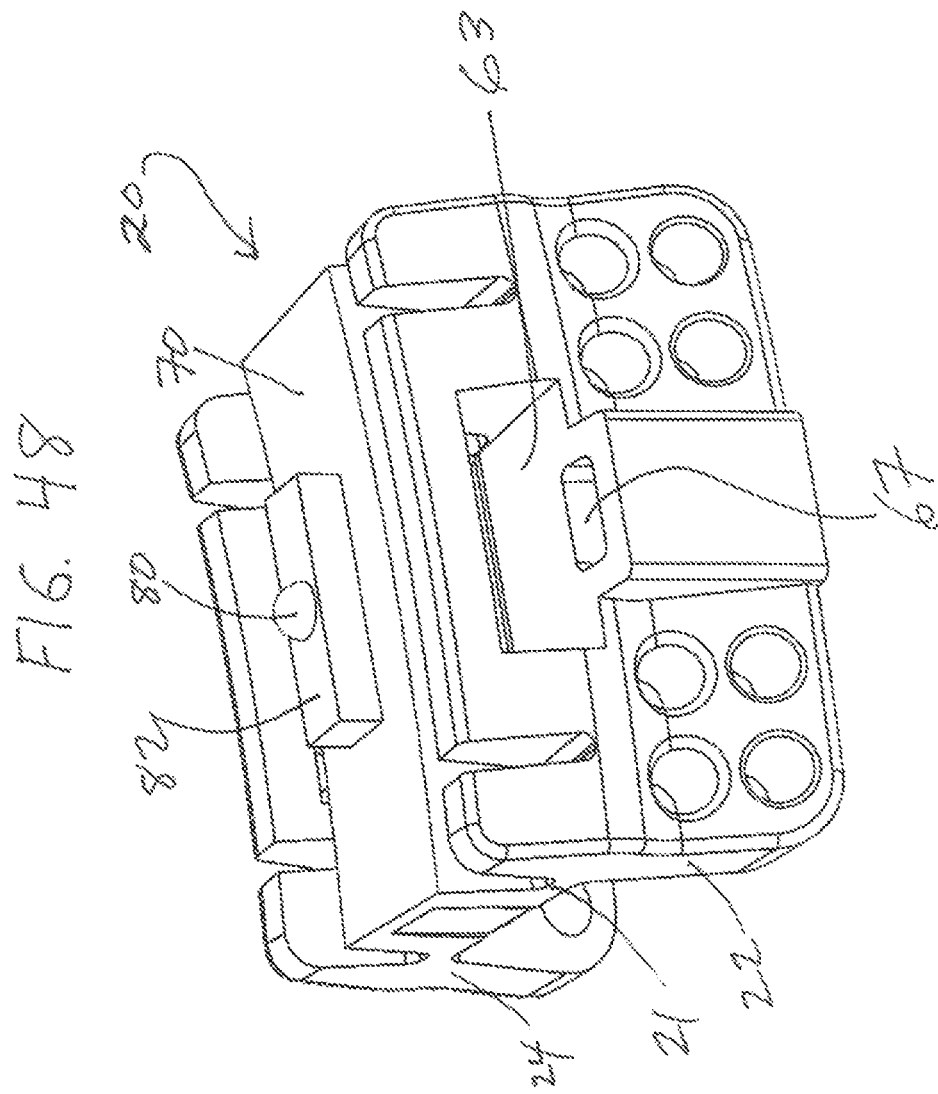

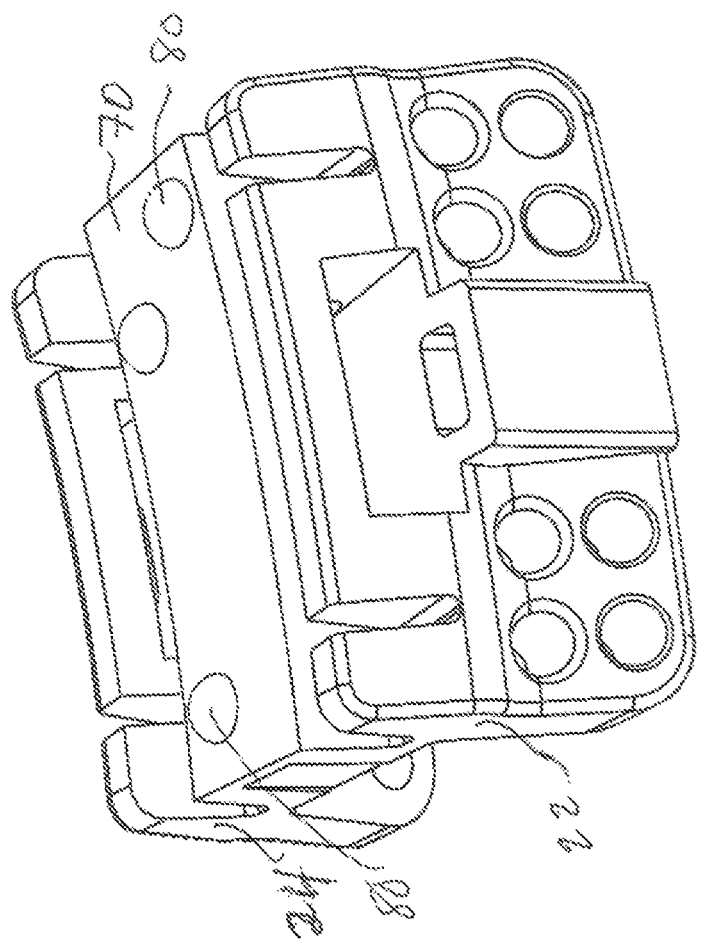

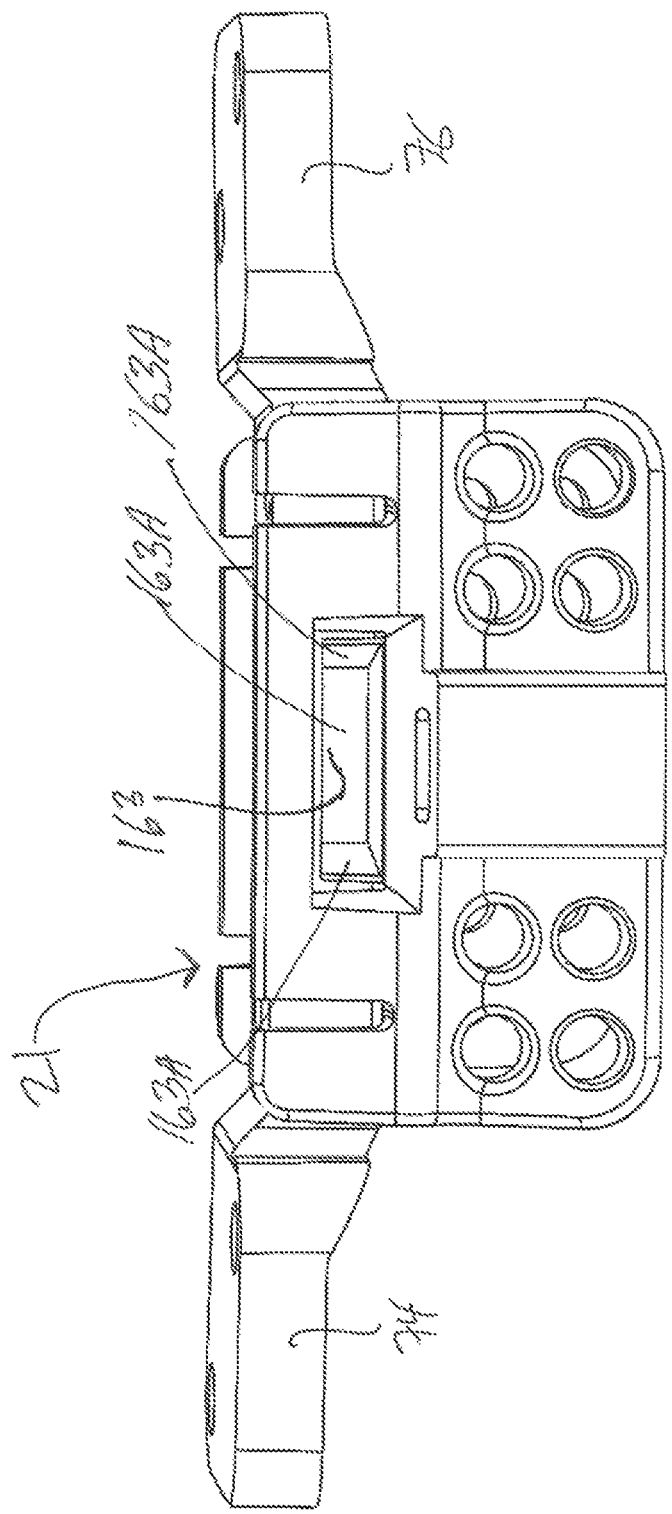

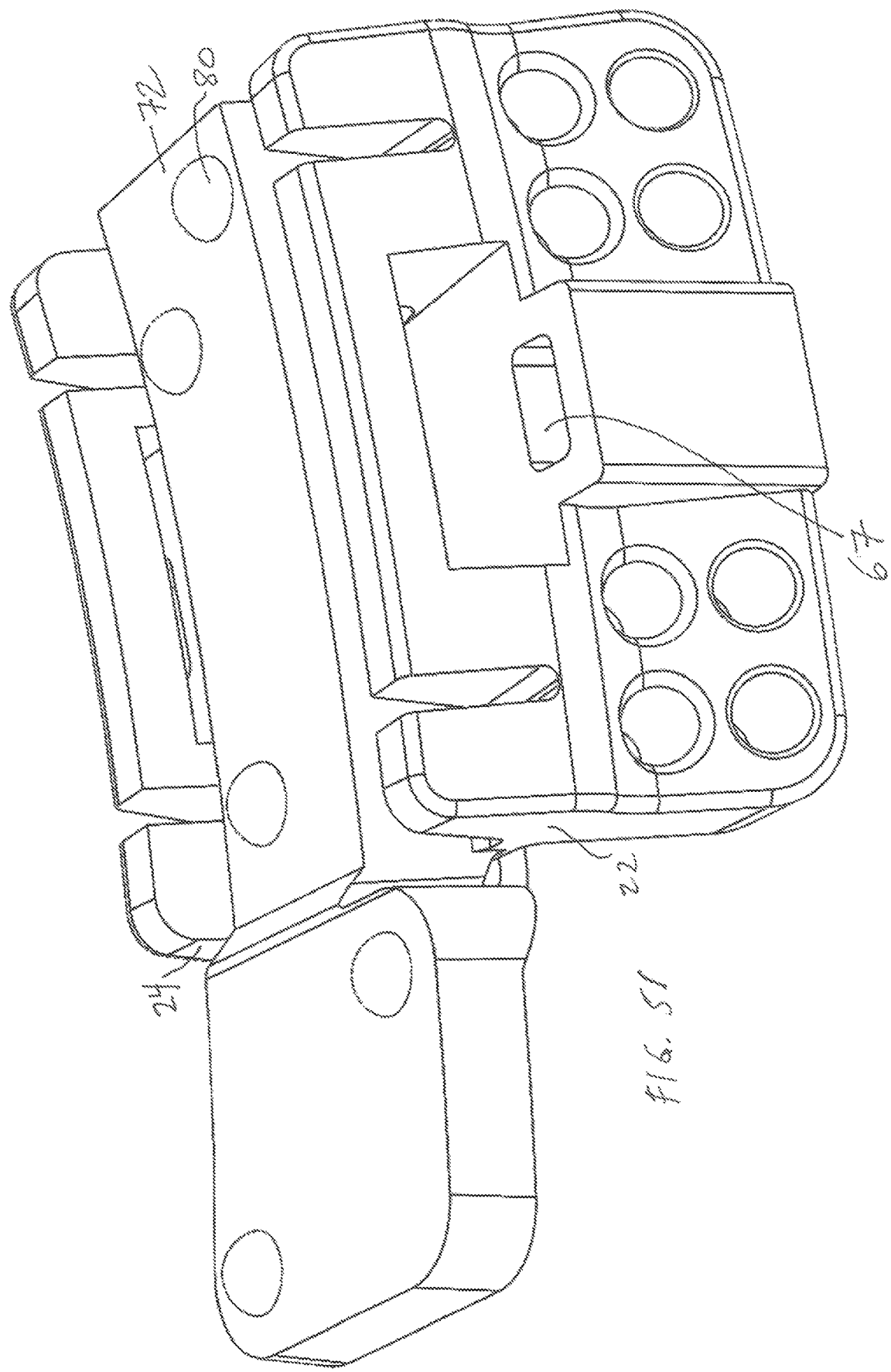

STABLE WINGED AFFIXATION SYSTEM FOR GUIDED DENTAL IMPLANTATION

FIELD AND BACKGROUND OF THE INVENTION

The invention relates to affixation systems and more particularly to affixation systems for guided dental implantation surgery including a fixation tray configured to house a hardening material and including a lock.

Dental implants are used in cases where natural teeth are missing or have to be extracted. Dental implantation surgery involves drilling a hole and enlarging it to a specific size in the maxilla or mandible (upper or lower jaw bone) and then screwing in an implant, a screw-like object into the jaw. After the implant surgery, an abutment and crown are then placed.

The correct and accurate placement of the implant is very important for various reasons. There are anatomical structures which one does not want to drill into such as the inferior alveolar and mental nerves, maxillary sinuses or perforating bone. In addition, one does not want to drill into a tooth root or another implant. It is not easy to accurately position the implant "blindly" (only seeing the original access opening) around 8-13 mm deep into bone. Ideally, implants should be placed in a position and orientation so as to have biting forces in the long axis of the tooth. Improper placement might prevent achieving this Implants should be placed so as to leave a minimum of 2 mm of bone to prevent bone resorption. There is also an aesthetic component for the placement of implants especially in the anterior of the mouth, where the final aesthetic result is affected by the precise placement of the implant.

Originally, the only way to perform any surgery in general was freehand, without any guidance relating to the anatomical structures which one may encounter during surgery. In order to compensate for this, surgical access openings had to be large enough to allow visual verification. Laparoscopy as well as other guides has helped with this aspect in many types of surgeries.

In dentistry, utilizing guided dental surgery helps the surgeon follow the preplanned treatment plan. It makes the surgery minimally invasive, which reduces the risk of tissue damage and facilitates achieving the precision needed. Guided surgery is therefore a preferred approach for dental implant surgery.

During dental and certain other kinds of guided surgery there is a need for real-time computerized measurement of spatial position and orientation of specially marked objects, such as surgical instruments and implants to be implanted in pre-planned positions. The orientation and location of the surgical instruments is monitored by position sensors and the real-time location of the instruments can be displayed on previously acquired patient image data. The orientation and location of the patient is also typically tracked separately, to allow for sensing of anatomy movement relative to the tracked instruments during the operation. In dental surgery and in certain other surgeries, the various orientations and locations of the tracked objects need to be determined with great precision—in the case of dental surgery typically within an accuracy of less than a quarter of a millimeter.

SUMMARY OF THE INVENTION

One aspect is a stable affixation system for guided dental implantation, comprising a fixation tray customizable to the patient including a housing that defines a chamber configured to house a flowable or malleable material and be placed over one or a plurality of teeth of a person during the guided dental implantation, a lock configured, when positioned on the fixation tray, to reduce or eliminate a freedom of movement of the fixation tray, the housing including a central portion that is not configured to flex and having side walls, each side wall having an upper side portion configured to flex when the lock is not positioned on the fixation tray and a lower side portion configured to flex when the lock is not positioned on the fixation tray, the central portion including a body, a first wing extending outward from a first end of the body and a second wing extending outward from a second end of the body so that each of the wings extends an overall length of the housing, the central portion having carved into a surface thereof one or a plurality of recesses shaped for receiving and fixedly holding one or a plurality of registration elements.

In some embodiments, the stable affixation system further comprises the one or plurality of the registration elements fixedly held respectively in the one or plurality of the recesses such that the registration elements are visible on an image of the fixation tray obtained using a dental imaging process and immobile relative to the housing of the fixation tray and such that a position and orientation of the registration elements can be determined in a tracking coordinate system.

In some embodiments, a top surface of the lock has apertures so that when the lock is positioned on the fixation tray the apertures of the lock allow any of the registration elements that are embedded in the fixation tray to remain fixed position.

In some embodiments, the body, the first wing and the second wing each include at least one of the registration elements.

In some embodiments, the body, the first wing and the second wing each include at least two of the registration elements.

In some embodiments, each of the wings includes at least one of the registration elements.

In some embodiments, the second wing is configured to be separated from the body by breaking or by cutting.

In some embodiments, the wings are elevated relative to the body of the central portion along a height dimension of the housing.

In some embodiments, the one or a plurality of registration elements are substantially spherical.

In some embodiments, each of the recesses is shaped for receiving and fixedly holding the one or a plurality of registration elements such that the one or a plurality of registration elements remains at least partially exposed.

In some embodiments, without the lock positioned on the fixation tray, a squeezing force on the upper side portions flexes the lower side portions outward.

In some embodiments, the affixation system further comprises a pole and wherein a side of the central portion has an opening for attaching to part of the pole, the pole also configured to connect to a patient tracker.

Another aspect is a fixation tray configured to be used in a stable affixation system for guided dental implantation, the fixation tray comprising the fixation tray customizable to the patient and including a housing that defines a chamber configured to house a flowable or malleable material and be placed over one or a plurality of teeth of a person during the guided dental implantation, the housing including a central portion that is not configured to flex and having side walls, each side wall having an upper side portion configured to flex and a lower side portion configured to flex, the central portion including a body, a first wing extending outward from a first end of the body and a second wing extending outward from a second end of the body so that each of the wings extend an overall length of the housing, the central portion having carved into a surface thereof one or a plurality of recesses shaped for receiving and fixedly holding one or a plurality of registration elements.

In some embodiments, the affixation system further comprises the one or plurality of the registration elements fixedly held respectively the one or plurality of the recesses such that the one or a plurality of registration elements are each at least partially exposed, said one or a plurality of registration elements configured to be visible on an image of the fixation tray obtained using a dental imaging process and immobile relative to the housing of the fixation tray.

In some embodiments, the body, the first wing and the second wing each include at least one of the one or a plurality of registration elements.

In some embodiments, the body, the first wing and the second wing each include at least two of the one or a plurality of registration elements.

In some embodiments, each of the wings includes at least one of the one or a plurality of registration elements.

In some embodiments, when the fixation tray is placed on the one or the plurality of teeth, the central portion is immobile with respect to the one or the plurality of teeth if either the lock is positioned on the fixation tray or if the flowable or malleable material has hardened against the one or the plurality of teeth.

In some embodiments, a position and orientation of the one or a plurality of registration elements is configured to be localized in a tracking coordinate system during a registration step of the guided dental implantation.

In some embodiments, the wings are elevated relative to the body of the central portion along a height dimension of the housing.

In some embodiments, the one or a plurality of registration elements are substantially spherical.

In some embodiments, a squeezing force on the upper side portions flexes the lower side portions outward when the tray is not limited by an external lock of the system.

In some embodiments, a side of the central portion is configured to attach to a pole that connects to a patient tracker.

In some embodiments, each of the recesses is configured to hold the respective one or a plurality of registration elements such that the one or a plurality of registration elements are able to be localized in a tracking coordinate system.

A still aspect is a stable affixation system for guided dental implantation, comprising a fixation tray customizable to the patient including a housing that defines a chamber configured to house a flowable or malleable material and be placed over one or a plurality of teeth of a person during the guided dental implantation, a lock configured, when positioned on the fixation tray, to reduce or eliminate a freedom of movement of the fixation tray, the housing including a central portion that is not configured to flex and having side walls, each side wall having an upper side portion configured to flex when the lock is not positioned on the fixation tray and a lower side portion configured to flex when the lock is not positioned on the fixation tray, wherein when the lock is not positioned on the fixation tray a squeezing force on the upper side portions flexes the lower side portions outward, one of the side walls having a cavity on the upper portion thereof for passage of an attachment element, a side of the central portion having a central portion cavity for receipt of the attachment element such that once received the attachment element is affixed to the central portion in an immobile manner.

In some embodiments, the stable affixation system further comprises one or a plurality of registration elements either entirely embedded within the central portion or else affixed in a recess on an exposed surface of said central portion.

In some embodiments, the central portion has a surface into which is carved one or a plurality of recesses shaped for receiving and fixedly holding one or a plurality of registration elements.

A yet still further aspect is a fixation tray configured to be used in a stable affixation system for guided dental implantation, the fixation tray comprising the fixation tray customizable to the patient and including a housing that defines a chamber configured to house a flowable or malleable material and be placed over one or a plurality of teeth of a person during the guided dental implantation, the housing including a central portion that is not configured to flex and having side walls, each side wall having an upper side portion configured to flex and a lower side portion configured to flex, wherein a squeezing force on the upper side portions flexes the lower side portions outward, one of the side walls having a cavity on the upper portion thereof for passage of an attachment element, a side of the central portion having a central portion cavity for receipt of the attachment element such that once received the attachment element is affixed to the central portion in an immobile manner.

In some embodiments, the stable affixation system further comprises one or a plurality of registration elements either entirely embedded within the central portion or else affixed in a recess on an exposed surface of said central portion.

In some embodiments, the central portion has a top surface and wherein carved into the top surface is one or a plurality of recesses shaped for receiving and fixedly holding one or a plurality of registration elements.

These and other features, aspects and advantages of the invention will become better understood with reference to the following drawings, descriptions and claims.

BRIEF DESCRIPTION OF THE DRAWINGS

Various embodiments are herein described, by way of example only, with reference to the accompanying drawings, wherein:

FIG. 1 is an exploded view of a stable affixation system for dental implantation together with a pole with a connector to a patient tracking device, in accordance with an embodiment of the invention;

FIG. 2 is an assembled version of the stable affixation system of FIG. 1 together with the tracking device, in accordance with an embodiment of the invention;

FIG. 3A is a view of a first of the arm extensions of the fixation tray of the stable affixation system from a side and an end, in accordance with an embodiment of the invention;

FIG. 3B is a view of a second of the arm extensions of the fixation tray of the stable affixation system from a side, in accordance with an embodiment of the invention;

FIG. 4 is an end view of a fixation tray of the stable affixation system, in accordance with an embodiment of the invention;

FIG. 5 is a top view of a fixation tray of the stable affixation system, in accordance with an embodiment of the invention;

FIG. 6 is a side view of a fixation tray of the stable affixation system, in accordance with an embodiment of the invention;

FIG. 7 is a bottom view of a fixation tray of the stable affixation system, in accordance with an embodiment of the invention;

FIG. 8 is an end view of a locking wedge of the stable affixation system, in accordance with an embodiment of the invention;

FIG. 9 is a top view of a locking wedge of the stable affixation system, in accordance with an embodiment of the invention;

FIG. 10 is a side view of a locking wedge of the stable affixation system, in accordance with an embodiment of the invention;

FIG. 11 is a bottom view of a locking wedge of the stable affixation system, in accordance with an embodiment of the invention;

FIG. 12 is a side view of a pole of or used with the stable affixation system, in accordance with an embodiment of the invention;

FIG. 13 is a sectional view of the pole of FIG. 12 of or used with the stable affixation system, in accordance with an embodiment of the invention;

FIG. 15 is an end view of one version of a fixation tray of the stable affixation system, in accordance with an embodiment of the invention;

FIG. 16 is a flow chart of a method, in accordance with an embodiment of the invention; and FIG. 17 is a flow chart of a method, in accordance with an embodiment of the invention;

FIG. 21 is a flow chart of a method, in accordance with an embodiment of the invention;

FIG. 26B is a perspective view of the fixation tray and lock of FIG. 26A fitted together, in accordance with one embodiment;

FIG. 27A is an exploded view as in FIG. 26A except taken from the front and an opposite end, of the fixation tray and lock of FIG. 26A, in accordance with one embodiment;

FIG. 27B is a perspective view of the fixation tray and lock of FIG. 27A fitted together, in accordance with one embodiment;

FIG. 29A is an end view of a lock, in accordance with one embodiment;

FIG. 29B is a top view of a lock, in accordance with one embodiment;

FIG. 29C is a side view of a lock, in accordance with one embodiment;

FIG. 29D is a perspective view of a lock, in accordance with one embodiment;

FIG. 30 is a bottom view of a fixation tray primarily for anterior teeth, in accordance with one embodiment;

FIG. 31 is a top view of the fixation tray of FIG. 30, in accordance with one embodiment;

FIG. 32A is an exploded front view of fixation tray of FIGS. 30-31, in accordance with one embodiment;

FIG. 33B is a perspective view of the fixation tray and lock of FIG. 33A fitted together, in accordance with one embodiment;

FIG. 34A is a side view of a fixation tray primarily for anterior teeth, in accordance with one embodiment;

FIG. 34B is an end view from the side of a fixation tray primarily for anterior teeth, in accordance with one embodiment;

FIG. 34C is a side view of a fixation tray primarily for anterior teeth, in accordance with one embodiment;

FIG. 34D is a top view of a fixation tray primarily for anterior teeth, in accordance with one embodiment;

FIG. 34E is a perspective view of a fixation tray primarily for anterior teeth, in accordance with one embodiment;

FIG. 35A is a side view of a lock, in accordance with one embodiment;

FIG. 35B is an end view from the side of a lock, in accordance with one embodiment;

FIG. 35C is a side view of a lock, in accordance with one embodiment;

FIG. 35D is a top view of a lock, in accordance one embodiment;

FIG. 35E is a perspective view of a lock, in accordance with one embodiment.

FIG. 37 is a perspective view from an end and front of a winged fixation tray primarily for posterior teeth, in accordance with one embodiment;

FIG. 38 is a perspective view of a lock for the winged fixation tray of FIG. 37 from below, in accordance with one embodiment;

FIG. 40A is another exploded view of the winged fixation tray of FIG. 37 and lock of FIG. 38 from an end and side, in accordance with one embodiment;

FIG. 40B is an exploded view from an end and side similar to FIG. 40A except from a slightly different angle and including the fiducial members, in accordance with one embodiment;

FIG. 40C is an integrated view of the winged fixation tray and lock, including the fiducial members, from the view shown in FIG. 40B, in accordance with one embodiment;

FIG. 42A is a view of the winged fixation tray of FIG. 37 and lock of FIG. 38 from the top and left side, in accordance with an embodiment;

FIG. 42B is a view of the winged fixation tray of FIG. 37 and lock of FIG. 38 similar to FIG. 42A but from a slightly different angle and including the fiducial members, in accordance with an embodiment;

FIG. 43A is an exploded view of the winged fixation tray and lock shown in FIG. 42A in accordance with an embodiment;

FIG. 43B is an exploded view of the winged fixation tray and lock shown in FIG. 42A (from a slightly different angle than FIG. 43A) including the fiducial members in accordance with an embodiment;

FIG. 44A is a view of the winged fixation tray of FIG. 37 and lock of FIG. 38 from the top and right side, in accordance with an embodiment;

FIG. 44B is a view of the winged fixation tray of FIG. 37 and lock of FIG. 38 from the top and right side as in FIG. 44A but from a slightly different angle and including fiducial members, in accordance with an embodiment;

FIG. 44C is an exploded view of the winged fixation tray and lock of FIG. 44B, in accordance with an embodiment;

FIG. 45A is a side view of a winged fixation tray, in accordance with an embodiment;

FIG. 45B is a front view of a winged fixation tray, in accordance with an embodiment;

FIG. 45C is a side view of a winged fixation tray, in accordance with an embodiment;

FIG. 45D is a top view of a winged fixation tray, in accordance with an embodiment;

FIG. 45E is a perspective view of a winged fixation tray, in accordance with an embodiment;

FIG. 46A is a side view of a lock for a winged fixation tray, in accordance with an embodiment;

FIG. 46B is a front view of a lock for a winged fixation tray, in accordance with an embodiment;

FIG. 46C is a side view of a lock for a winged fixation tray, in accordance with an embodiment;

FIG. 46D is a top view of a lock for a winged fixation tray, in accordance with an embodiment;

FIG. 46E is a perspective view of a lock for a winged fixation tray, in accordance with an embodiment;

FIG. 48 is a view from the side and top of a fixation tray without wings and showing a removable attachment element that features a fiducial member, in accordance with one embodiment;

FIG. 49 is a view from the side and top of a fixation tray without wings and showing fiducial members embedded on a central portion of its housing, in accordance with one embodiment;

FIG. 50 is a side view generally similar to FIG. 45A except seen slightly from above and is enlarged, in accordance with one embodiment; and FIG. 51 is a view similar to FIG. 49 except with one wing.

DETAILED DESCRIPTION OF THE INVENTION

Figure 14B:
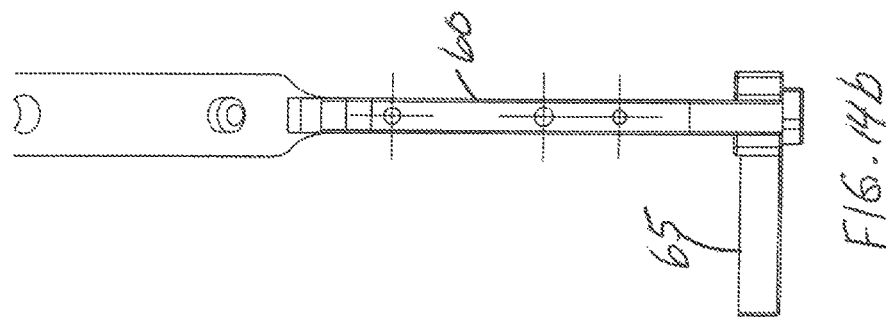
FIG. 14B is a front view of a tracking device and handle for the stable affixation system, in accordance with an embodiment of the invention.
Figure 14A:
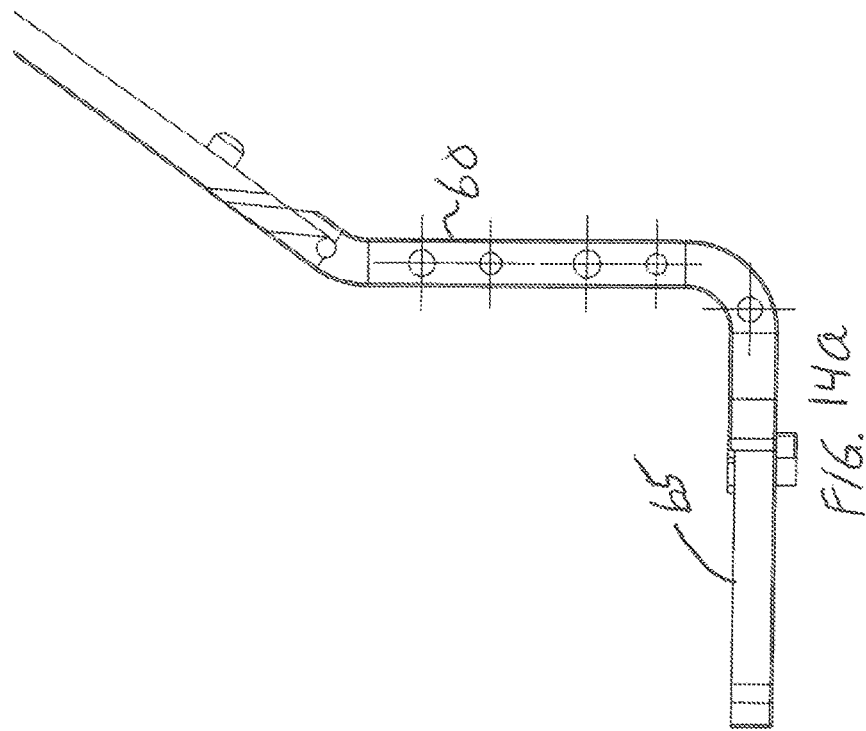
FIG. 14A is a side view of a tracking device and handle for the stable affixation system, in accordance with an embodiment of the invention.
Figure 14C:
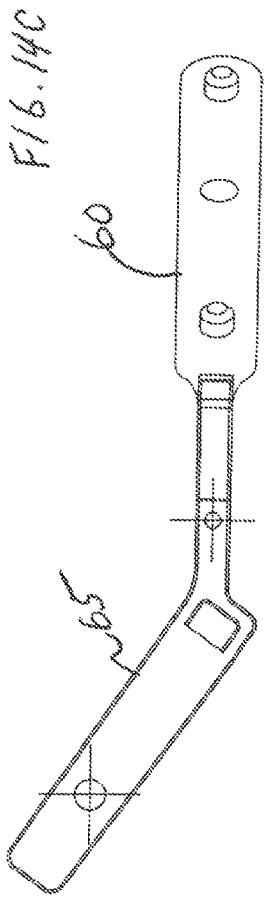
FIG. 14C is a further view of the tracking device and handle of FIGS. 14A-FIG. B.

The following detailed description is of the best currently contemplated modes of carrying out the invention. The description is not to be taken in a limiting sense, but is made merely for the purpose of illustrating the general principles of the invention, since the scope of the invention is best defined by the appended claims.

The invention generally provides a stable affixation system for guided dental implantation, comprising in certain embodiments a fixation tray and a lock. In certain embodiments, the system is designed to be able to attach a tracking device that interacts with a guided dental implantation surgery system wherein such tracking device is kept immobile or at least immobile relative to the patient's mouth.

Certain embodiments of the invention utilize several principles that reflect advantages or requirements for affixation of tracking systems used during dynamic guided dental implant surgery. The first principle is fast and easy placement of a system that is customizable to the patient. The system should allow attachment of a tracker at an anatomical part of the subject such that the tracker and the anatomical part only move in exact conjunction with the surgical site. The second principle is stability of the system holding the tracker even in the face of significant force applied (against the tracker or its connector or against the system directly) including from a variety of angles and through leverage. The third principle is rapid removal of the system with limited force without damaging the teeth.

In certain embodiments, the principle of fast and easy placement is accomplished by a number of things including a fixation tray housing and a flowable or malleable material placed inside the housing which is effectively customizable to the particular patient's teeth because of the material being flowable or malleable. The second principle of stability is in certain embodiments accomplished by several things including the hardening of the flowable or malleable material, a lock mechanism (derived from features of the lock and features of the tray) which reduces or eliminates the freedom of movement of the tray and a mechanism to urge the material against the one or a plurality of teeth. The third principle of fast removal with limited force and without damaging the teeth is accomplished in certain embodiments by a number of things including: an easily removed lock mechanism; using a flowable or malleable material that hardens into a crisp or brittle material and providing the material inside a tray configured to break easily from forces or stress such as shear stress; a mechanism for generating forces or stress (such as shear stress) on the tray and on the material inside the tray; providing that the separation force needed to separate the material from the tray is greater than the separation force needed to separate the already hardened material from the teeth so that the material is removed with the tray and does not stay attached to the teeth when the tray is removed; and using a tray whose housing has at least a portion or portions or areas or points configured to flex under stress (in some embodiments this flexing leads to breakage also of the tray under this stress).

The fixation tray may have a housing that defines a chamber whose inner surface is configured to house a material that is a flowable or malleable material so that the housing in effect becomes customizable to the individual patient's teeth. The feature of the housing having portions that flex under stress facilitates dislodging of the fixation tray.

In one implementation of the housing of fixation tray, the fixation tray may have side walls and a fixation tray top portion that may connect a first side wall with a second side wall of the fixation tray. In certain embodiments, these side walls or portions thereof are configured to flex at least to some extent under stress or pressure. In some cases, these side walls have arm extensions that are significantly more flexible than any other part of the fixation tray including than the first and second side walls, for example because in some embodiments the arm extensions are made of a different material, in one non-limiting example silicone, than the side walls themselves. The extra flexibility of the arm extensions in some embodiments is due to manufacturing considerations but the arm extensions help urge the flowable or malleable material housed by the fixation tray inwardly toward the teeth and may render the fixation tray adaptable to fit more jaw and teeth sizes. This extra flexibility also makes manufacturing the fixation tray easier in certain embodiments. In other cases, the side walls of the fixation tray have an inwardly-directed pair of steps at or near a free end of the side walls or at another position along the side walls.

The affixation system also includes a lock which in certain embodiments is implemented as a locking wedge configured to be placed on the fixation tray in order to reduce or eliminate the freedom of movement of the fixation tray that would otherwise occur from forces on the tray (or from forces on the tracking device (not shown) or the connector of the tracking device that in turn exerts force on the tray) while the tray is positioned on the teeth during the guided dental implantation surgery.

After the flowable or malleable material hardens into a rigid state in a crisp form, one may rapidly remove the affixation system by for example removing the locking wedge followed by exerting a force in the tray such as a force on an element situated in a cavity of the housing (for example a pole that can be rotated within the cavity). The force may be exerted on the element to generate forces or pressure or stress such as shear stress to break at least a portion of the hardened material for example on an occlusal surface of the plurality of teeth and to cause the all or a portion of the sides of the housing (including any arm extensions or steps) to flex so that the fixation tray can be dislodged and removed from the one or the plurality of teeth. If a step is used instead of extra flexible arm extensions, the whole first and second side wall or the sides or side portions of the housing together with the step would flex somewhat due in one example to recesses alongside the side walls or side portions of the housing.

In certain embodiments, the affixation system is configured to be rapidly placed on the one or plurality of teeth, is configured to be rapidly removed from the one or plurality of teeth and/or is configured to be maintained in position in a stable and secure manner (due in part to the locking mechanism) in the face of significant weight or force applied at any of a variety angles including such force applied through leverage.

The principles and operation of a Stable Winged Affixation System for Guided Dental Implantation may be better understood with reference to the drawings and the accompanying description.

As shown in FIGS. 1-15, especially FIGS. 1-2, 4-5 and 8, one embodiment of the invention is a stable affixation system 10 for guided dental implantation that comprises a fixation tray 20 that in certain embodiments has a housing 20a that defines a chamber 25 configured to house a flowable or malleable material (not shown) and be placed over one or a plurality of teeth of a person during guided dental implantation surgery. The use of the flowable or malleable material that hardens so as to conform to the shape of the tooth or teeth of the patient facilitates customizing system 10 (and in particular the housing 20a of tray 20) for the individual patient. This facilitates rapid positioning of system 10 on the one or more teeth of the patient.

Fixation tray 20 is configured to be placed over one or two or three or four or five or six teeth or over a portion of the patient's arch that spans 1-6 teeth. Typically, these would be consecutive adjoining teeth of an arch. In some embodiments, fixation tray 20 is configured to be placed over between 2 and 5 teeth, or over a portion of the arch spanning a row of 2 or 3 or 4 or 5 teeth. In some embodiments, fixation tray 20 is configured to be placed over 1 to 6 adjoining teeth or 2 to 6 adjoining teeth or 2 to 5 adjoining teeth. In some embodiments, system 10 and in particular fixation tray 20, is configured to be placed over one or a plurality (for example two or three or four or five or six) of posterior teeth. The version shown in FIG. 24 through FIG. 29D is primarily for posterior teeth. In other embodiments, system 10 and in particular fixation tray 20, is configured to be placed over one or a plurality (for example two or three or four or five or six) anterior teeth. The version shown in FIG. 30 through FIG. 35E is primarily for anterior teeth.

The mechanism for rapid positioning of system 10 onto the individual patient's teeth may also be implemented at least in part by providing housing 20a with a mechanism for urging the flowable or malleable material against the one or the plurality of teeth. Accordingly, in certain embodiments, housing 20a may have a pair of inwardly directed arm extensions 32, 34 (FIGS. 1-3B) or a pair of inwardly directed steps 23a, 23b (FIG. 15) that extend from an inner surface 25a of chamber 25, each arm extension 32, 34 or step 23a, 23b of the pair configured to urge the flowable or malleable material against the one or more teeth.

Although FIG. 4 depicts housing 20a (and in particular inner surface 25a of chamber 25 defined therein) to include straight portions of its walls, this is only one non-limited implementation and in other embodiments housing and in particular inner surface 25a of the chamber 25 can have round or curved walls or borders. Housing 20a defining chamber 25 may include side portions that may be rounded or straight or a combination of the two. In one implementation, housing 20a (as well as chamber 25) includes a first side wall 22, a second side wall 24 and a fixation tray top portion 26 that connects the two side walls 22, 24. Side walls 22, 24 may be straight or curved or a combination. In one version shown in FIG. 4, housing 20a comprises side walls 22, 24 that have straight portions and rounded portions excluding any arm extensions 32, 34 or steps 23a, 24b. The top portion 26 is sometimes called a cross member 26 and is not necessarily location at a top of housing 20a.

Side walls 22, 24 may be said to run lengthwise. This refers to the direction along the row of teeth (the term "row" is used under the assumption that system 10 is configured to be placed over a plurality of teeth) that the fixation tray 20 is configured to be placed over. In some embodiments, particularly for use with one or a plurality of posterior teeth, chamber 25 defined by housing 20a forms a substantially straight channel in the lengthwise direction.

In certain embodiments, the purpose of fixation system 10 is to be able to attach a tracking system that does not move—or at least does not move relative to the patient's mouth—during the guided dental implantation surgery. To this end, in one non-limiting implementation, fixation tray 20 may have a portion such as a top portion 26 of housing 20a (for example including a holder 28 which is an area of top portion 26) that defines within it (i.e., within holder 28) a cavity, for example an elongated cavity 62, configured to receive a tracking device (not shown) or a handle and/or a connector 60 that connect to such a tracking device. The tracking device may be used during dental implantation surgery. Connector 60 may in some embodiments be made of titanium and may also connect to a registration device or connector 60 itself may be a registration device or part of one. In the embodiment shown in FIG. 1 and FIG. 2 and in the embodiment shown in FIG. 24 through FIG. 28E, and in any method (for example 500, 600), connector 60 may connect to tray 20 using a pole 65 situated at a first end of connector 60 and may connect to the tracking device at the other end of connector. It should be understood that the pole 65 is a non-limiting example of how connector 65 can connect to tray 20 and many other examples are possible with components of other shapes. In addition, the term "pole" is not intended to suggest being cylindrical although it can be.

When lock 40 or locking wedge 40 is not deployed onto fixation tray 20, at least a portion of housing 20a such as side walls 22, 24 are configured to flex under stress. In some embodiments, housing 20a may also be configured to flex under stress at least to some extent from the fact that it defines an open chamber (until the flowable or malleable material hardens into a rigid state). One further way of rendering portions of housing 20a (for example side walls 22, 24) able to flex under stress is to incorporate at least one recess for example at least one recess in the wall of the housing 20a such as recess 27 alongside first side wall 22 and recess 29 alongside second side wall 24. Recesses 27, 29, in one non-limiting embodiment are planar recesses between the respective side wall and a portion of top portion 26, for example holder 28. Other configurations of recesses are also possible in which recesses 27, 29 are not planar. Other ways of making portions of housing 20a configured to flex under stress are also contemplated such as from the nature of the material that housing 20a is made from. In some versions housing 20a is cylindrical thereby requiring only a single recess.

In certain embodiments, portions of housing 20a, for example side walls 22, 24 are configured to flex under stress such that free ends 22b, 24b of walls 22, 24 spread outwards, or at least spread outward more than portions of housing 20a closer to top portion 26. This could occur, for example, as a result of a clamping motion at the other ends of the side walls 22, 24 caused by lock 40 or locking wedge 40.

In versions where housing 20a includes a fixation tray top portion 26 configured to connect first and second side walls 22, 24, then the inner surface 25a of chamber 25 may be defined by an inner surface of tray top portion 26 together with an inner wall surface 22a, 24a of each of the first and second side walls 22, 24. Chamber 25 is configured to house the flowable or malleable material (not shown) which as part of tray 20 may be placed over one or a plurality of teeth (not shown) of a person during guided dental implantation surgery.

In one embodiment, first side wall 22 and the second side wall 24 are each made of a first material and each side wall 22, 24 has an arm extension 32, 34 that is more flexible than side wall 22, 24. Arm extensions 32, 34 may be configured to urge the flowable or malleable material against the one or the plurality of teeth.

The flowable or malleable material, in some embodiments, is of the type of material used for temporary crowns. In one non-limiting example, the flowable or malleable material is highly viscous akin to the viscosity of ketchup (5000-20000 mPa·s at 25° C.) or peanut butter ($10^4$ to $10^6$ mPa·s) or even pitch ($2.3 \times 10^{11}$) and in another example has low viscosity akin to that of whole milk (2.2 mPa·s at 20° C.) or even akin to anything with more viscosity than water (1 at 20° C.) or anything in between any of these ranges. In any event, the flowable or malleable material is not only configured to harden but is also configured to harden into a crisp or brittle material that may be easily breakable in response to the stress, especially in response to shear stress, since this is necessary when one wants to dislodge the fixation tray 20 from the one or plurality of teeth. In some embodiments, the flowable or malleable material is a thermoplastic gel that is as viscous as a viscous liquid but is later heated and then hardens.

In one embodiment, arm extensions 32, 34 extend from each side of housing 20a, for example by extending from each of side walls 22, 24 of housing. In one implementation, arm extensions 32, 34 extend from a free end of side walls 22, 24 respectively (i.e., arm extension 32 extend from a free end of side wall 22 and arm extension 34 extending from a free end of side wall 24). In another embodiment, arm extensions 32, 34 extend from a point adjacent the free end of side walls 22, 24 respectively. In other embodiments, arm extensions 22, 24 extend from a point a few millimeters (1 or 2 or 3 mms) above the free end of side walls 22, 24. In some embodiments, arm extensions extend from a midpoint or a different portion of each of side walls 32, 34. In certain embodiments shown in FIGS. 1-2, arm extensions 32, 34 are inwardly directed. In certain embodiments, arm extensions 32, 34 are also inclined, in one non-limiting example inclined at an angle between 30° and 60° (for example between) 40°-50° relative to side walls 22, 24 respectively (or relative to sides of housing 20a or sides of inner surface 25a of chamber 25). The free ends 22b, 24b, of side walls 22, 24 refer to the end furthest from top portion 26 that in some embodiments connects the side walls 22, 24.

Arm extensions 32, 34 may be made of a material different from the rest of fixation tray 20, for example different from housing 20a or different from side portions of housing 20a or different from the remainder of each side wall 22, 32. For example, in one embodiment arm extensions 32, 34 are made of silicone and the silicone is flexible (and more flexible than any other part of the fixation tray 20 or housing 20a. The fact that arm extensions 32, 34 are inwardly directed and in some case also inclined helps push or urge the flowable or malleable material toward the one or more teeth and helps the fixation tray 20 fit more jaw and teeth sizes. Arm extensions 32, 34 are each configured to form alongside an undercut of the one or more teeth and urge the flowable or malleable material to adhere closely to the anatomical formation of the one or more teeth and into the undercuts so that when this material hardens into a rigid state it in effect grips the one or the plurality of teeth at the undercut of the one or the plurality of teeth. This increases the stability of system 10 in that the entire system 10 not only cannot be dislodged as a unit but in fact is substantially immobile during the dental surgery.

As a result, there is no realistic option to pull the tray 20 plus hardened material straight vertically up off the teeth.

By using a tray 20 having at least portions or a portion that is configured to flex under stress, and by using a flowable or malleable material that once hardens is crisp or brittle, the hardened material in chamber 25 breaks when pressure is exerted (for example by rotating an element, such as pole 65 of connector 60, in cavity 62 of top portion 26 of tray 20) because the force from rotating element 65 generates pressure or stress against fixation tray 20 that translates into stress (such as shear stress) or pressure against the hardened material which breaks it and makes it break away from the teeth (since the hardened material is strongly attached to tray 20). Thus, the hardened material comes off with the tray 20 when the fixation tray 20 is dislodged. If the tray were rigid and not configured to flex under stress, the stress exerted against the tray would not cause the hardened material to break and exerting a force on tray 20 would pressure the tooth or teeth themselves and may simply break or take out the whole tooth or teeth.

In certain embodiments, the housing includes a mechanism or structure configured to join the flowable or malleable material, once hardened, to the housing such that a greater separation force is required to separate the flowable or malleable material, once hardened, from the housing, than a separation force required to separate the flowable or malleable material from the one or the plurality of teeth. In one non-limiting implementation of this mechanism or structure, fixation tray 20, and in particular housing 20a, may have holes 21 (FIG. 1) (or spaces that assume other shapes such as elongated or otherwise) configured to allow the flowable or malleable material to flow into, and when hardened lock into. This way, when the fixation tray 20 is dislodged, the hardened material (formerly flowable or malleable material) breaks with it and dislodges from the teeth. This facilitates rapid removal of the system with limited force and without damaging the teeth. Although FIG. 1 depicts one non-limiting implementation in which one or more holes 21 are situated in side walls 22, 24 of housing 20a of fixation tray 20, it is contemplated that in other implementations, the one or more holes 21 or spaces of other shapes may be situated in other portions of fixation tray 20 such as the top portion 26 of fixation tray. In another non-limiting implementation of this mechanism, the flowable or malleable material is configured by the type and nature of the material itself to adhere to a stronger degree to the material from which the housing of tray 20 is made than the degree to which the flowable or malleable material (once hardened) adheres to the one or the plurality of teeth.

Note that as seen in FIG. 1, tray 20 is upside down relative to how it would be placed on a patient's lower tooth or teeth and right side up in terms of how it would be placed on a patient's upper tooth or teeth. Hence, for convenience, the phrase "placed over" or "deployed over" or "placed on" or "positioned on" one or a plurality of teeth as used in this patent application should be understood broadly to describe both placing, deploying or positioning the tray 20 over a patient's lower teeth (or tooth) as well as placing, deploying or positioning or affixing tray 20 under the patient's upper teeth. Likewise, in this patent application when it is stated that the lock 40 or locking wedge 40 is placed or deployed "over" or "on" tray 20, the word "over" and the word "on" in this context should be understood broadly to also encompass scenarios where the system is applied to upper teeth and the lock 40 or wedge 40 is affixed to the tray 20 by placing lock 40 or wedge 40 under tray 20 when the tray 20 is held in a position secured to (or in position to be secured to) the upper teeth.

As seen from FIGS. 1-2 and 8-11, fixation system 10 may also comprise a lock 40 positioned on tray 20 (which may be implemented in one embodiment as a locking wedge 40 positioned on or over the fixation tray 20) so as to reduce or eliminate a freedom of motion or movement of housing 20a or of all or part of side portions of housing 20a or of sides or of first and second side walls 22, 24 of housing 20a of fixation tray 20. Lock 40 or locking wedge 40 is configured with some mechanism designed to fixate housing 20a or at least side portions of housing 20a rigidly in place. In one implementation, lock 40 or locking wedge 40 is configured to fixate side walls 22, 24 rigidly in place. In any embodiment, the phrase "locking wedge" refers to lock 40 being positioned over fixation tray 20 using a friction fit or fitting snugly on fixation tray 20. It may or may not involve tapered walls of the lock 40 but even if it involves tapered walls such tapered walls of the lock 40 do not necessarily have to taper down to a thin edge.

In certain embodiments of locking wedge 40, locking wedge 40 has an inner surface 40a (FIG. 8) configured to define a chamber 45 into which the fixation tray 20 is configured to be emplaced or to be fit. For example, inner surface 40a may be configured such that tray 20 for example fits into chamber 45 snugly or for example fits into chamber 45 using a friction fit or under pressure.

In one non-limiting implementation of the mechanism to fixate or remove the flexibility of the housing 20a or of at least of a portion of housing 20a, locking wedge 40 may include a first locking wedge side wall 42 thicker than the first side wall 22, a second locking wedge side wall 44 thicker than the second side wall 24 and may also include a locking wedge top portion 46 configured to connect the first and second locking wedge side walls 42, 44. FIG. 9 is a top view that depicts sides 44, 46 of wedge 40 as if splayed outward but this view is not intended as a realistic depiction.

As noted, and as seen from FIG. 4, fixation tray 20 or its top portion 26 may in certain embodiments have a recess 27 situated alongside side wall 22 for example alongside a protruding top portion of first side wall 22 and a recess 29 situated alongside side wall 24 for example alongside a protruding top portion of second side wall 24. FIG. 4 does not show and is not intended to depict any arm extensions 32, 34 or any steps 23a, 23b that housing 20a may have.

As seen from FIG. 8, locking wedge top portion 46 in certain embodiments has projecting members 47, 49 that are configured to mate with or fit inside at least a portion of recesses 27, 29 respectively, as seen also from FIG. 1. For example, locking wedge top portion 46 may have planar projecting members 47, 49 that correspond to planar recesses 27, 29 in certain embodiments. In other embodiments, recesses 27, 29 fit together with projecting members 47, 49 without either of them being planar. Projecting members 47, 49, which may be planar, may project from an underside of the locking wedge top portion 46.

As seen from FIGS. 1-2, 4 and 8, in one embodiment, substantially planar recesses 27, 29 are situated such that when the substantially planar projecting members 47, 49 mate with the substantially planar recesses 27, 29, a first substantially planar projecting member 47 is adjacent to and inward of the first side wall 22 of the fixation tray 20 and a second substantially planar projecting member 49 is adjacent to and inward of the second side wall 24 of the fixation tray 20.

In certain embodiments of system 10, there is a structural means of snapping or locking or fitting together by friction fit or otherwise fixedly connecting locking wedge 40 to fixation tray 20. In one non-limiting implementation of this connection shown in FIG. 1, FIG. 5 and FIG. 11, both fixation tray 20 and locking wedge 40 have ridges 99 on portions of their side walls. For example, as shown in FIGS. 1, 5, 11, outer surfaces of side walls 22, 24 of fixation tray 20 and inner surfaces of side walls 42, 46 of wedge 40 have corresponding or matching ridges 99.

When locking wedge 40 is placed on fixation tray 20, locking wedge 40 is configured to reduce or eliminate a freedom of movement of each of the first side wall 22 and the second side wall 24 of fixation tray 20. In one non-limiting example, locking wedge 40 is configured to reduce a freedom of movement of each of the first side wall 22 and the second side wall 24 by 40% (or by at least 40%) or in other embodiments by 50% (or by at least 50%) or in other embodiments by 70% (or by at least 70%) or in still other embodiments by 90% (or by at least 90%) or in still other embodiments by a particular percent between 40% and 95%.

As can be seen from FIG. 4 and FIG. 8 an end view of at least one of (i) the fixation tray 20 or (ii) the locking wedge 40 is substantially U-shaped. Although FIG. 4 does not include arm extensions 32, 34, even with arm extensions 32, 34 (see FIG. 2) tray 20 may be considered substantially U-shaped.

Figure 19:
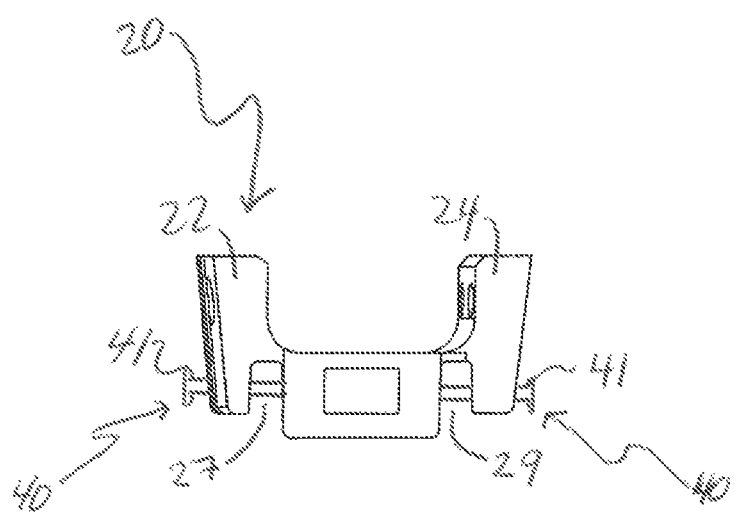
FIG. 19 is a schematic of a lock mechanism applied to FIG. 4, in accordance with an embodiment of the invention.
Figure 20:
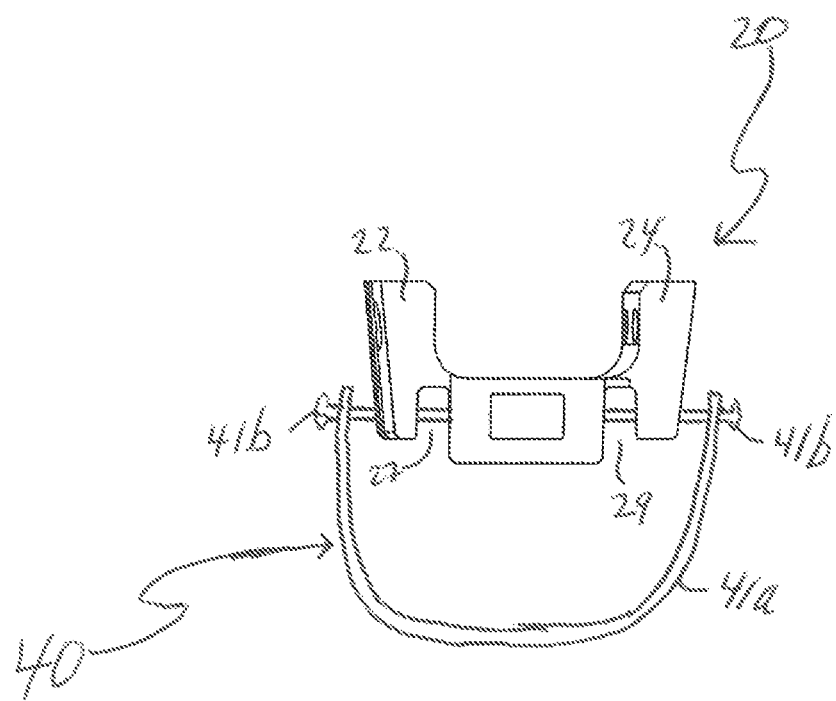
FIG. 20 is a schematic of another lock mechanism applied to FIG. 4, in accordance with an embodiment of the invention.
Figure 22:
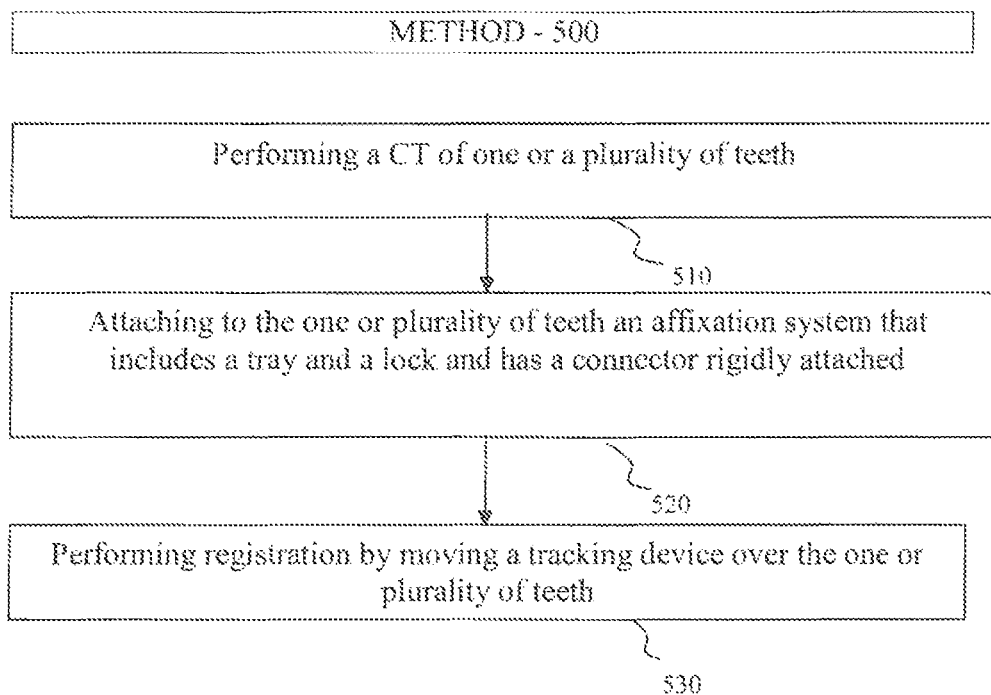
FIG. 22 is a flow chart of a registration method, in accordance with an embodiment of the invention.
Figure 23:
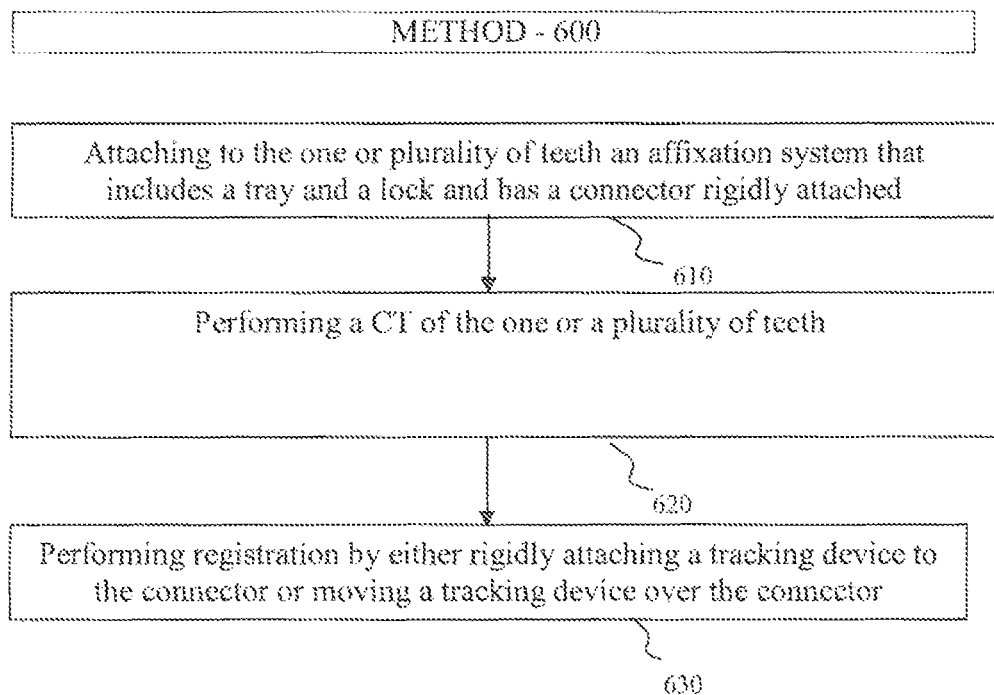
FIG. 23 is a flow chart of another registration method, in accordance with an embodiment of the invention.

In another implementation of lock 40 shown in FIG. 19 and FIG. 20, the housing 20a includes locking mechanism 40 configured to reduce or eliminate a freedom of movement of the fixation tray 20 by reducing or eliminating an ability of the at least the portion of the sides of the housing to flex under stress. In one non-limiting example, lock 40 comprises a clamp 41a and/or a fastener 41b (i.e., screw 41b or a pair of screws 41b) integrated with the tray 20 (or in other versions not integrated with the tray 20) such that adjustment of the clamp 41a and/or screw(s) 41b is configured to reduces or eliminates the ability of housing 20a to flex under stress. In one implementation of this example, the clamp 41a and/or screw(s) 41b is configured to accomplish this by locking side walls 22, 24 of housing 20a, for example by traversing recesses 27, 29. Another implementation of lock 40 is similar to FIG. 20 except that there are no recesses 27, 29 in tray 20 and the clamp 41a is positioned to grip tray 20 further down, that is further from top portion 26 and close to free ends of side walls 22, 24 (or at least closer to free ends of side walls 22, 24 than shown in FIG. 20). In that case, lock 40 may also comprise screw(s) 41a (although in other versions clamp 41a operates without screws 41b).

Accordingly, one particular embodiment of the invention is a stable affixation system 10 for guided dental implantation, comprising a fixation tray 20 customizable to the patient including a housing 20a that defines a chamber 25 configured to house a flowable or malleable material and be placed over one or a plurality of teeth of a person during the guided dental implantation surgery, the housing 20a having sides, wherein at least a portion of the sides are configured to flex under stress, the sides configured to urge the flowable or malleable material against the teeth, and wherein the housing 20a includes a locking mechanism 40 configured to reduce or eliminate a freedom of movement of the fixation tray by reducing or eliminating an ability of the at least the portion of the sides of the housing 20a to flex under stress. In some versions, the least a portion of the sides of the housing are configured to flex such that a further a portion of the sides is from a top portion of housing the more that portion of the sides spreads outward under stress. In some versions, the system 10 further comprises a registration element 60 configured to connect to tray 20. In that case, system 10 includes that which is necessary for the tray 20 and lock 40 to be registered for purposes of the guided surgery. The registration element is configured to align for a computer navigation system used during the surgery the exact CT coordinates with the exact real-world coordinates of a registered body rigidly attached to (or forming part of) system 10.

As shown in FIG. 24 through FIG. 35E, one embodiment of the affixation system 10, referred to herein as the "flexion" embodiment, is a stable affixation system for guided dental implantation, comprising a fixation tray 20 customizable to the patient including a housing 20a that defines a chamber 25 configured to house a flowable or malleable material and be placed over one or a plurality of teeth of a person during the guided dental implantation surgery. As in other embodiments, fixation tray 20 including housing 20a is configured to be placed over the one or plurality of teeth by being placed over a front, top and rear of the one or plurality of teeth.

Fixation tray 20 is configured to be placed over one or two or three or four or five or six teeth or over a portion of the patient's arch that spans 1-6 teeth. Typically, these would be consecutive adjoining teeth of an arch. In some embodiments, fixation tray 20 is configured to be placed over between 2 and 5 teeth, or over a portion of the arch spanning a row of 2 or 3 or 4 or 5 teeth. In some embodiments, fixation tray 20 is configured to be placed over 1 to 6 adjoining teeth or 2 to 6 adjoining teeth or 2 to 5 adjoining teeth. In some embodiments, system 10 and in particular fixation tray 20, is configured to be placed over one or a plurality (for example two or three or four or five) of posterior teeth (or five posterior teeth pus an adjacent tooth). The version shown in FIG. 24 through FIG. 29D is included in these embodiments. In other embodiments, system 10 and in particular fixation tray 20, is configured to be placed over one or a plurality (for example two or three or four or five or six) of anterior teeth. The version shown in FIG. 30 through FIG. 33B is included in these embodiments. Housing 20a may have sides or side walls 22, 24 joined to a cross member 26 on each side of the housing 20a. Housing 20a may include a flexion region on each of its sides. For example, cross member 26 may include a flexion region FR on each side of housing 20a. Each of the side walls 22, 24 may include an upper side portion 22U and a lower side portion 22L of a first side wall 22 and an upper side portion 24U and a lower side portion 24L of a second side wall 24, such that in an unlocked position a squeezing force on the upper side portions 22U, 24U flexes the lower side portions 22L, 24L outward. Cross member 26 may connect side walls 22, 24 to one another.

As shown in FIG. 25, FIG. 26A, FIG. 27A, FIGS. 29A-D, the "flexion" embodiment of system 10 may also comprise a lock 40 positioned on the fixation tray 20 so as to reduce or eliminate a freedom of movement of the fixation tray 20. According to some implementations, lock 40 is configured to directly reduce or eliminate a freedom of movement of the upper side portions 22U, 24U of side walls 22, 24 of fixation tray 20 and thereby also indirectly reduce or eliminate a freedom of movement of lower side portions 22L, 24L of side walls 22, 24. Side walls 22, 24, and in particular typically lower side portions 22L, 24L of side walls 22, 24 are configured in the locked position (when lock 40 is positioned on fixation tray 20) to urge the flowable or malleable material, having hardened, against the teeth.

The "flexion" embodiment has two versions (at least). In one of these two versions, holder 28 is situated projecting out of cross member 26 essentially on the top portion of fixation tray 20. In a second version holder 28 is positioned on a side of the fixation tray 20. One version may be for posterior teeth and one version for anterior teeth. Typically, the version with holder 28 projecting out of cross member 26 is geared primarily for posterior teeth and the version with holder 28 projecting out of the side of fixation tray 20 is geared primarily for anterior teeth but that is not a requirement. In fact, the version with holder 28 projecting out of the side of tray 20 may also be used for posterior teeth. In addition, the version for one type of teeth, for example posterior teeth, may include one anterior tooth for example at the end of the plurality of teeth. Another difference between the two versions is the degree of curvature (i.e., lengthwise along the row of teeth) since more curvature is needed to accommodate the greater curvature of the arch at the anterior teeth. Another difference that may appear is that in the version for the anterior teeth, the non-lip side of the tray 20 may comprise a shortened lower side portion 22L of wall 22 of tray 20.

Figure 32B:
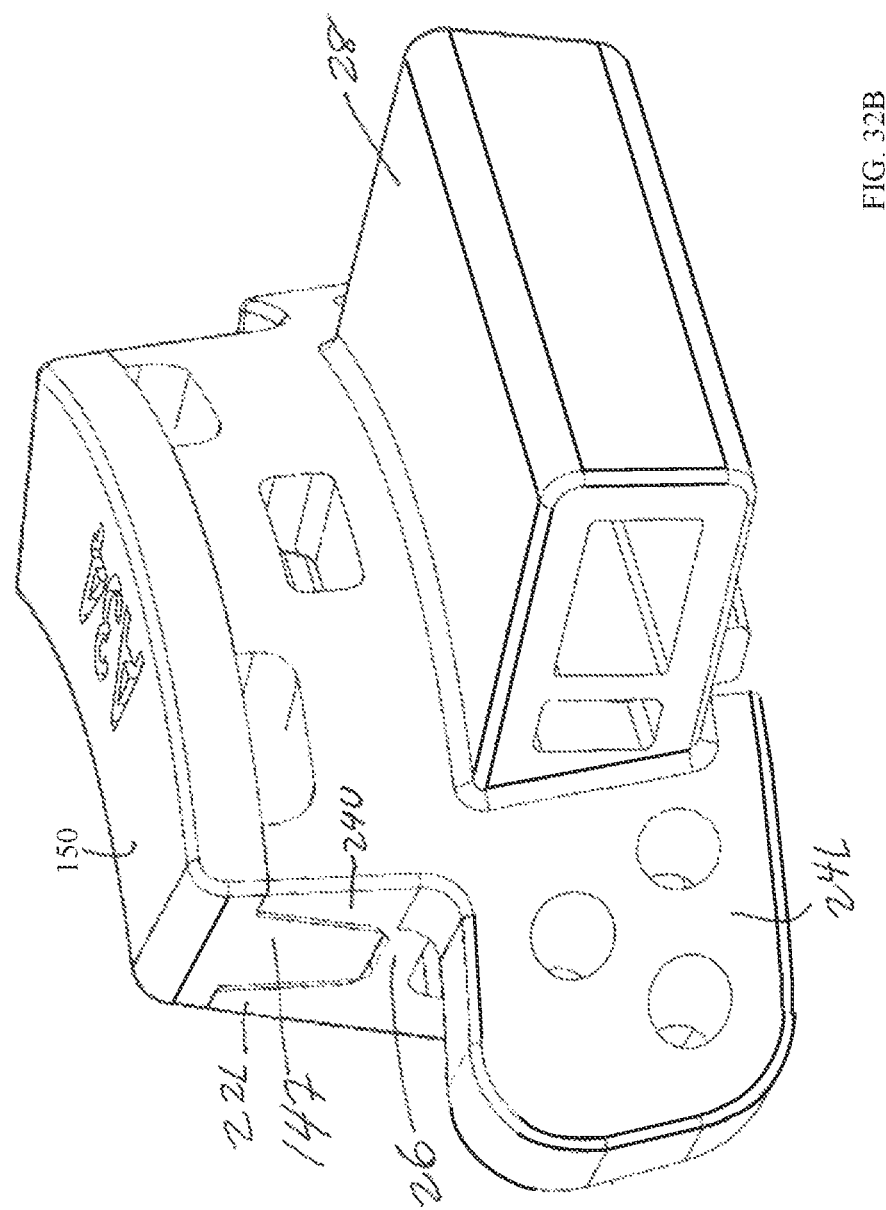
FIG. 32B is a perspective view of the fixation tray and lock of FIG. 32A fitted together, in accordance with one embodiment.

Accordingly, one version is shown in FIGS. 24-29D in which holder 28 is situated projecting out of cross member 26 on the top portion of fixation tray 20. The version is configured for use primarily for posterior teeth of a person. Another version which positions holder 28 on a side of the fixation tray 20 is shown in FIGS. 30-33B. At least in part due to its greater lengthwise (along the row of teeth) curvature, is geared primarily for anterior teeth. A third version is geared for posterior teeth (similar to that shown in FIGS. 24-29D but includes holder 28 projecting from one of the side walls 22, 24 of tray 20 (as shown in FIG. 32A). This is shown in FIGS. 37 to 40.

Figure 24:
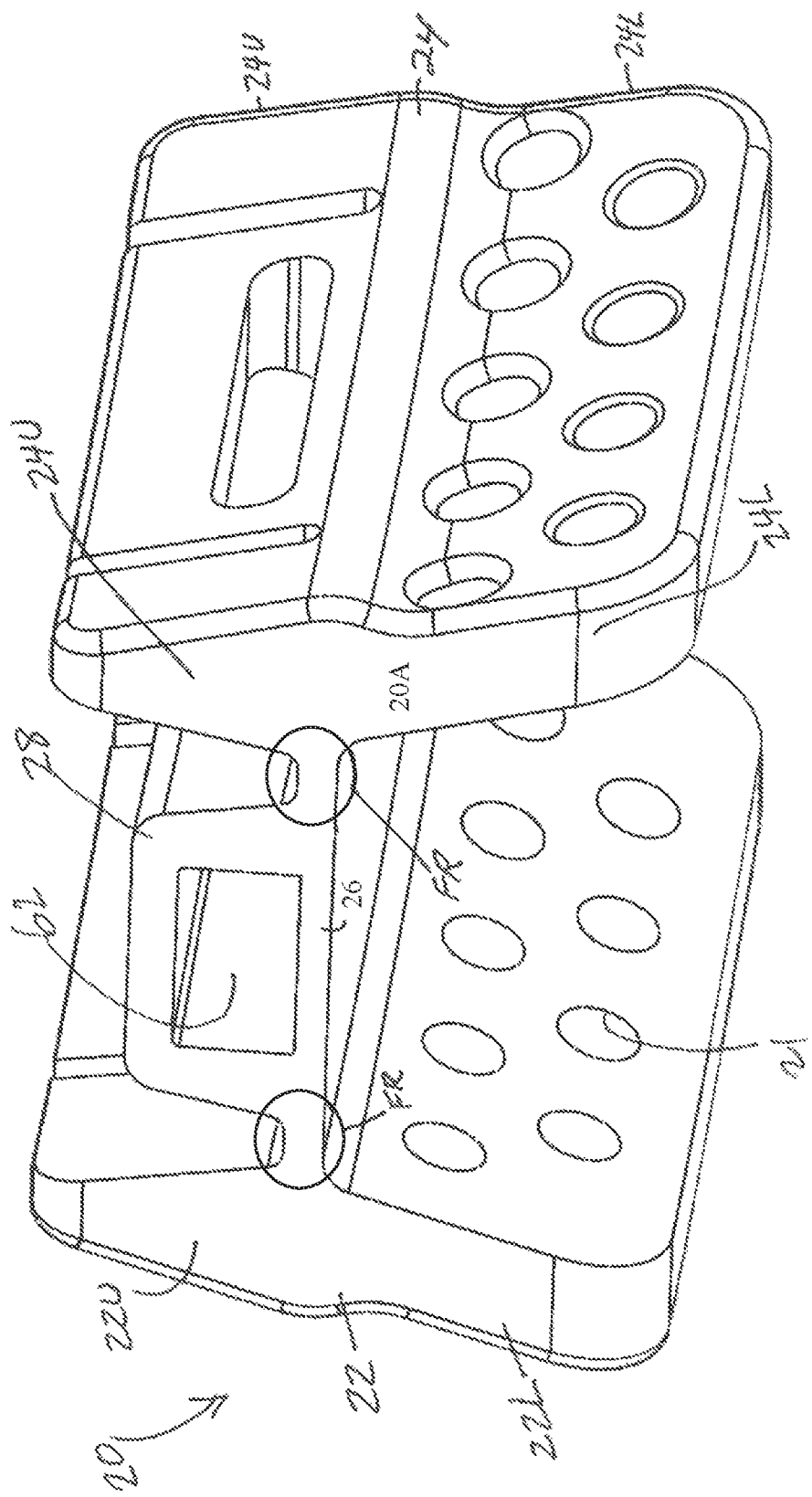
FIG. 24 is a perspective view from the end and front of a fixation tray primarily for posterior teeth, in accordance with one embodiment.

In either case, lock 40 includes at least one projecting member 47A or 147 that fits into a recess on fixation tray 20. In versions with holder 28 projecting from cross member 26, lock 40 comprises projecting members 47, 49 whose external side walls 47a, 49a are tapered. Projecting members 47, 49 are configured to mate with or fit into (for example snugly or using a friction fit) correspondingly shaped recesses 27, 29 of the fixation tray 20, each of the recesses 27, 29 defined in part by the upper side portions 22U, 24U of side walls 22, 24 and by the flexion region, FR, (FIG. 24). Projecting member 47 may also be defined by a further wall 28a protruding from cross member 26 further inward than side wall 22 and likewise projecting member 49 may also be further defined by a further wall 28b further inward than side wall 24.

For example, further walls 28a, 28b may form part of a holder 28 protruding from cross member 26, holder 28 configured to define a cavity 62 configured to receive a tracking element (as part of the tracking system) used during dynamic guided dental implant surgery. First projecting member 47 of lock 40 may be configured to flex or urge the upper side portion 22U of side wall 22 of housing 20a outward thereby flexing the lower side portion 22L of side wall 22 of housing 20a inward. Likewise, second projecting member 49 of lock 40 may be configured to flex or urge the upper side portion 24U of side wall 24 of housing 20a outward thereby flexing or urging the lower side portion 24L of side wall 24 of housing 20a inward, thereby facilitating the urging of the flowable or malleable material against the teeth of the patient.

As shown in FIG. 25, FIG. 26A, FIG. 27A, FIG. 29A and FIG. 29D, first projecting member 47 and a second projecting member 49 may also represent outer side walls of lock 40.

In the version of the "flexion" embodiment shown in FIGS. 30-33B, as best seen from FIG. 30, side walls 22, 24 of the housing 20a may be curved along a lengthwise direction of the side walls (the lengthwise direction of the side walls refers to the lengthwise direction along the row of teeth or consecutive teeth of the plurality of teeth (moving from one tooth to the next)). In this case, lock 40 may comprise a projecting member 147, which may be a unitary projecting member 147, whose external side walls 147a, 147b are tapered, as seen in FIG. 31, the projecting member 147 configured to fit into (for example snugly or using a friction fit) a correspondingly shaped recess 127 of fixation tray 20, the recess 127 defined by the upper side portions 22U, 24U and the cross member 26. As seen from FIG. 32A (and similarly FIG. 25), lock 40 may have top portion 150 from which projecting member 147 (and similarly 47, 49) may project and top portion 150 may be wider than projecting member 147 in order to grasp lock 40.

In the version with holder 28 on the side, as seen from FIG. 30 through FIG. 24E, holder 28 does not typically project from cross member 26 (for example from a top of cross member 26) but rather from one of the side walls 22, 24 of the housing 20a of fixation tray 20. Holder 28 is configured to define a cavity 62 configured to receive a tracking element (as part of the tracking system) used during dynamic guided dental implant surgery. The projecting member 147 may be configured to be snugly positioned adjacent each of the upper side portions 22U, 24U so as to flex the upper side portions 22U, 24U outward and thereby urge the lower side portions 22L, 24L inward.

In addition, as seen from FIG. 28 and FIG. 29A, the lower side portion 22L of the wall 22 of tray 20 that is on the non-lip side of tray 20—the side that goes further into the mouth of the patient—is typically shorter than the lower side portion 24L of the wall 24 of tray 20 that is on the lip side of tray 20. This is for practical reasons.

Figure 25:
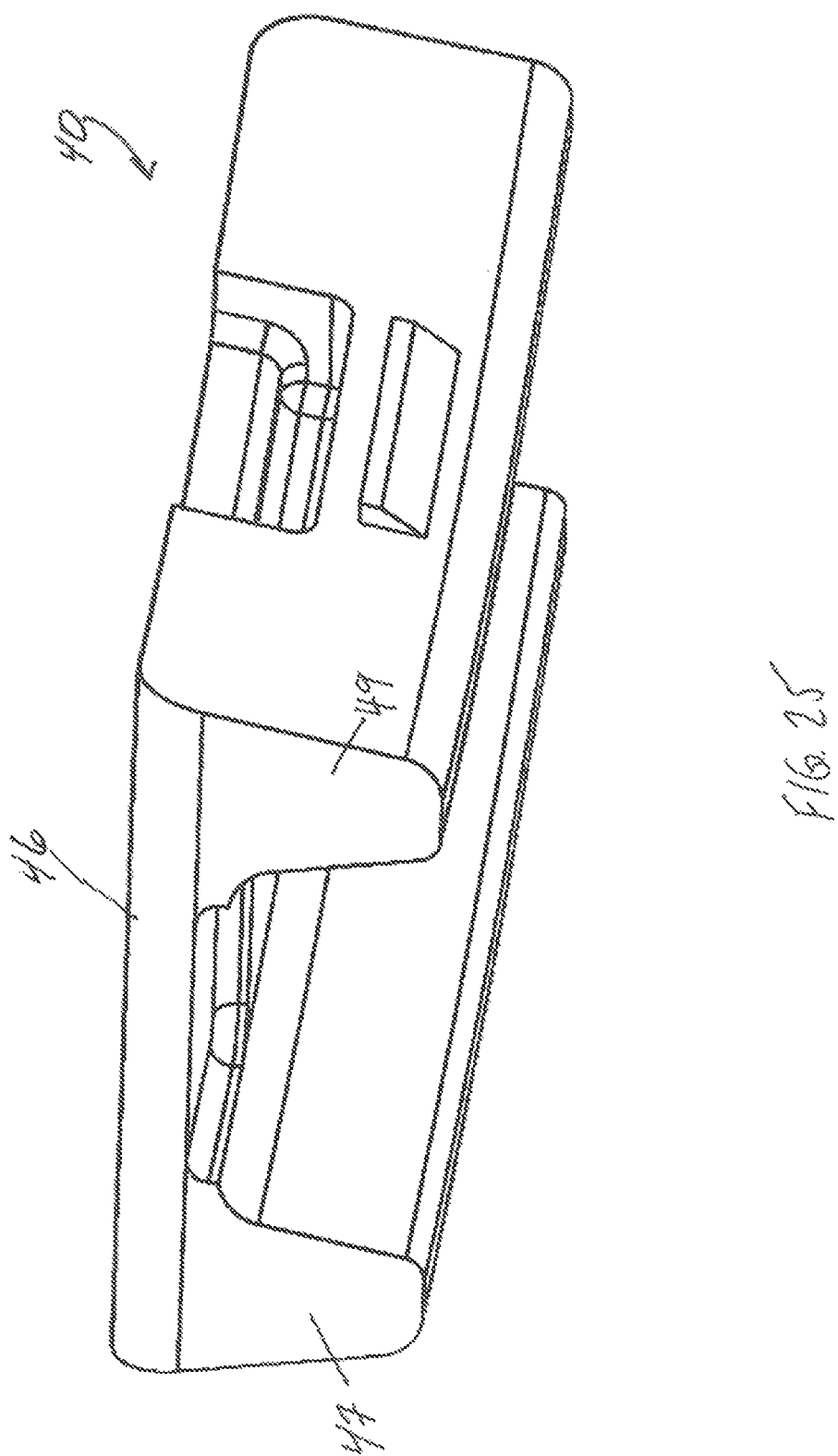
FIG. 25 is a perspective view of a lock for the fixation tray of FIG. 24, in accordance with one embodiment.
Figure 26A:
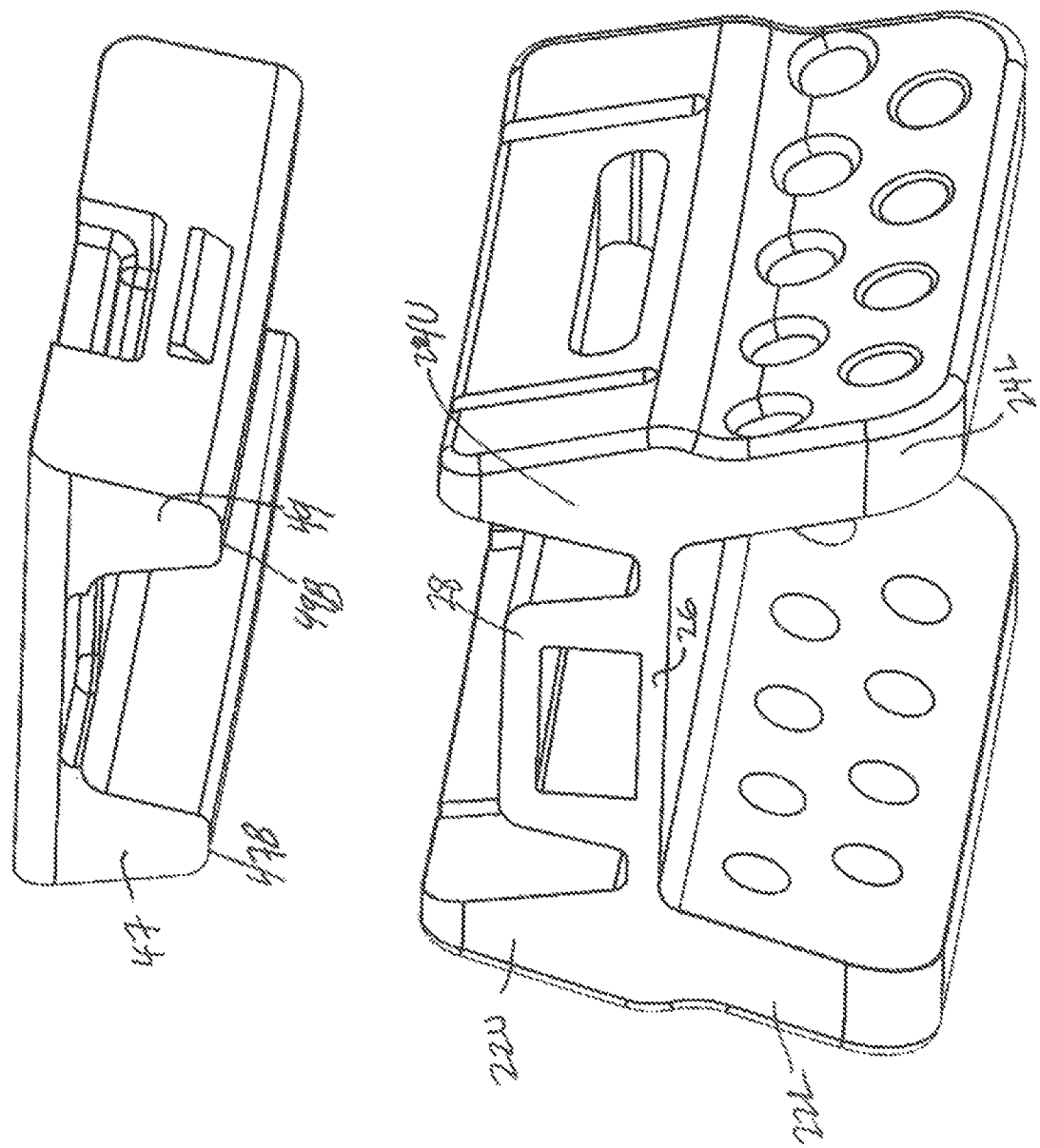
FIG. 26A is an exploded view of the fixation tray and lock of FIGS. 24-25, in accordance with one embodiment.
Figure 22B:
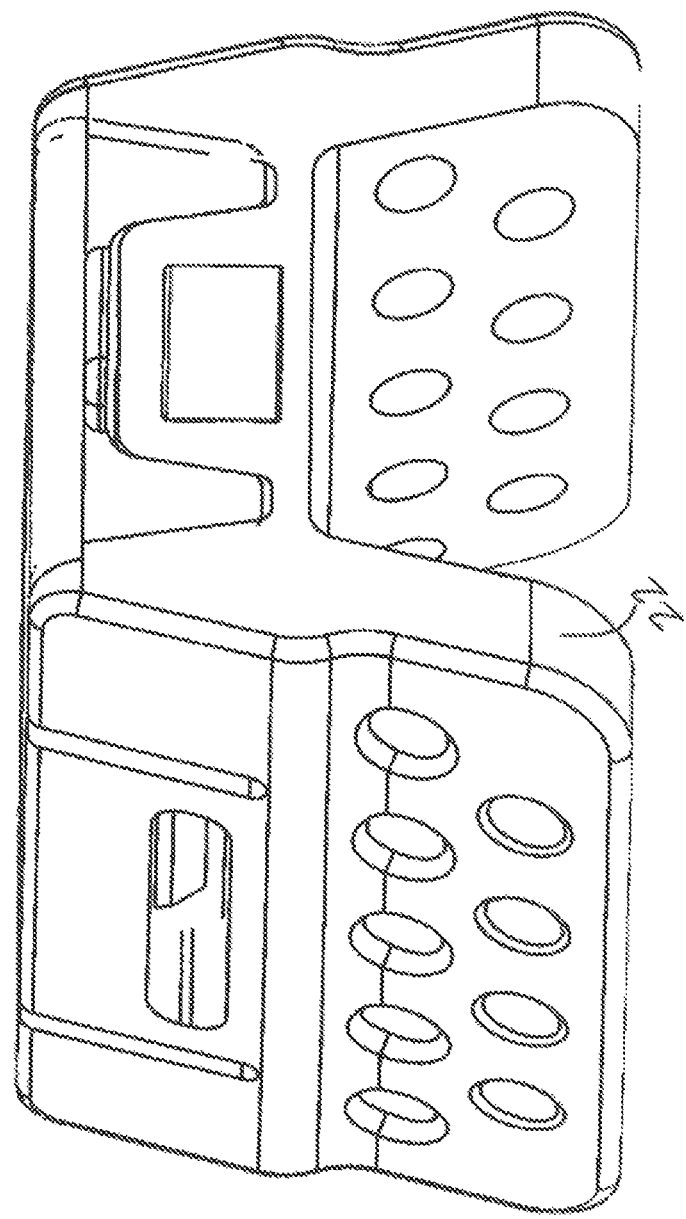
Figure 28C:
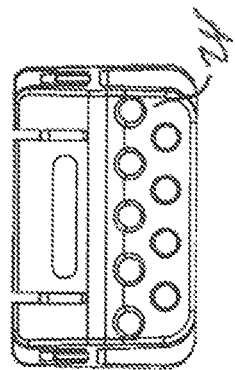
FIG. 28C is a side view of a fixation tray primarily for posterior teeth, in accordance with one embodiment.
Figure 28B:
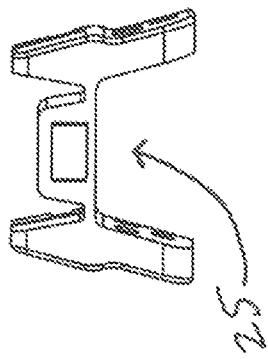
FIG. 28B is an end view of a fixation tray primarily for posterior teeth, in accordance with one embodiment.
Figure 28A:
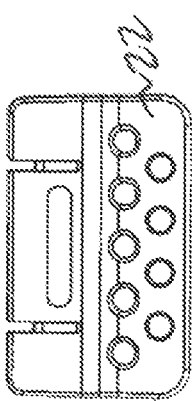
FIG. 28A is a side view of a fixation tray primarily for posterior teeth, in accordance with one embodiment.
Figure 28E:
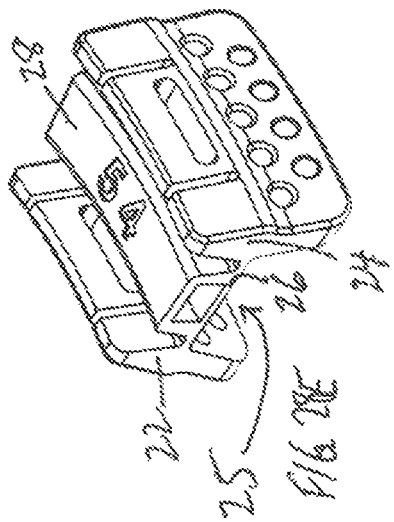
FIG. 28E is a perspective view of a fixation tray primarily for posterior teeth, in accordance with one embodiment.
Figure 28D:
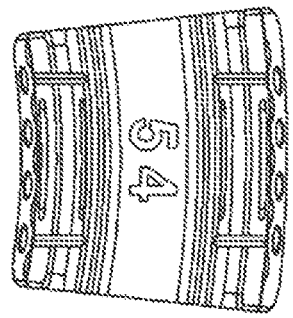
FIG. 28D is a top view of a fixation tray primarily for posterior teeth, in accordance with one embodiment.

Regarding the tapering of the thickness of projecting members 47, 49 and of projecting member 147 as one goes toward the bottom of lock 40 (the bottom being the part closer to the gumline and in some embodiments the part or edge that is configured to contact the cross member 26 of fixation tray 20 (not including any holder 28), in one particular non-limiting implementation shown in FIG. 25, the tapering is such that it decreases the thickness by about 50% or by at least 50%. In some embodiments, the respective cross-sections of first projecting member 47 and of second projecting member 49 are substantially triangular or substantially trapezoidal or substantially wedge-shaped although the respective bottom edges 47B, 49B of these projecting members 47, 49 will not necessarily be pointy (for example so as to increase the surface area of lock 40 that mates with tray 20) as shown in FIG. 25.

Furthermore, in some embodiments, holes 21 are present in side walls 22, 24 of fixation tray 20 and holes 21 are configured to receive the flowable or malleable material. Although FIG. 24A shows nine holes 21 carved into each of lower side portions 22L, 24L in a particular pattern and of a particular size, it should readily be understood that the number, size and position of these holes 21 can vary.

In an unlocked position (after lock 40 is removed from fixation tray 20 or before lock 40 is positioned on fixation tray 20), squeezing first and second side walls 22, 24 of fixation tray 20 toward one another is configured to release tray 20 from the one or plurality of teeth (because of the effect of the flexion region) by flexing lower portions 22L, 24L outward and away from the hardened material (thereby causing the material to break). Thus, the flexion embodiment of system 10 achieves rapid positioning of the tray 20 and lock 40 onto the patient's teeth as well as easy and rapid removal of system 10 with limited force and without damaging the teeth. Furthermore, in this flexion embodiment, the easy and rapid removal of system 10 with limited force and without damaging the teeth is achieved using the force of the squeezing of side walls 22, 24 to break lower portions 22L, 24L away from the hardened material without the need for insertion of an element into a cavity (such as a cavity of holder 28) in order to generate stress on housing 20a.

Side walls 22, 24 may be said to run lengthwise, which refers to the direction along the row of teeth (the term "row" is used under the assumption that system 10 is configured to be placed over a plurality of teeth but the directional meaning of "lengthwise" also applies to a single tooth) that the fixation tray 20 is configured to be placed over.

Figure 33A:
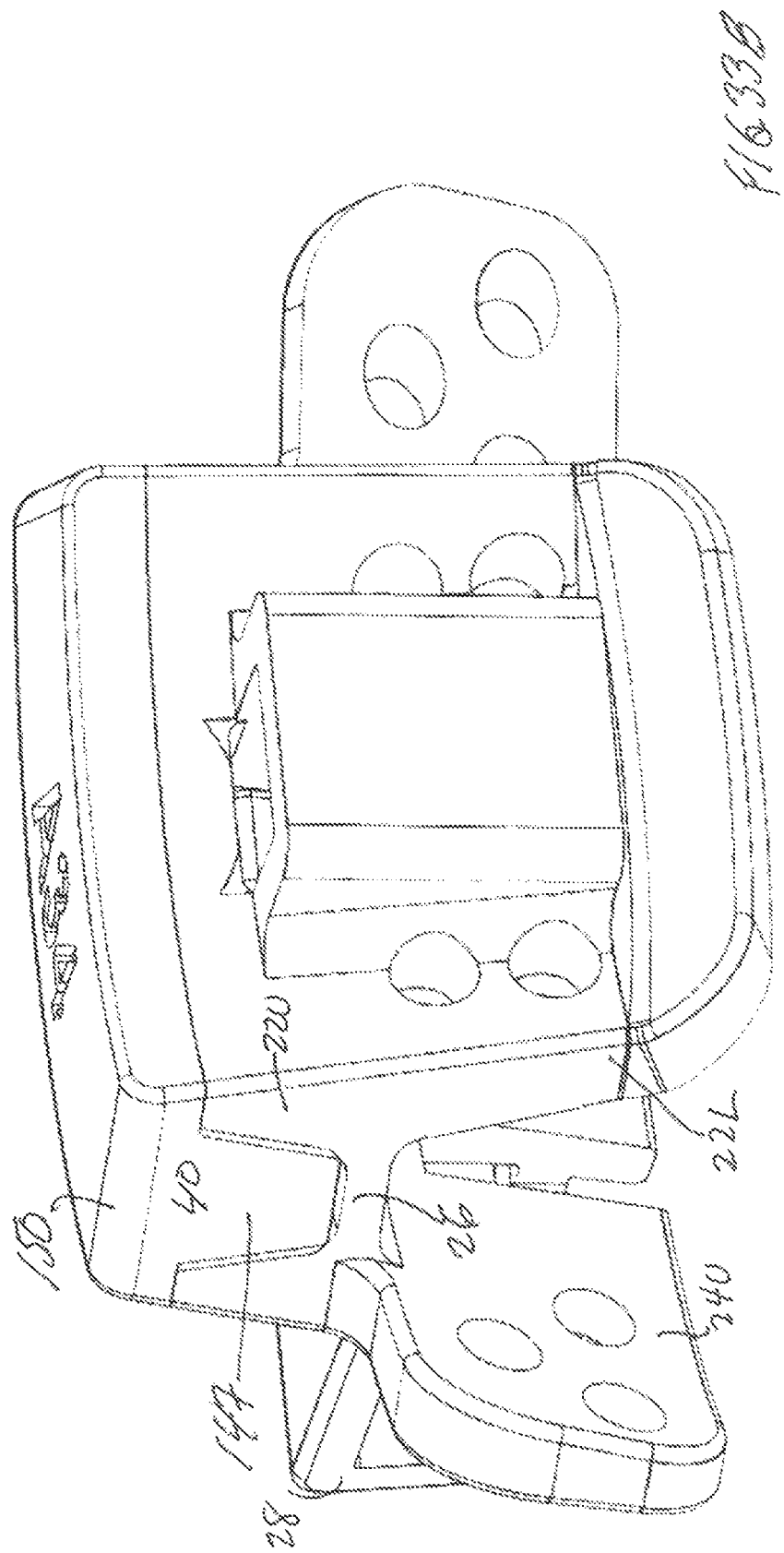
FIG. 33A is an exploded rear view of fixation tray of FIGS. 30-31, in accordance with one embodiment.

As seen in FIG. 24, FIG. 26A-B, FIG. 27A-B and FIG. 28B and FIG. 28E, chamber 25 may be defined by lower side portions 22L, 24L and cross member 26 or top portion 26 of housing 20a. Chamber 25 may be shaped as a channel whose length is in the direction of the row of teeth. In some embodiments, chamber 25 is shaped as a channel that is substantially straight in the lengthwise direction (in the direction of the row of teeth or in the direction of consecutive teeth of the plurality of teeth that tray 20 is placed on). In the version with holder 28 on the side, for the anterior teeth, chamber 25 may be shaped as more of a curved channel as seen in FIG. 30, FIG. 33B and FIG. 34D. The fixation tray 20 that is configured to be placed over a plurality of posterior teeth may also have some degree of curvature but less than that for tray 20 configured to be placed over anterior teeth.

As seen from the flow chart of FIG. 16, one embodiment of the invention is a method 100 of using a stable affixation system during dental implantation. Method 100 may comprise a step 110 of deploying a fixation tray 20 holding a flowable or malleable material over one or a plurality of teeth, the fixation tray having a housing 20a wherein at least a portion such as side portions of housing 20a (in one implementation side walls (for example a first side wall 22 and a second side wall 24)) are configured to flex under stress. Housing 20a may include a fixation tray top portion 26 or a cross member 26 that may be configured to connect the first and second side walls. The housing 20a defines a chamber 25 and may have any of the structures described with respect to any of the embodiments of fixation tray 20 or system 10 including the flexion embodiment. For example, housing 20a may have an element such as extra flexible arm extensions, for example arm extensions that are inwardly facing (and that may be inclined) to urge the flowable or malleable material against the one or more teeth. For example, arm extensions 32, 34 may extend from a free end or a point adjacent to a free end of, or may extend from a different part of, each of the first and second side walls (or side portions of housing 20a) as inclined inward-directed arm extensions configured to urge the flowable or malleable material against the one or the plurality of teeth. In some embodiments, the step 110 of deploying may be accomplished rapidly and easily.

Method 100 may also include step 120 of locking the fixation tray such as by a lock 40 or by deploying a locking wedge over the fixation tray, for example a locking wedge 40 that is configured to fixate tray 20 in place or grip fixation tray 20 and/or reduce or eliminate its freedom of movement. The mechanism for reducing or removing the freedom of movement of tray 20 or fixating tray 20 in place may be any suitable mechanism for example any mechanism described with regard to system 10 or tray 20. In some embodiments, the step 120 of locking effectuates a stable and sturdy system to which a tracking device may be attached and which is stable in the face of significant force applied from any of a variety of angles and using leverage. Step 120 may also include locking an element such as pole 65 for example by using a fastener or screw that traverses both a hole in lock 40 and a hole in tray 20 (see FIG. 1, FIG. 5, FIG. 9).

Step 130 of method 100 may comprise allowing the flowable or malleable material to harden, for example to harden into a rigid but crisp or brittle state, for example a crisp or brittle state that is easily breakable upon application of a force or stress such as shear stress. The flowable or malleable material in some case flows into spaces 21 in housing 20a of tray 20 so that when it hardens it locks into tray 20. In some embodiments, the step 130 of allowing the flowable or malleable material to harden is performed before the step 120 of deploying the lock 40 or locking wedge 40 on the fixation tray 20. Depending on the material there can be different degrees of brittleness produced. Also, the flowable or malleable material may in some embodiments be a thermoplastic.

Method 100 may include an additional step of redeploying the fixation tray holding new flowable or malleable material on the one or a plurality of teeth such that the fixation tray (and lock) regains a same spatial position relative to the one or more plurality of teeth (or jaw bone). Further steps may include letting the new flowable or malleable material harden and repositioning the lock on the tray so as to retain the same spatial position of the tray (and lock) relative to the one or more plurality of teeth (or jaw bone). Thus, method 100 may achieve a feature of precise repeatability of the deployment of system 10.

The method 100 may include an additional step of performing the guided dental surgery while system 10, including tray 20 and lock 40, remain in place in a sturdy and stable position without regard to forces exerted on system 10.

Step 140 may involve unlocking the lock 40 or removing the locking wedge 40 and then removing the fixation tray 20, for example easily and rapidly with limited force without damaging the tooth or teeth. For example, the locking wedge 40 is removed in certain embodiments rapidly by exerting a force on it for example using an instrument that is operatively connected to the element in a cavity 62 of the fixation tray 20. Removing the fixation tray 20 may be accomplished in certain embodiments by exerting a force that generates stress such as shear stress on the housing 20a that may translate into stress such as shear stress on the crisp or brittle hardened material (formerly flowable or malleable material). In one non-limiting implementation, this may be accomplished by exerting a force (such as a rotational force) on an element (such as a pole 65) of tray 20. For example, the force may be applied to an internal element of tray 20. In one implementation, the force may be applied to an element situated in a cavity 62 of the fixation tray 20 such as in top portion 26 of tray 20 (which in some embodiments is a cavity 62 in a holder 28 of top portion 26) to generate pressure causing stress such as shear stress on portions of the tray 20 and on the hardened material to break at least a portion of the hardened material (for example on an occlusal surface of the plurality of teeth), thereby allowing the sides or side portions of housing 20a (including arm extensions 32, 34 or including steps 23a, 23b) to flex and dislodge the fixation tray 20 from the plurality of teeth. FIG. 1 is an exploded view that allows the visualization of the element in the cavity 62 according to one embodiment. A tracking device connector or handle 60 includes a pole portion 65 configured to fit inside cavity 62. In order to begin the process of removing the fixation tray 20, one can exert a rotational force on pole 65. This has the effect of pressuring the entire fixation tray 20 but in particular on the sides of tray 20, for example arm extensions 22, 24 of tray 20. It may have the effect of pressuring holder 28, top portion 26, side walls 22, 24 and arm extensions 32, 34. It may have an additional effect of exerting stress such as a shear stress and breaking at least a portion of the hardened material, for example on an occlusal surface of the plurality of teeth, thereby allowing side portions of housing 20a to flex so as to dislodge fixation tray 20 from the one or the plurality of teeth and remove fixation tray 20.

In method 100 (or method 200, 300, 400) if an element for example pole 65, has been placed in tray 20, then step 140 may also include removing a fastener or screw that locks pole 65.

Another method 200 shown in FIG. 17 may comprise a step 210 of deploying a fixation tray holding a flowable or malleable material over one or a plurality of teeth, the fixation tray having at a least a portion such as side walls configured to flex under stress, and a top portion connecting them and having extra flexible arm extensions inward-facing to urge the flowable or malleable material against the one or more teeth. For example, arm extensions 32, 34 may extend from a portion of side walls 22, 24 (or side portions of housing 20a) and in some cases from a free end, or from a point adjacent to a free end, of each of the side walls of the fixation tray 20, and the arm extensions 32, 34 may be inward-directed (and may be inclined) to urge the flowable or malleable material against the one or the plurality of teeth.

Step 220 of method 200 may comprise locking the fixation tray such as by deploying a locking wedge 40 over the fixation tray 20, for example to grip the fixation tray 20, for example to limit a movement of the side walls of the fixation tray. Step 230 may involve allowing the flowable or malleable material to harden into a rigid state that is crisp or brittle. The flowable or malleable material in some case flows into spaces 21 in housing 20a of tray 20 so that when it hardens it locks into the tray 20. Method 200 may include an additional step of performing the surgery while system 10, including tray 20 and lock 40, remain in place in a sturdy and stable position without regard to forces exerted on system 10.

Step 240 may comprise unlocking the lock or removing the locking wedge and then removing the fixation tray by exerting a force on an element of the fixation tray such as by rotating a pole or other element in a cavity of the fixation tray such as its top portion 26, thereby generating pressure against the housing 20a which causes at least portions of the housing 20a to flex (the portions may be sides that include arm extensions 32, 34) and which may causes breakage of the material, which allows dislodging the fixation tray from the plurality of teeth.

Method 200 may include a further step of redeploying the fixation tray holding new flowable or malleable material on the one or a plurality of teeth such that the fixation tray regains the same spatial position relative to the one or more plurality of teeth (or jaw bone). Method 200 may include a further step of allowing the new flowable or malleable material to harden and then redeploying the lock over the redeployed fixation tray so that the fixation tray (and lock) retains its same spatial position relative to the one or more plurality of teeth (or jaw bone).

Figure 18:
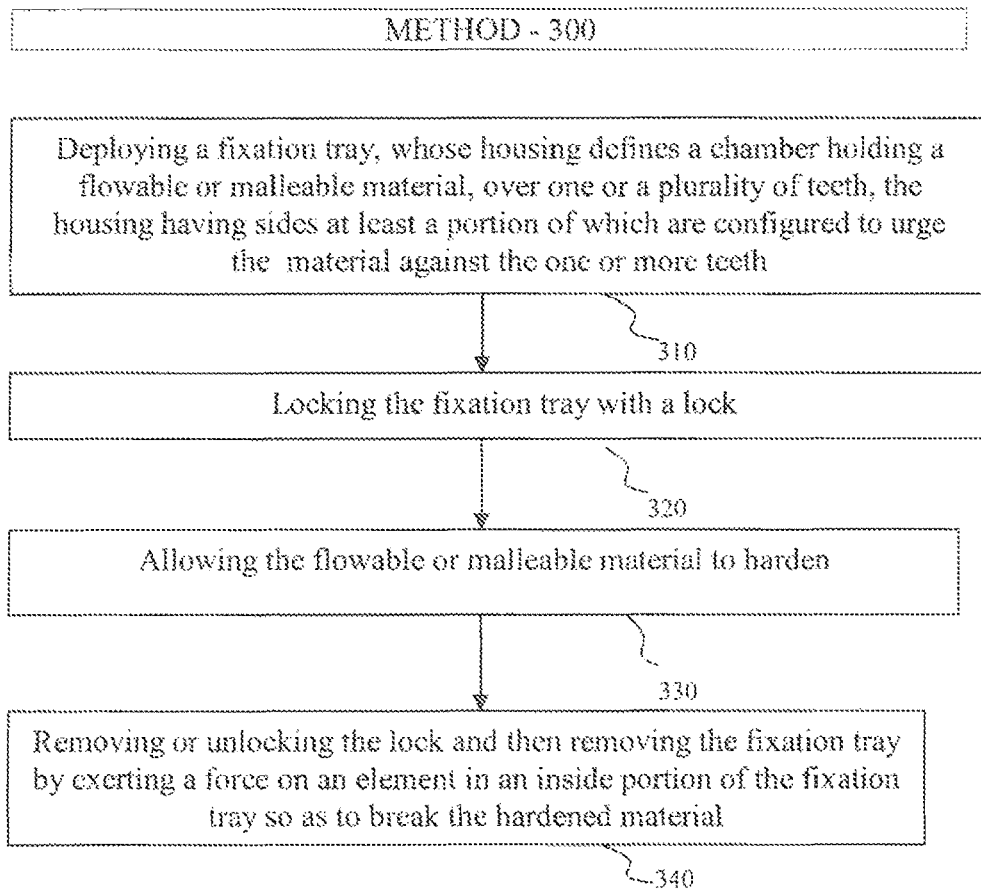
FIG. 18 is a flow chart of a method, in accordance with an embodiment of the invention.

A flow chart of another method 300 is shown in FIG. 18. It includes a step 310 of deploying a fixation tray holding a flowable or malleable material over one or a plurality of teeth, the fixation tray having somewhat side walls configured to urge the flowable or malleable material against the tooth or teeth for example using any mechanism described above with respect to system 10 including for example either extra flexible inwardly facing arm extensions 32, 34 or using inwardly facing steps 23a, 23b. Locking the fixation tray using a lock on the tray or by deploying a locking wedge over the fixation tray may comprise a step 320 of method 300. Allowing the flowable or malleable material to harden is step 330. The flowable or malleable material in some case flows into spaces 21 in housing 20a of tray 20 so that when it hardens it locks into the tray 20. Method 300 may include an additional step of performing the surgery while system 10, including tray 20 and lock 40, remain in place in a sturdy and stable position without regard to forces exerted on system 10. Step 340 may comprise unlocking the lock such as by removing the locking wedge and then removing the fixation tray by exerting a force on an element in a cavity of the fixation tray so as to break the hardened material.

Method 400 may comprise a step 410 of deploying a fixation tray holding a flowable or malleable material over one or more teeth, the fixation tray 20 having a housing 20a defining a chamber 25 and having a mechanism to urge the material against the one or more teeth. Step 420 may comprise locking the fixation tray 20 to reduce or eliminate its freedom of movement. Step 430 may comprise allowing the material to harden and performing the guided surgery while the tray 20 and lock 40 remain in place in a sturdy and stable position. Step 440 may comprise removing or unlocking the lock 40 and then removing the fixation tray 20. Any suitable version of any of the elements described herein for system 10 may be used for that element in method 400.

By using a tray 20 in any of methods 100, 200, 300, 400 or system 10 having at least a portion configured to flex under stress, the system 10 is designed to break the hardened material when pressure is exerted for example by rotating an element such as pole 65 in cavity 62 of top portion 26 of tray 20. As a result of the tray 20 having a portion or portions configured to flex under stress exerted on the fixation tray 20 results in pressure being exerted against the hardened (previously flowable or malleable) material. This breaks the hardened material and this hardened material comes off the teeth when the fixation tray 20 is dislodged. If the tray 20 were rigid it may simply take out the whole tooth or teeth. Since for stability reasons, system 10 fills an undercut of the plurality of teeth, there is no option to realistically just pull system straight up vertically.

As noted, connector 60 can be connected to or can itself be a registration body used in mating the CT coordinates and the real-world coordinates for the guided dental surgery. Accordingly, in an embodiment of the invention, method 500 of registration includes a step of performing a computed tomography (CT) scan of the patient's teeth without the system 10 being attached to the teeth. Step 520 comprises deploying any version of system 10 over one or a plurality of teeth (including tray 20 holding flowable or malleable material and including lock 40) so that system 10 is firmly attached to the one or a plurality of teeth and such that a connector 60 is also rigidly attached to system 10 such as by rigid attachment to tray 20 of system 10 (connector 60 is typically outside or mostly outside the patient's mouth). Step 530 involves performing registration by taking a tracking device (used in conjunction with the guided dental surgery) and touching it along the one or plurality of teeth.

In another embodiment of the invention, method 600 of registration includes a step 610 of deploying any version of system 10 over one or a plurality of teeth (including tray 20 holding flowable or malleable material and including lock 40) so that system 10 is firmly attached to the one or a plurality of teeth and doing so such that connector 60 is also rigidly attached to system 10 such as by rigid attachment to tray 20 of system 10 (connector 60 is typically outside or mostly outside the patient's mouth). Step 620 comprises performing a computed tomography (CT) scan of the one or the plurality of the patient's teeth after deployment of the tray 20 and lock 40 and connector 60. Step 630 comprises performing registration by taking the tracking device (used in conjunction with the guided dental surgery) and either (i) touching it along points of the connector 60 to register the connector 60 or (ii) simply rigidly attaching it (the tracking device) to the connector 60 to register the connector 60 since the dental surgery navigation system's software deduces the coordinates of the connector 60 from the coordinates of the tracking device to which it is rigidly attached.

These two versions of the registration process (500, 600) can also be combined with any or all of the steps of methods 100, 200, 300, 400, 700. As such, the step of removing the lock and tray (and/or allowing the material to harden) can be omitted from the list of steps of the registration method in some versions.

In one embodiment of the invention, a stable affixation system for guided dental implantation, comprises a fixation tray 20 having a housing 20*a* that defines a chamber 25 configured to house a flowable or malleable material and be placed over one or a plurality of teeth of a person during guided dental implantation surgery, the flowable or malleable material configured to harden into a crisp or brittle material so as to conform to a contour of the one or the plurality of teeth, the housing having a mechanism configured to urge the flowable or malleable material (and/or when it is already hardened) toward the one or the plurality of teeth. The system 10 also comprises a lock 40 or locking wedge 40 configured to lock tray 20 or be positioned on or over the fixation tray 20 so as to reduce or eliminate a freedom of movement of housing 20*a*. Housing 20*a* may include a mechanism configured to join the flowable or malleable material, once hardened, to housing 20*a* such that a greater separation force is required to separate the flowable or malleable material, once hardened, from the housing, than a separation force required to separate the flowable or malleable material from the one or the plurality of teeth.

The housing 20*a* may include a portion configured to flex upon stress. For example, housing 20*a* may have one or more recesses (as described above) and in some versions, locking wedge may include one or more corresponding projecting members. In some versions, locking wedge 40 includes a first locking wedge side wall 42 thicker than a first side wall 22 of housing 20*a* and a second locking wedge side wall 44 thicker than a second side wall 24 of housing 20*a*.

Housing may have sides at least a portion of which are configured to flex under stress. For example, side walls 22, 24 may flex outwardly under stress. For example, free ends of side walls 22, 24 may spread outwardly under stress. In some case, the further a portion of side walls 22, 24 is from a top portion 26 of housing 20*a*, the more that portion of the sides spreads outwardly under stress (for example due to a clamping or holding force at or near the top portion 26 of housing 20*a*).

In some embodiments, housing 20*a* has a mechanism configured to hold at least part of a tracking element and a mechanism configured to exert a force or a stress such as shear stress on the housing and/or on the crisp or brittle material so as to break at least a portion of the crisp or brittle material and dislodge the fixation tray from the one or the plurality of teeth. When the force is applied, the portion or portions of housing 20*a* configured to flex may then flex making it easier to cause stress on the hardened material and easily dislodge tray 20.

For example, the force may be applied from inside of tray 20. In one implementation, housing 20*a* has a cavity 62 configured to receive a tracking element or a handle of a tracking element. Cavity 62 may also be configured to receive an element (such as a pole 65 of a connector 60 of the tracking device) configured to exert a force or stress such as shear stress on the housing 20*a* (or a portion of housing 20*a* or on side walls of housing 20*a*) and/or on the hardened material so as to break at least a portion of brittle material and thereby dislodge the fixation tray 20 from the one or the plurality of teeth.

The mechanism for customizing the system 10 to the individual patient's teeth in order to facilitate rapid placement of the system 10 may be implemented, as seen in FIG. 15, in certain embodiments, by customizing the housing to the individual patient's teeth. This is implemented in some cases by the flowable or malleable material and by providing housing 20*a* of fixation tray 20 with a pair of inwardly directed arm extensions 22, 24 or inwardly directed steps 23*a*, 23*b* configured to urge the flowable or malleable material against the one or the plurality of teeth (including after such material hardens into a rigid state).

Figure 36:
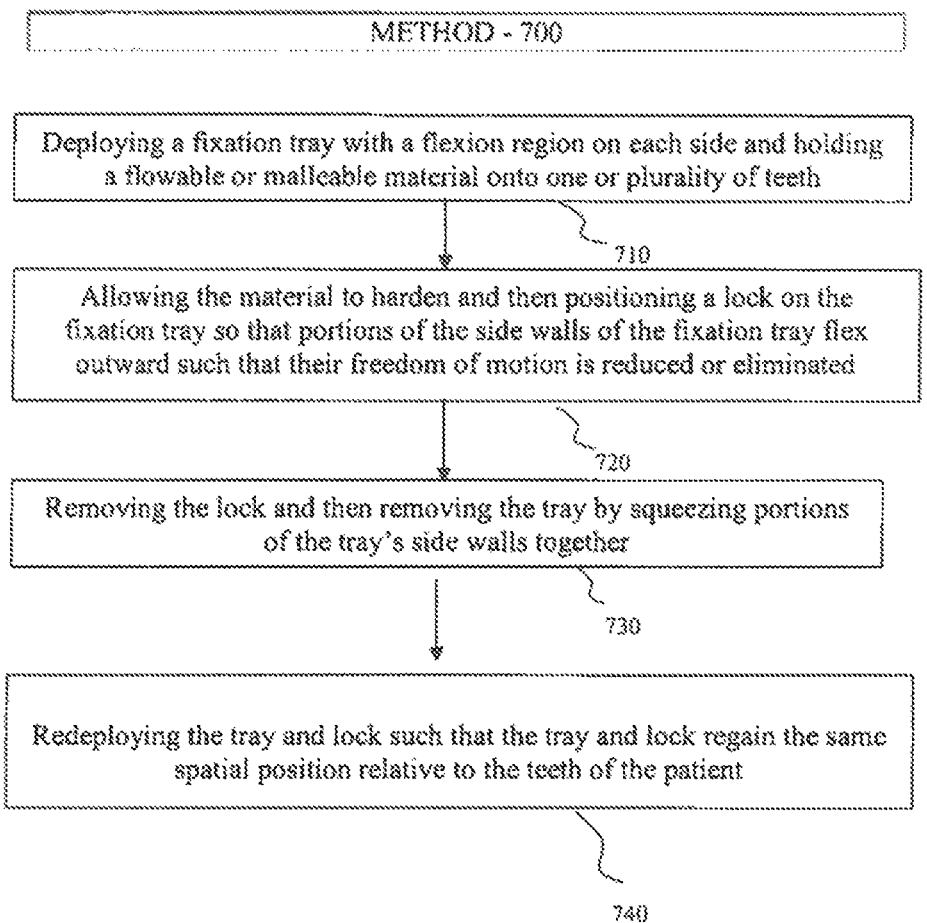
FIG. 36 is a flow chart of a method, in accordance with one embodiment.
Figure 39A:
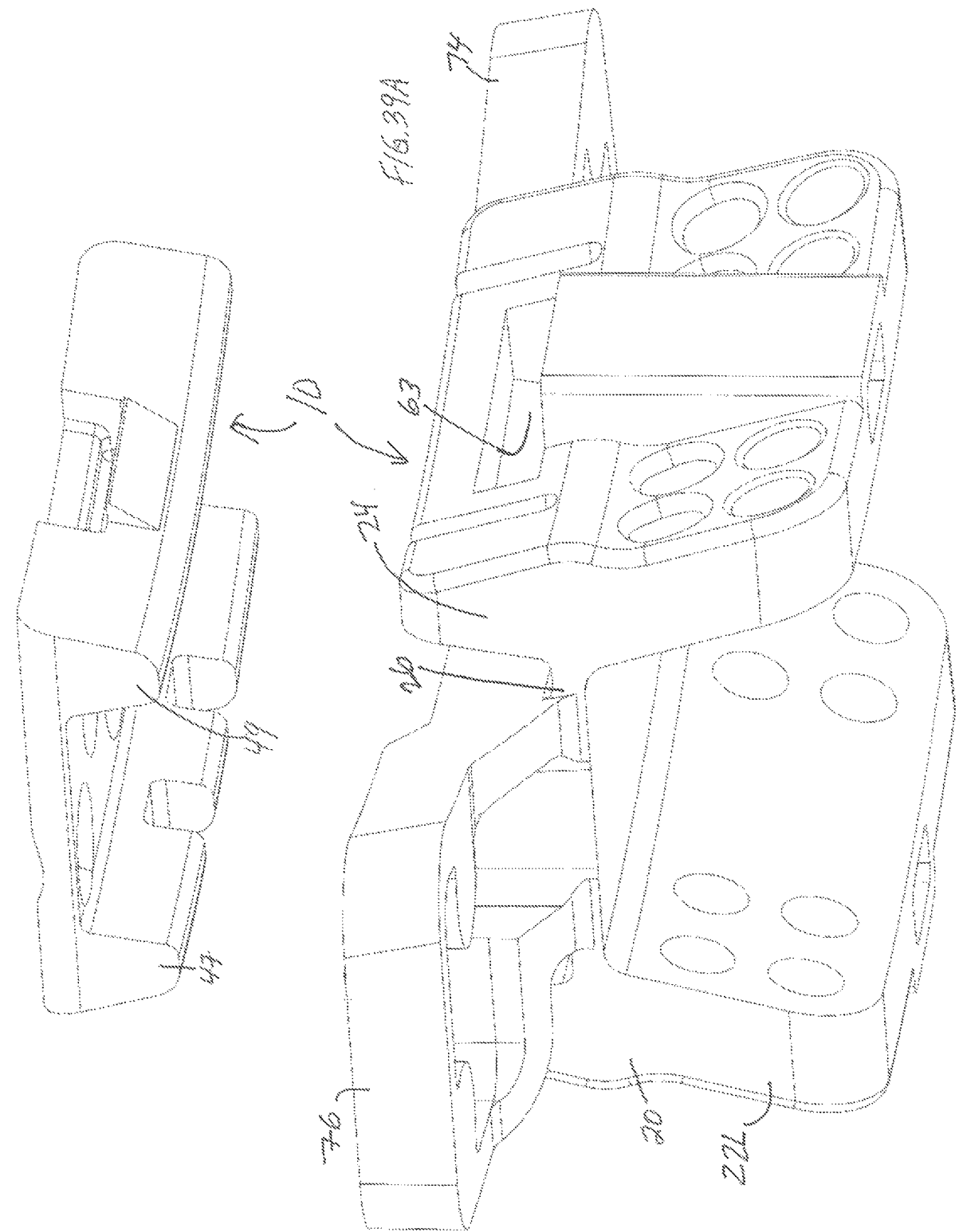
FIG. 39A is an exploded view of the winged fixation tray of FIG. 37 and lock of FIG. 38 from the front and right side, in accordance with one embodiment.
Figure 39B:
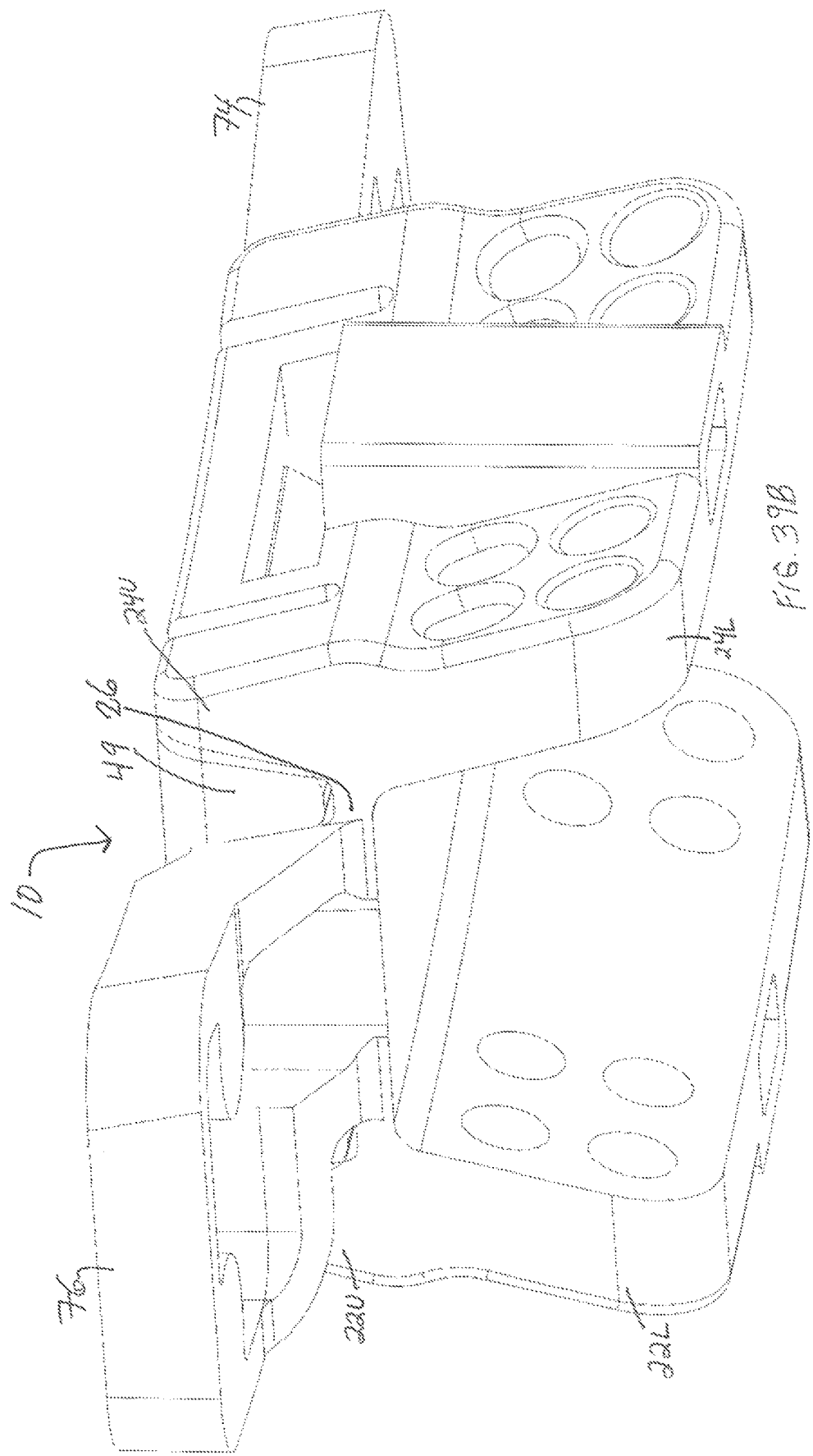
FIG. 39B is a perspective view of the winged fixation tray of FIG. 37 and lock of FIG. 38 fitted together, in accordance with one embodiment.
Figure 41:
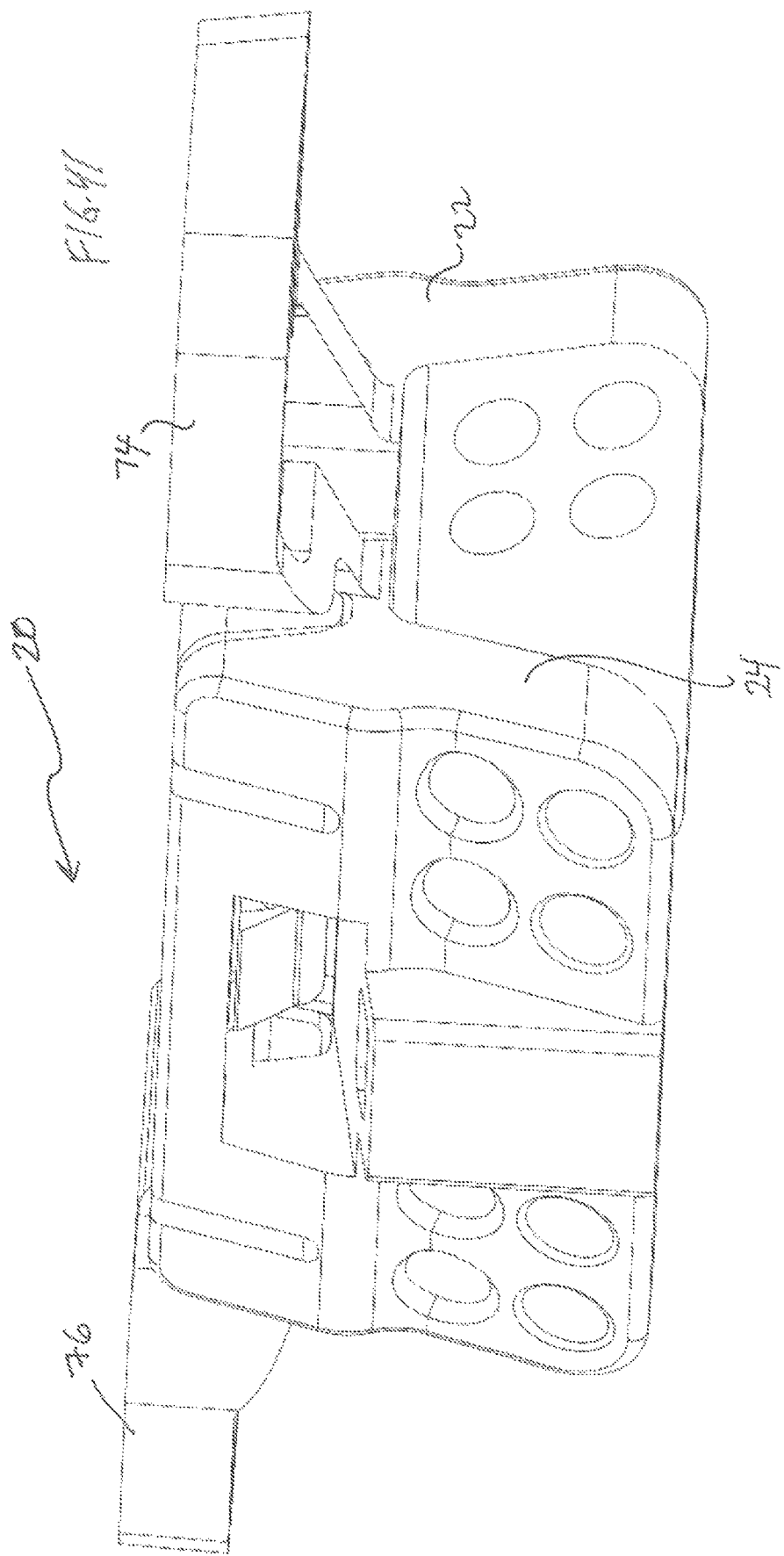
FIG. 41 is a perspective view of the winged fixation tray of FIG. 37 and lock of FIG. 38 from the front and left side, in accordance with one embodiment.
Figure 47A:
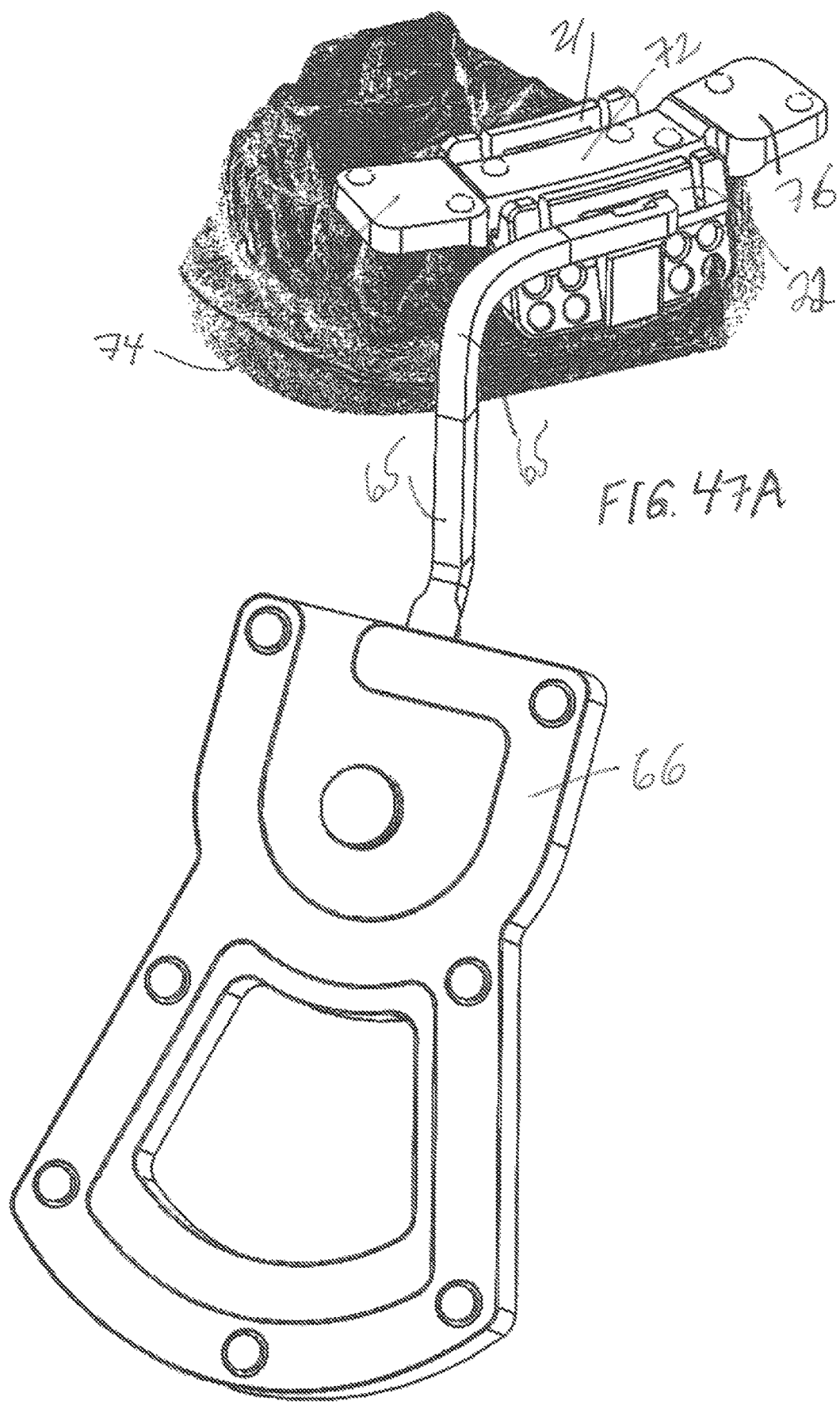
FIG. 47A is a view of a tray of an affixation system schematically shown placed on anterior teeth and including an attachment element and patient tracker, in accordance with one embodiment.
Figure 47B:
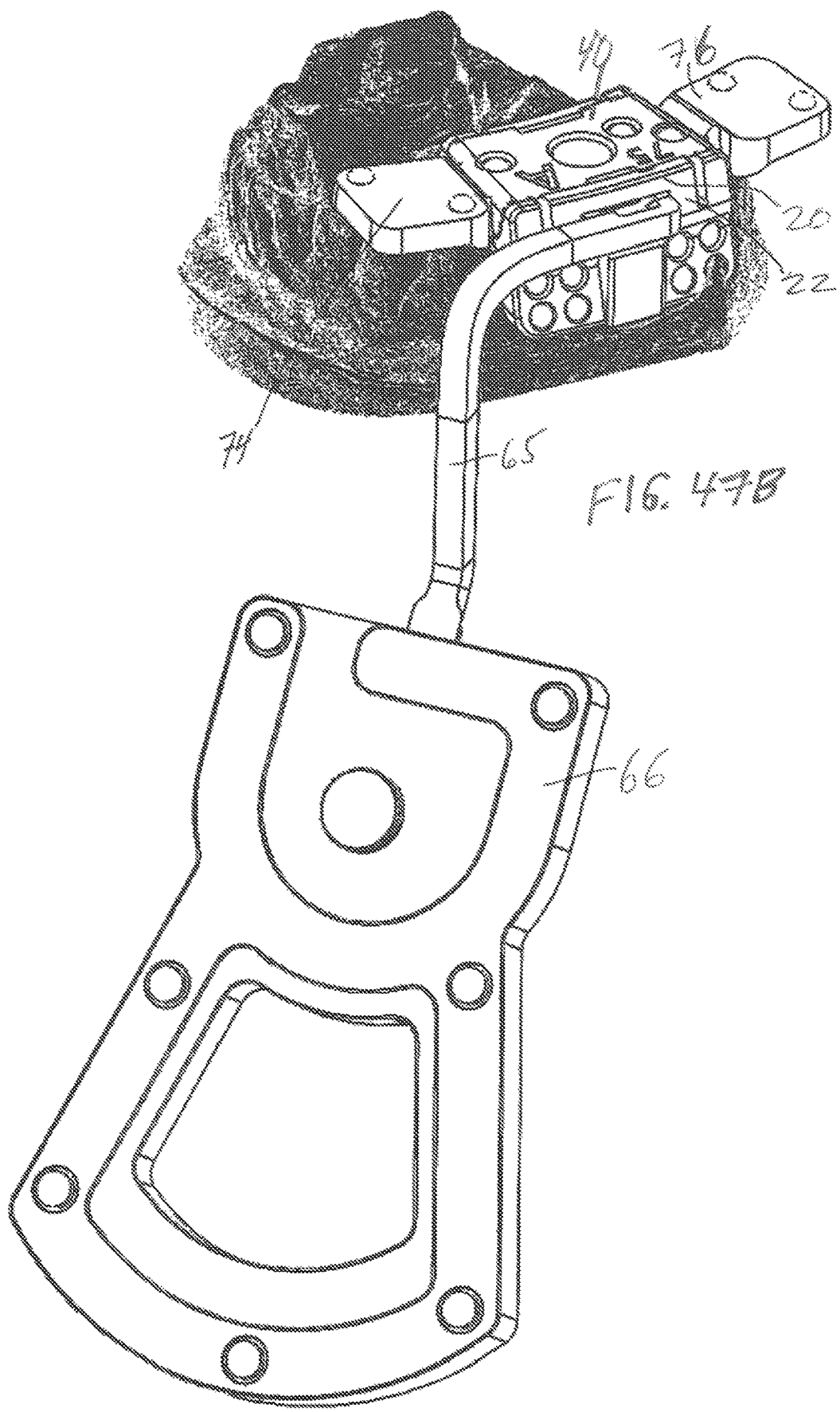
FIG. 47B is a view of a tray and lock (affixation system) schematically shown placed on anterior teeth and including an attachment element and patient tracker, in accordance with one embodiment.

As shown in FIG. 36, a further method 700 may generally include a step 710 of deploying a fixation tray 20 holding a flowable or malleable material over the teeth (one or a plurality, for example 1 or 2 or 3 or 4 or 5 or 6) on part of the arch of the patient, the fixation tray having a flexion region on each side. Method 700 may include a step 720 of allowing the material to harden and then positioning a lock 40 onto the fixation tray 20 so that portions of the side walls of the fixation tray flex outward such that their freedom of motion is reduced or eliminated. Method 700 may include a further step 730 of removing the lock 40 and then removing the tray by squeezing portions of the tray's side walls together. In some embodiments there may also be a further step 740 of redeploying the fixation tray 20 and then the lock 40 such that the fixation tray 20 and lock 40 regain the same spatial position relative to the teeth of the patient at the required level of precision demanded by the dental implantation surgery. In some embodiments, the system 10 achieves this repeatability by regaining the same spatial position to within about 0.5 mm.

In a more detailed implementation of method 700, in accordance with certain embodiments, method 700 may comprise a step of deploying a fixation tray 20 holding a flowable or malleable material over one or a plurality of teeth, the fixation tray 20 having a housing defining a chamber 25 configured to house the material and having side walls joined to a cross member 26 wherein each of the side walls includes an upper side portion 22U, 24U and a lower side portion 22L, 24L. Cross member 26 may include a flexion region on each side of the housing. In an unlocked position (when lock 40 is not positioned on fixation tray 20) a squeezing force on the upper side portions 22U, 24U (so as to urge them (22U, 24U) toward one another) flexes the lower side portions 22L, 24L outward (away from each other).

A further step of method 700 may involve allowing the flowable or malleable material to harden into a rigid but breakable state.

Method 700 may involve a further step of deploying a lock 40 over the fixation tray 20 by positioning a first and second side wall of the lock 40 so as to flex the upper side portions 22U, 24U of the housing outward, thereby flexing the lower side portions 22L, 24L inward, the lock 40 configured to reduce or eliminate a freedom of movement of the fixation tray 20. In the locked position, the side walls 22, 24 of the fixation tray 20 are configured to urge the flowable or malleable material, having hardened, against the one or the plurality of teeth.

A further step of method 700, may include removing the lock 40 and then removing the tray 20 by squeezing the upper side portions 22U, 24U so as to flex the lower side portions 22L, 24L outward.

Method 700 may include a further step of redeploying the fixation tray holding new flowable or malleable material on the one or a plurality of teeth such that the fixation tray regains the same spatial position relative to the one or more plurality of teeth (or jaw bone). Method 700 may include a further step of allowing the flowable or malleable material to harden and then redeploying the lock over the redeployed fixation tray so that the fixation tray retains its same spatial position relative to the one or more plurality of teeth (or jaw bone).

Thus, method 700 may achieve the feature of precise repeatability of the deployment of system 10.

Stable Winged Affixation System for Guided Dental Implantation

The term fiducial markers and the term fiducial members are used interchangeably and refer to something that is visible in an image such as a CT image and whose position and orientation are identifiable.

Another embodiment of the fixation system 10 (and another embodiment of the fixation tray 20) is presented. The winged embodiment, particular implementations of which are illustrated in FIGS. 37-47B and FIG. 50, (and particular implementations of a non-winged but similar version are illustrated in FIGS. 48-49), includes a central portion 70 of the housing 21 of the fixation tray 20 that includes a first wing and a second wing (or at least one wing in other versions such as shown in FIG. 51) that are each integrally attached to the central portion. Central portion 70 of housing 21 extends along a length of housing 21. The central portion 70 of housing 21 of the fixation tray 20 is not configured to flex. For example, it may be manufactured from a plastic or a metal whose rigidity level ensures this. In addition, as can be seen from FIG. 37, 38, 39A, 39B, 43A, 43B, 48, 49, the affixation system 10 is structured such that positioning lock 40 on tray 20 will not put pressure on central portion 70 since the projecting members 47, 49 of lock 40 are shaped to exert pressure on the respective side walls 22, 24 and rest on cross member 26 but do not exert pressure on central portion 70. This is true of all of the embodiments (winged and non-winged) in which central portion 70 is an element.

Further, the central portion 70 may be configured to receive one or a plurality of registration elements 80. The registration elements(s) comprise an element whose position and orientation can be identified in a CT and is immobile relative to the teeth during the CT and during the surgery. One example of a registration element is a fiducial marker. The registration member, for example the fiducial marker, may be attached to the tray 20 for example by having one or a plurality of recesses to accommodate the one or plurality of fiducial markers. In some implementations, the fiducial marker(s) themselves are included as part of the fixation tray 20 and as part of the affixation system. The fiducial marker(s) may be positioned on different portions of central portion 70, for example on the wings and/or into a body of the central portion of the housing that connects the wings. The one or a plurality of fiducial markers may be positioned in a recess on an exposed surface of the central portion or the fiducial marker(s) may be embedded wholly inside the central portion 70 in other embodiments. The fiducial marker(s) are used during the registration step of the guided dental implantation. The wings are specifically integrally attached to a portion of the housing that is not configured to flex since the whole purpose of the registration element(s) is to have their position and orientation identified on the CT (or other imaging process) screen as precisely as possible. The portion of the housing not configured to flex is the central portion 70 located between the side walls 22, 24 of housing 21.

Unless other specified, references to fiducial members or fiducial markers contemplates one or a plurality of them.

In one particular non-limiting embodiment, the registration elements, for example the fiducial marker(s), are fully integrated into the fixation tray as opposed to utilizing fiducial markers that are situated on a separate detachable element. In that way one does not have to be concerned about its repeatability, meaning how the detachable element fits into the tray 20 or whether it moves ever so slightly relative to the fixation tray 20. Any such relative movement distorts the calculations of the position and orientation of the registration elements made during the registration step in the guided dental implantation, in which the exact position and orientation of the fiducial members are registered.

In one version of the winged embodiment of the fixation system (or of the fixation tray) the registration element, for example fiducial markers, are either integrated into the body 72 of the central portion of the housing of the fixation tray or into the wings which are integrated to this body, so as to be part of the fixation tray itself. Thus, the fiducial members are immobile with respect to the teeth.

In another non-limiting version (for example that shown in FIG. 50) the registration element is removably attachable to the tray 20 in a way that is repeatable in its connection to the central portion 70. The central portion 70 of the affixation tray is itself immobile relative to the teeth that the tray 20 is placed on (either because of lock 40 being situated on tray 20 or even when lock 40 is not on tray 20 because the flowable or malleable material has hardened and is intact because the tray 20 has not been forcibly removed).

An additional advantage present in the winged fixation tray embodiment is that one or both of the wings can be snapped off or broken off or cut off. In this way, the same tray and lock affixation system is versatile enough to be placed on the left portion and on the right portion of the top arch and on the left portion and on the right portion of the bottom arch. In these four positions, whichever wing of the pair of wings ends up facing the rear of the mouth may need to be broken off in order to not interfere with something in the patient's mouth. A further advantage is that the wings increase the area available for placement of the fiducial markers. Consequently, a given number of the fiducial markers can be more distanced from one another. This increases the accuracy of the image navigation system because if a fiducial marker is too close to another fiducial marker the image navigation system is less accurate.

It is noted that the affixation system 10 also provides that there is no relative movement between the fixation tray 20 and the patient's teeth (i.e., that fixation tray 20 is immobile relative to the teeth). This is achieved using lock 40, the material that hardens and the central portion 70 that is not configured to flex (i.e., configured to not flex).

One implementation of the winged embodiment is a stable affixation system 10 for guided dental implantation, comprising a fixation tray 20 customizable to the patient including a housing 20a that defines a chamber configured to house a flowable or malleable material and be placed over one or a plurality of teeth of a person during the guided dental implantation. Fixation tray 20 (in any of the embodiments shown in FIG. 37 through FIG. 51) is configured to be placed over one or two or three or four or five or six teeth or over a portion of the patient's arch that spans 1-6 teeth. Typically, these would be consecutive adjoining teeth of an arch. In some embodiments, fixation tray 20 is configured to be placed over between 2 and 5 teeth, or over a portion of the arch spanning a row of 2 or 3 or 4 or 5 teeth. In some embodiments, fixation tray 20 is configured to be placed over 1 to 6 adjoining teeth or 2 to 6 adjoining teeth or 2 to 5 adjoining teeth. In some embodiments, system 10 and in particular fixation tray 20, is configured to be placed over one or a plurality (for example two or three or four or five) of posterior teeth (or five posterior teeth plus an adjacent tooth). In other embodiments, system 10 and in particular fixation tray 20, is configured to be placed over one or a plurality (for example two or three or four or five or six) of anterior teeth.

In addition, in the winged embodiment, housing 20a may include a central portion 70 that is not configured to flex and housing 20a (as in other embodiments) may have side walls 22, 24, each side wall 22, 24 having an upper side portion 22U, 24U configured to flex when lock 40 is not positioned on fixation tray 20, and a lower side portion 22L, 24L configured to flex when lock 40 is not positioned on fixation tray 20. When lock 20 is not positioned on the fixation tray 20, a squeezing force on the upper side portions 22U, 24U of respective sides 22, 24 of housing 21 may flex the lower side portions 22L, 24L of respective sides 22, 24 outwards. Central portion 70 is situated between side walls 22, 24.

As shown in FIG. 37 to FIG. 46A, central portion 70 may include a body 72, a first wing 74 extending outward from a first end of the body and may also include a second wing 76 extending outward from a second end of the body so that each of the wings extends an overall length of the housing 20a. Central portion 70 may be situated between side walls 22, 24 of housing 20a. In some version the wings can be said to extend out of a front and out of a rear of the body 72, although the labels "front" and "rear" would change depending on whether the tray 20 is placed over teeth on the left side or on the right side of the mouth (for a particular arch). As shown in FIGS. 37, 39A, 39B cross member 26 connects each of side walls 22, 24 to central portion 70. In any embodiment that includes central portion 70, central portion 70 is not configured to flex as a result of any flexing of side walls 22, 24.

In some embodiments, the number of wings exceeds two. For example, one of the wings, 74, 76 may be divided into two or more parts. In another embodiment, the number of wings is just one, as shown in FIG. 51.

Central portion 70 (including the wings 74, 76 and/or body 72) may be configured for receipt of one or a plurality of registration elements such as fiducial markers. In one implementation, central portion 70 may have carved into it, for example into a surface thereof, in one non-limiting example a top surface thereof, (or for example in other embodiments into a side surface thereof) a plurality of recesses 77 shaped for receiving and fixedly holding a fiducial marker 80 such that the fiducial marker remains at least partially exposed, as shown in FIG. 40B, 40C, 42B, 43B, 44B, 44C or such that the registration elements are able to be localized in a tracking coordinate system for the registration process. Each recess 77 may be configured for receipt of a fiducial marker 80. Recesses 77 are configured such that fiducial markers 80 may be fixedly placed or embedded in the recesses of central portion 70 such that the fiducial members 80 are at least partially exposed, and continued to be at least partially exposed even when lock 40 is positioned over tray 20. In other embodiments, for example where a fully automatic registration process is being relied upon, there may be no recesses and there may be no fiducial markers integrated into tray 20, or it may be the case that there are recesses 77 but the recesses 77 are not necessarily shaped to ensure that fiducial markers 80 are at least partially exposed (with or without lock 40).

Fiducial markers 80 are configured to be visible on an image of the fixation tray 20 obtained using a dental imaging process (such as a CT) and immobile relative to the fixation tray 20. The minimum number of fiducial markers 80 embedded in central portion 70 is one, but there would typically be more. In one non-limiting embodiment shown in FIG. 37 to FIG. 46E, there are seven (three in body 72 and two each on wings 74, 76).

As seen in FIGS. 40B, 40C, 42B, 43B, 44B, 44C, the body 72, the first wing 74 and the second wing 76 each include at least one of the fiducial markers 80, or in other cases at least two fiducial markers. One benefits from utilizing the surface area, particularly the top surface, of central portion 70 to spread out the fiducial markers 80 (for improved accuracy of the registration process as noted above) but in theory some portions of central portion 70 can have more fiducial markers than others and in theory each wing 74, 76 can have fiducial markers without body 72 having any or in theory one of the wings and body 72 can have all of the fiducial markers and the other wing can have none. In the non-limiting embodiment shown in FIG. 37 to FIG. 46E, for example, each wing 74, 76 has two apertures and is configured to accommodate two fiducial markers 80 and body 72 of central portion 70 has three apertures and is configured to accommodate three fiducial markers 80. The circumstances under which only one fiducial member 80 may be needed would be if such fiducial member 80 were uniquely enough shaped.

One or both of the wings, for example whichever wing of the pair of wings ends up facing the rear of the mouth, may be configured to be broken off in order to not interfere with something in the patient's mouth. The breaking can be a manual snapping off or it can be configured so that it can be cut off for example using a cutting instrument.

As seen in FIG. 43A, FIG. 43B and FIG. 45E, wings 74, 76 (or in some embodiments all the wings if there are more than two) may be elevated relative to the body 72 of the central portion 70 along a height dimension of housing 21. The height dimension runs in the direction from the lower teeth to the upper teeth (or vice versa) or in a general direction from the gumline of a lower tooth to the top of that lower tooth. The width of the housing runs from a side wall 22 to a second side wall 24 (or runs from a buccal side wall to a lingual side wall). The lengthwise direction runs substantially from an end of the housing to another end of the housing (which may be said to be generally corresponds to the direction one goes from one posterior portion of one posterior tooth to the anterior portion of its adjacent posterior tooth which would represent the length of two teeth, which is only one example of how many teeth the tray 20 or system 10 could cover). Accordingly, a top surface of wings 74, 76 are higher than a top surface of body 72 of central portion 70 when tray 20 is viewed from the side (or from the side and the top) such as in FIG. 43A and FIG. 45E.

System 10 also includes a lock configured, when positioned on the fixation tray, to reduce or eliminate a freedom of movement of the fixation tray. In implementations where fiducial members 80 are integrated with tray 20, lock 40 is configured with apertures 48 that are positioned on lock 40 such that fiducial markers 80 of tray 20 are still exposed when lock 40 is positioned on fixation tray 20, as shown in FIGS. 40C, 42B, 44B. In particular, this applies to the fiducial markers 80 on the body 72 of central portion 70 since lock 40 is not positioned on wings 74, 76 so fiducial members 80 on wings 74, 76 are exposed anyway. Rather lock 40 is configured to confine the parts of housing 21 that are configured to flex, such as sides 22, 24.

As shown in FIG. 40B, 40C, 42B, 43A, 43B, 44A, 44B, 44C, 46D, 46E, a top surface 50A of the lock 40 may have apertures 51, 52, 53 so that when the lock 40 is positioned on the fixation tray 20 these apertures 51, 52, 53 of lock 40 allow any fiducial members 80 that are embedded in the fixation tray 20 to remain at least partially exposed even when lock 20 is positioned over fixation tray 20 (which exposure is needed during a registration step of the guided dental implantation). This assumes that the registration step is not fully automated because if it is then no fiducials would be integrated with the tray 20 and no recess 77 would be needed and no apertures 51, 52, 53 etc. in lock 40 would be needed—although it is possible for the simplicity of manufacture that there still would be recesses and apertures.

As seen from FIGS. 40B, 40C, 42B, 43B, 44C, 47, registration elements 80, such as fiducial markers 80, may be substantially spherical. But this is not a limiting property. The fiducial markers 80 can also be rectangular, pentagonal, polygonal, trapezoidal or another shape. In order to hold the registration elements 80 securely and immobile, the recesses 77 on central portion 70 may be deep enough to hold a substantially spherical fiducial marker 80 (if that is the shape of the fiducial marker), for example a little more than half a height of the fiducial marker 80 so that the fiducial marker 80 can snap into the recess 77.

Another option, as show in FIG. 48, is that one or more fiducial markers 80 may be situated on or in an attachment element 82 extending from housing 21, and in particular from the nonflexing portion of housing 21, namely central portion 70, for example from a top surface of body 72 of central portion 70. The attachment element 82 may be removably attached to central portion 70. Fiducial(s) 80 may be snapped into and snapped out of attachment element 82 or may be embedded therein during manufacturing of attachment element 79. Alternatively, element 82 can be the registration elements such as the fiducial marker—in that case element 80 would not be needed as a separate element. Attachment element 82 may be referred to as a fiducial attachment element 82 to distinguish it from any attachment element 65, for example pole 65 configured to connect to a side of central portion 70 and configured to hold a patient tracker 66 on its other end.

Attachment element 65 have be cylindrical or may have a rectangular or any other suitable cross-section or shape.

In the winged embodiment, the affixation system 10 may further comprise a pole 65 (seen in FIG. 47A, FIG. 47BB) or other attachment element 65 such as an elongated attachment element, configured for attachment to the central portion 70 through a cavity 63 in a side 24 of housing 21 (which provides access to a central portion cavity 163), since pole 65 or other attachment element 65 has to be immobile relative to the teeth when tray is locked in position. Pole 65 or other attachment element 65 is also configured to connect to a patient tracker 66 at its other end. The location of cavity 63 on the side of housing 21 (in the drawings it is on the side wall 22 of housing 21) can be seen for example in FIG. 40A through FIG. 44C and FIG. 45A, FIG. 45E. This positioning of cavity 63 in side wall 22 and central portion cavity 163 for access by the pole 65 or attachment element 65 is in contrast to previously discussed embodiments where the pole 65 may be configured to fit into a cavity 62 at an end of the tray 20 (see FIG. 1 or FIG. 24) as opposed to at a side of the tray 20. The positioning of cavity 63 and central portion cavity 163 so as to provide this access on the side of housing 21 (for example on the side of side wall 22) is due to the presence of the wings projecting from the ends of the tray 20 in the winged embodiment. Moreover, as seen in the non-limiting example of FIG. 40A through FIG. 44C and FIG. 45A, FIG. 45E, cavity 63 may be configured such that pole 65 or attachment element can access cavity 63 horizontally across a width of tray 20.

Cavity 63 is merely a passageway for pole 65 or other attachment element 65 to traverse until it reaches a deeper central portion cavity 163 defined by at least one central portion cavity wall 163A in a side of central portion 70, as shown in FIG. 50. The connection to the side of central portion 70 is necessary for secure affixation of the pole 65 or other attachment element 65 because central portion 70, as opposed to side walls 22, 24 (and in particular side wall 22 which is the side of tray 20 that happens to have been selected for access), is not configured to flex. In any event, since central portion 70 is not configured to flex, the connection between pole 65 (or another differently shaped attachment element 65) and the central portion cavity walls 163A that define central portion cavity 163 is rigid enough and secure to ensure that when pole 63 has been inserted into this central portion cavity 163 it is then held affixedly in central portion cavity 163 of the side of central portion 70 and in fact pole 63—and also any patient tracker 66 (FIGS. 47A, 47B) attached to this pole 65 or other attachment element 65—are each immobile relative to central portion 70 and also immobile relative to any fiducial member(s) 80 embedded (partially or totally) in a surface of central portion 70 or for that matter in a surface of any further rigid attachment element 82 (FIG. 48) that is in turn embedded (partially or totally) in central portion 70. The attachment element 65 or pole 65 is in place fixedly such that it cannot wiggle within central portion cavity 163A.

Fixation tray 20 also may have a cavity 67 that may be substantially vertical (or some embodiments within 30 degrees of vertical) for insertion of an instrument to prod the lock 40 off the tray 20 and to prod the tray 20 off the teeth.

In some embodiments of the winged embodiment, the system 10 (or the tray 20) does not include any registration elements 80. For example, the dental surgeon or practitioner may sometimes use the registration elements and other times effectuate the registration process without the registration elements (by for example using a registration instrument to go over/trace the surfaces of the teeth while the camera tracks the positions of many dots in three dimensions and marks the positions in a computer program and then algorithmically finding a match of that pattern on the CT image of the teeth).

The winged embodiment may also be described as a version of the fixation tray 20 itself, for example, a fixation tray 20 configured to be used in a stable affixation system 10 for guided dental implantation. In that case, in some embodiments, the fixation tray 20 is customizable to the patient and includes a housing 21 that defines a chamber 25 configured to house a flowable or malleable material and be placed over one or a plurality of teeth of a person during the guided dental implantation. The housing 21 may include a central portion 70 that is not configured to flex and having side walls 22, 24, each side wall 22, 24 having an upper side portion 22U, 24U configured to flex and a lower side portion 22L, 24L configured to flex (for example without a lock such as lock 40 positioned on the fixation tray 20 a squeezing force on the upper side portions 22U, 24U flexes the lower side portions 22L, 24L outward), the central portion 70 including a body 72, a first wing 74 extending outward from a first end of the body and a second wing 76 extending outward from a second end of the body so that each of the wings 74, 76 extend an overall length of the housing, the central portion 70 having carved into a surface thereof, for example a top surface thereof, a plurality of recesses 77, each of the recesses shaped for fixedly receiving and securely holding a registration element 80 that remains at least partially exposed or such that the registration element(s) are able to be localized in a tracking coordinate system for the registration process.

The structure of the components of the fixation tray 20 (or components affixed to tray 20) in the winged embodiment of fixation tray 20 (as opposed to the winged embodiment of the whole system 10 including lock 40) may be any version or structure of tray 20 that has been described for the tray 20 forming part of the winged affixation system 10. For example, anything described with respect to the central portion 70 of the tray 20 used in the affixation system 10 that is winged or that has been described as including a central portion 70 is equally applicable as an option in the embodiments comprising only the affixation tray 20 (without the lock 40) where such tray 20 has a central portion 70—and vice versa. The same is true of the side walls 22, 24 and of the one or more fiducial members 80. Likewise, such tray 20 (of the embodiments comprising only the affixation tray 20 without the lock 40) may include any feature described for the tray 20 of system 10—and vice versa.

The drawings (FIGS. 37-47B and 51) show the winged embodiment or non-winged embodiment (FIGS. 48-49) in the context of the fixation system 10 or tray 20 that is configured mainly for posterior teeth. However, the winged system 10 or winged tray 20 (or non-winged versions shown in FIGS. 48-49) may also be configured mainly for the anterior teeth. In this case, the structure of the tray 20 and lock 40 would be adapted based on the tray for such anterior teeth shown in FIGS. 30-33B except for the changes made to create the embodiments shown in FIGS. 37-51 for the posterior teeth including for example the addition of one or more wings 74, 76, if any, the recesses 77, if any, the apertures 51, 52, 53 etc., of lock 40, if any, the presence of a registration element 80 or a detachable fiducial attachment element containing fiducial markers 80. In addition, the location of the cavity 63 and central portion cavity 163 would be on the side of the tray 20 as opposed to on an end of the tray 20 for accommodation of a pole or other attachment element. All of the options or versions of these elements described in the context of the posterior teeth are applicable to the version with the anterior teeth. Moreover, for the version configured for use on the anterior teeth, a wing that may need to be cut off or snapped off to avoid interfering with something in the mouth may be a wing that is not facing a rear of the mouth.

In some embodiments of affixation system 10, and of fixation tray 20, as shown in FIG. 49, there are no wings on tray 20. In some cases, this is because the number of registration elements 80 situated on central portion body 72 is enough. In some other embodiments this can be because a fully automatic registration process is used in which an algorithm determines the position and orientation of fiducials 80 without the registration element 80 having to be exposed or without the fiducial(s) even being situated on tray 20. For example, as shown in FIG. 48, one or a plurality of registration elements such as fiducials 80 are situated on an attachment element 86 removably attachable to central portion 70. In the non-limiting example shown in the figure, attachment element 82 is seen jutting out or extending from central portion 70. Alternatively, attachment element 82 is itself used as the registration element, for example because of some shape or design that lends itself to being localized/detectable in the CT.

FIG. 50 is a view from the side and slightly from the top showing a larger view of the central portion cavity 163 (defined by central portion cavity walls 163A) relative to FIG. 45A. It shows wings but its depiction of the central portion cavity 163 applies equally to a non-winged embodiment.

Accordingly, one embodiment is a stable affixation system 10 for guided dental implantation, comprising a fixation tray 20 customizable to the patient including a housing 21 that defines a chamber 25 configured to house a flowable or malleable material and be placed over one or a plurality of teeth of a person during the guided dental implantation. System 10 includes a lock configured, when positioned on the fixation tray, to reduce or eliminate a freedom of movement of the fixation tray 20.

The housing 21 may include a central portion 70 that is not configured to flex (for the reasons previously stated with respect to the winged embodiment) and having side walls 22,24, each side wall 22, 24 having an upper side portion 22U, 24U configured to flex when the lock 40 is not positioned on the fixation tray 20 and a lower side portion 22L, 24L configured to flex when the lock 40 is not positioned on the fixation tray, wherein when the lock 40 is not positioned on the fixation tray a squeezing force on the upper side portions 22U, 24U flexes the lower side portions 22L, 24L outward.

One of the side walls 22, 24, for example side wall 22, may have a cavity 63 on the upper portion thereof 22U, for passage of an attachment element 65 (in one non-limiting example such as a pole 65), a side of the central portion 70 having a central portion cavity 163 defined by central portion cavity walls 163A for receipt of the attachment element 65 such that once received the attachment element 65 is affixed to the central portion 70 in an immobile manner. In this generalized embodiment, it is not necessarily required to have a registration element or recesses to hold such an element or for there to be apertures on a lock, or wings.

The affixation system 10 may also comprise one or a plurality of fiducial members 80 either entirely embedded within the central portion 70 or else affixed in a recess on an exposed surface of the central portion 70.

In some versions, central portion 70 may have a surface such as top surface into which may be carved one or a plurality of recesses shaped for receiving and fixedly holding one or a plurality of registration elements, such as fiducial members.

In any embodiment having a central portion 70, when the fixation tray 20 is placed on the one or the plurality of teeth, the system 10 is configured such that the central portion 70 is immobile with respect to the one or the plurality of teeth if either the lock 40 is positioned on the fixation tray 20 or even if the lock 40 is not so positioned if the flowable or malleable material has hardened against the one or the plurality of teeth.

Another embodiment with the central portion 70 is the tray 20 of such an affixation system 10. Accordingly, an embodiment is a fixation tray 20 configured to be used in a stable affixation system for guided dental implantation, the fixation tray 20 customizable to the patient and including a housing 21 that defines a chamber 25 configured to house a flowable or malleable material and be placed over one or a plurality of teeth of a person during the guided dental implantation, the housing 21 including a central portion 70 that is not configured to flex and having side walls, each side wall having an upper side portion configured to flex and a lower side portion configured to flex, wherein a squeezing force on the upper side portions 22U, 24U flexes the lower side portions 22L, 24L outward, one of the side walls 22, 24 having a cavity 63 on the upper portion thereof for passage of an attachment element 65, a side of the central portion 70 having a cavity 163 for receipt of the attachment element 65 such that once received the attachment element 65 is affixed to the central portion 70 in an immobile manner. In this generalized embodiment, the presence of a registration element 80, or of recesses 77 to accommodate a registration element 80 or the presence of wings is not necessarily required.

The fixation tray 20 may in some versions of this embodiment also further comprise one or a plurality of registration elements 80 either entirely embedded within the central portion 70 of housing 21 of tray 20 or else affixed in a recess 77 on an exposed surface of said central portion 70. The central portion 70 has a surface top surface (or in some other versions a side surface) into which may be carved one or a plurality of recesses 77 shaped for receiving and fixedly holding one or a plurality of registration elements such as fiducial members 80.

The features of different embodiments may be combined. For example, shapes or amounts of registration element such as fiducial members described with respect to one embodiment may be applicable to any other embodiment in which there is a presence of one or more registration elements such as fiducial members 80. Similarly, the physical structure of housing 21, or of sides 22, 24 thereof, or of central portion 70 described with respect to one embodiment are equally applicable to other embodiments unless otherwise specified to the contrary. The reasons given for central portion 70 not being configured to flex apply to all of the embodiments containing central portion 70.

In any embodiment, the materials used for the tray 20 and lock 40 or for one of them can include plastic or metal or any other material suitable for use in dentistry that meets the structural and other requirements described.

Non-limiting examples of the flowable or malleable material described herein include bisacryl, dental composite material or silicon-based material.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A stable affixation system for guided dental implantation, comprising:
    a fixation tray customizable to the patient including a housing that defines a chamber configured to house a flowable or malleable material and be placed over one or a plurality of teeth of a person during the guided dental implantation,
    a lock configured, when positioned on the fixation tray, to reduce or eliminate a freedom of movement of the fixation tray,
    the housing including a central portion that is not configured to flex and having side walls, each side wall having an upper side portion configured to flex when the lock is not positioned on the fixation tray and a lower side portion configured to flex when the lock is not positioned on the fixation tray,
    the central portion including a body, a first wing extending outward from a first end of the body and a second wing extending outward from a second end of the body so that each of the wings contributes to an overall length of the housing,
    the central portion having carved into a surface thereof one or a plurality of recesses shaped for receiving and fixedly holding one or a plurality of registration elements.

2. The affixation system of claim 1, further comprising the one or plurality of the registration elements fixedly held respectively in the one or plurality of the recesses such that the registration elements are visible on an image of the fixation tray obtained using a dental imaging process and immobile relative to the housing of the fixation tray and such that a position and orientation of the registration elements can be determined in a tracking coordinate system.

3. The affixation system of claim 1, wherein a top surface of the lock has apertures so that when the lock is positioned on the fixation tray the apertures of the lock allow any of the registration elements that are embedded in the fixation tray to remain fixed position.

4. The affixation system of claim 1, wherein the body, the first wing and the second wing each include at least one of the registration elements.

5. The affixation system if claim 1, wherein the body, the first wing and the second wing each include at least two of the registration elements.

6. The affixation system of claim 1, wherein each of the wings includes at least one of the registration elements.

7. The affixation system of claim 1, wherein the second wing is configured to be separated from the body by breaking or by cutting.

8. The affixation system of claim 1, wherein the wings are elevated relative to the body of the central portion along a height dimension of the housing.

9. The affixation system of claim 1, wherein the one or a plurality of registration elements are substantially spherical.

10. The affixation system of claim 1, wherein each of the recesses is shaped for receiving and fixedly holding the one or a plurality of registration elements such that the one or a plurality of registration elements remains at least partially exposed.

11. The affixation system of claim 1, wherein, without the lock positioned on the fixation tray, a squeezing force on the upper side portions flexes the lower side portions outward.

12. The affixation system of claim 1, further comprising a pole and wherein a side of the central portion has an opening for attaching to part of the pole, the pole also configured to connect to a patient tracker.

13. A fixation tray configured to be used in a stable affixation system for guided dental implantation, the fixation tray comprising:

the fixation tray customizable to the patient and including a housing that defines a chamber configured to house a flowable or malleable material and be placed over one or a plurality of teeth of a person during the guided dental implantation, the housing including a central portion that is not configured to flex and having side walls, each side wall having an upper side portion configured to flex and a lower side portion configured to flex, the central portion including a body, a first wing extending outward from a first end of the body and a second wing extending outward from a second end of the body so that each of the wings contributes to an overall length of the housing, the central portion having carved into a surface thereof one or a plurality of recesses shaped for receiving and fixedly holding one or a plurality of registration elements.

14. The fixation tray of claim 13, further comprising the one or plurality of the registration elements fixedly held respectively the one or plurality of the recesses such that the one or a plurality of registration elements are each at least partially exposed, said one or a plurality of registration elements configured to be visible on an image of the fixation tray obtained using a dental imaging process and immobile relative to the housing of the fixation tray.

15. The fixation tray of claim 13, wherein the body, the first wing and the second wing each include at least one of the one or a plurality of registration elements.

16. The fixation tray of claim 13, wherein the body, the first wing and the second wing each include at least two of the one or a plurality of registration elements.

17. The fixation tray of claim 13, wherein each of the wings includes at least one of the one or a plurality of registration elements.

18. The fixation tray of claim 13, wherein when the fixation tray is placed on the one or the plurality of teeth, the central portion is immobile with respect to the one or the plurality of teeth if either a lock is positioned on the fixation tray or if the flowable or malleable material has hardened against the one or the plurality of teeth.

19. The fixation tray of claim 13, wherein a position and orientation of the one or a plurality of registration elements is configured to be localized in a tracking coordinate system during a registration step of the guided dental implantation.

20. The fixation tray of claim 13, wherein the wings are elevated relative to the body of the central portion along a height dimension of the housing.

21. The fixation tray of claim 13, wherein the one or a plurality of registration elements are substantially spherical.

22. The fixation tray of claim 13, wherein a squeezing force on the upper side portions flexes the lower side portions outward when the tray is not limited by an external lock of the system.

23. The fixation tray of claim 13, wherein a side of the central portion is configured to attach to a pole that connects to a patient tracker.

24. The fixation tray of claim 13, wherein each of the recesses is configured to hold the respective one or a plurality of registration elements such that the one or a plurality of registration elements are able to be localized in a tracking coordinate system.

25. A stable affixation system for guided dental implantation, comprising:

a fixation tray customizable to the patient including a housing that defines a chamber configured to house a flowable or malleable material and be placed over one or a plurality of teeth of a person during the guided dental implantation, a lock configured, when positioned on the fixation tray, to reduce or eliminate a freedom of movement of the fixation tray, the housing including a central portion that is not configured to flex and having side walls, each side wall having an upper side portion configured to flex when the lock is not positioned on the fixation tray and a lower side portion configured to flex when the lock is not positioned on the fixation tray, wherein when the lock is not positioned on the fixation tray a squeezing force on the upper side portions flexes the lower side portions outward, one of the side walls having a cavity on the upper portion thereof for passage of an attachment element, a side of the central portion having a central portion cavity for receipt of the attachment element such that once received the attachment element is affixed to the central portion in an immobile manner.

26. The affixation system of claim 25, further comprising one or a plurality of registration elements either entirely embedded within the central portion or else affixed in a recess on an exposed surface of said central portion.

27. The affixation system of claim 25, wherein the central portion has a surface into which is carved one or a plurality of recesses shaped for receiving and fixedly holding one or a plurality of registration elements.

28. A fixation tray configured to be used in a stable affixation system for guided dental implantation, the fixation tray comprising:

the fixation tray customizable to the patient and including a housing that defines a chamber configured to house a flowable or malleable material and be placed over one or a plurality of teeth of a person during the guided dental implantation, the housing including a central portion that is not configured to flex and having side walls, each side wall having an upper side portion configured to flex and a lower side portion configured to flex, wherein a squeezing force on the upper side portions flexes the lower side portions outward, one of the side walls having a cavity on the upper portion thereof for passage of an attachment element, a side of the central portion having a central portion cavity for receipt of the attachment element such that once received the attachment element is affixed to the central portion in an immobile manner.

29. The fixation tray of claim 28, further comprising one or a plurality of registration elements either entirely embedded within the central portion or else affixed in a recess on an exposed surface of said central portion.

30. The fixation tray of claim 28, wherein the central portion has a top surface and wherein carved into the top surface is one or a plurality of recesses shaped for receiving and fixedly holding one or a plurality of registration elements.

* * * * *